United States Patent [19]
Gearing et al.

[11] Patent Number: 6,133,423
[45] Date of Patent: Oct. 17, 2000

[54] DON-1 GENE AND POLYPEPTIDES AND USES THEREFOR

[75] Inventors: David P. Gearing, Wellesley; Samantha J. Busfield, Cambridge, both of Mass.

[73] Assignee: Millennium Pharmaceuticals, Inc., Cambridge, Mass.

[21] Appl. No.: 09/398,496

[22] Filed: Sep. 17, 1999

Related U.S. Application Data

[60] Division of application No. 08/753,007, Nov. 19, 1996, which is a continuation-in-part of application No. 08/699,591, Aug. 19, 1996, abandoned.

[51] Int. Cl.$^7$ .................................................. C07K 14/475
[52] U.S. Cl. ........................................ 530/350; 530/399
[58] Field of Search ...................................... 530/350, 399

[56] References Cited

U.S. PATENT DOCUMENTS 5,912,326  6/1999  Chang .

OTHER PUBLICATIONS

Ben–Baruch et al., "Neu Differentiation Factors: A Family of Alternatively Spliced Neuronal and Mesenchymal Factors" Proc. Soc. Exp. Biol. Med. 206:221–227, 1994.

Prigent et al., "The Type 1 (EGFR–Related) Family of Growth Factor Receptors and their Ligands" Prog. Growth Factor Res. 4:1–24, 1992.

Slamon et al., "Human Breast Cancer: Correlation of Relapse and Survival with Amplification of the HER–2/neu Oncogene" Science 235:177–182, 1982.

Tzahar et al., "Erb–3 and ErbB–4 Function as the Respective Low and High Affinity Receptors of All Neu Differentiation Factor/Heregulin Isoforms" J. of Biol. Chem. 269:25226–25233, 1994.

Wen et al., "New Differentiation Factor: A Transmembrane Glycoprotein Containing an EGF Domain and an Immunoglobulin Homology Unit" Cell 69:559–572, 1992.

*Primary Examiner*—Marianne P. Allen
*Attorney, Agent, or Firm*—Fish & Richardson P.C.

[57] ABSTRACT

The present invention relates to the identification and characterization of a novel gene called don-1 related to epidermal growth factors (EGF) such as the neuregulins, and methods of preparing and using alternate splice forms of this gene to express new Don-1 polypeptides.

13 Claims, 16 Drawing Sheets

```
                                                                                   56
CACCCGGCCCAAGCTGAAGAAG CCTAACGGCAAAAACATCAAGAAGAGGTGGGCAAGATCCTGTGCACTGACTGCGC
                        M   K   S   Q   N   P   Q   T   G   E   V   G   E   K   Q   S   L      14
                       ATG AAG AGC CAG ACA GGA GAG GTG GGT GAG AAG CAG TCG CTC    120

K   C   E   A   A   A   G   N   P   Q   P   S   Y   R   W   F   K   D   G   K        34
AAG TGT GAG GCA GCG GCG GGA AAC CCC CAG CCC TCC TAT CGC TGG TTC AAG GAT GGC AAG       180

E   L   N   R   S   R   D   I   R   I   K   Y   G   N   V   R   K   N   S   R        54
GAA CTC AAC CGG AGT CGT GAT ATT CGC ATC AAG TAT GGC AAT GTC AGA AAG AAC TCA CGG       240

L   Q   F   N   K   V   R   V   E   D   A   G   E   Y   V   C   E   A   E   N        74
CTA CAG TTC AAC AAA GTG AGG GTG GAG GAT GCC GGG GAG TAC GTC TGT GAG GCC GAG AAC       300

I   L   G   K   D   T   V   R   G   R   L   H   V   N   S   V   S   T   T   L        94
ATC CTT GGG AAG GAC ACC GTG AGG GGC CGA CTC CAT GTC AAC AGC GTG AGC ACC ACT CTG       360

S   S   W   S   G   H   A   R   K   C   N   E   T   A   K   S   Y   C   V   N       114
TCA TCC TGG TCG GGA CAT GCC CGG AAG TGC AAT GAG ACC GCC AAG TCC TAC TGT GTG AAT       420

G   G   V   C   Y   Y   I   E   G   I   N   Q   L   S   C   K   C   P   N   G       134
GGA GGC GTG TGC TAC TAC ATC GAG GGC ATC AAC CAG CTC TCC TGC AAA TGT CCA AAC GGA       480

F   F   G   Q   R   C   L   E   K   L   P   L   R   Y   M   P   D   P   K          154
TTC TTC GGA CAG AGA TGT CTG GAG AAA CTG CCT TTG CGA TAC ATG CCA GAT CCT AAG         540

Q   K   A   E   L   Y   Q   K   R   V   L   T   I   T   G   I   C   V   A         174
CAA AAG GCT GAG CTG TAC CAG AAG AGA GTG CTG ACA ATT ACT GGT ATC TGT GTG GCC         600
```

```
  L   L   V   V   I   G   V   C   V   A   Y   C   K   K   T   K   Q   R   R    194
  CTG CTG GTC GTG ATC GGC GTC TGT GTG GCC TAC TGC AAG AAA ACC CAG AAA CAG AGG AGG   660

Q   M   H   H   P   H   L   R   Q   N   M   C   A   H   Q   N   R   S   L   A    214
  CAG ATG CAT CAT CCC CAT CTC CGG CAG AAC ATG TGC CAC CAG AAC CGA AGC CTG GCC   720

N   G   P   S   H   P   T   R   L   D   P   E   I   A   M   A   D   Y   I   S    234
  AAC GGG CCC AGC CAC CCT ACA CGG CTG GAC CCT GAG ATC GCA ATG GCA GAT TAC ATC TCC   780

K   N   V   P   A   T   H   D   V   H   E   R   A   T   E   M   T   F   S   G    254
  AAA AAT GTG CCA GCT ACA GAC GTG CAC GAG AGG GCT GAG ATG ACC TTC TCT GGG   840

S   H   S   C   P   S   C   T   H   S   P   I   C   T   A   T   P   S   H   R    274
  AGC CAC TCC TGT CCA TCA CCT ACA CAC TCT ATC TGC ACA GCC ACG CCC AGC CAC AGA   900

H   E   S   H   L   W   S   R   H   L   E   S   R   S   E   S   D   S   Q   S    294
  CAT GAG AGC CAC CTA TGG TCA AGC CAC CAC CTG GAA TCA CGT AGC GAG TCC GAT TCC CAG TCA   960

G   I   M   L   S   V   G   A   Y   L   S   N   C   V   C   A   M   V   E   A    314
  GGC ATC ATG CTA TCA GTA GGC TAC CTG AGC AAC TGC GTG TGT GCC ATG GTG GAG GCA   1020

R   A   R   R   A   A   A   A   D   S   L   R   S   Q   A   A   M   P   P    334
  CGG GCG CGG AGG GCA GCA GCA GCT GAC TCT CTG CGT AGC AGG CAG GCC ATG CCA CCC   1080

Y   H   D   S   R   A   I   R   L   S   P   D   V   P   H   F   H   Y   S   A    354
  TAC CAT GAC TCC ATA GAC GCT CGC CTC TCG CCC GAC GTG CCA CAC TTC TAC TCG GCC   1140

L   T   T   P   A   R   T   I   S   T   A   H   A   V   Y   S   L   A   T   Q    374
  TTG ACC ACG CCC GCT CGC ACG ATC TCG ACG GCT CAT GCC GTG TAC TCG CTG GCC ACG CAG   1200

P   T   F   E   I   P   N   S   A   H   V   S   P   A   P   L   P   A   A    394
  CCG ACT TTC GAG ATC ACG CCC AAC TCT GCG CAT GCC GTG TCT CCC GCC CCG CTG CCC GCC GCG   1260
```

| | | | | | | | | | | | |
|---|---|---|---|---|---|---|---|---|---|---|---|
| P CCC | I ATC | S AGC | Y TAC | R CGC | L CTG | A GCG | E GAG | Q CAG | Q CAG | P CCG | L CTC | R CGG | H CAT | P CCA | A GCG | P CCG | P CCC | G GGC | 414 1320 |
| P CCG | G GGG | G GGG | S TCG | G GGG | G GGG | P CCC | G GGA | A GCG | D GAC | M ATG | Q CAG | R CGC | S AGC | Y TAC | D GAC | Y TAC | Y TAC | Y TAC | 434 1380 |
| P CCT | A GCG | A GCG | G GGG | P CCC | G GGG | R CGG | S AGC | A GCC | C TGC | A GCC | L CTG | S AGC | S AGC | L TTG | G GGC | G GGC | S AGC | 454 1440 |
| L CTG | P CCC | A GCC | S AGC | P CCC | F TTC | R CGC | I ATC | P CCG | E GAG | D GAC | D GAC | E GAG | Y TAC | T ACC | Q CAG | E GAG | A GCG | 474 1500 |
| A GCG | P CCC | P CCC | P CCC | P CCC | P CCC | P CCG | R CGG | P CCG | R CGC | G GGG | L TTG | R CGG | A GCG | S TCC | R CGC | T ACG | G GGC | G GGG | 494 1560 |
| P CCG | R CGG | R CGG | W TGG | R CGG | R CGG | S TCC | R CGG | L CTC | N AAC | G GGG | S AGC | A GCG | A GCA | Q CAG | R CGC | S TCG | A GCG | A GCG | 514 1620 |
| R CGG | D GAC | S TCG | L CTG | S TCA | D GAC | A GCG | G GGG | S TCG | G GGT | G GGC | S TCG | A GCC | A GCC | T ACG | A GCG | G GGC | A GCG | 534 1680 |
| D GAC | A GCG | D GAC | D GAC | L TTG | A GCG | D GAC | A GCG | G GGG | L CTG | S AGC | A GCG | E GAG | S AGC | T ACG | P CCA | F TTC | L CTC | D GAC | 554 1740 |
| A GCG | A GCG | A GCG | H CAC | A GCG | L TTG | R CGC | S TCG | D GAC | S TCG | A GCG | P CCG | P CCG | L CTG | C TGC | P CCC | A GCC | D GAC | S AGC | 574 1800 |
| T ACT | Y TAC | Y TAC | S TCC | D GAC | Q CAG | L CTG | D GAC | S AGC | H CAC | S AGC | T ACG | S AGC | T ACG | R CGC | A GCC | R CGG | H CAC | R CGG | 594 1860 |
| P CCC | T ACG | R AGG | A GCC | K AAG | Q CAG | D GAC | S TCG | G GGG | S TCG | P CCC | T ACG | R CGC | A GCC | L * CTC TAA | | | | | 605 1896 |

FIG. 1C

```
GGCCCCCGCCTCGCCCCGCCCCACGTCTCCAAGGAGAGCGGAGACCACCGACTGGAGAGGGAAAAGGAGCGAACAAAGA
AATAAAAATATTTTTATTTCTATAAAGGAAAAACAAAATGTTTTATTTCATTTTAGCAAAAAAATTGT
CTTATAATACTAGCTAACGGCAAAGACGTTTTATAGGAAACTATTTATATGTAACATCCTGATTTACAGCTTCGGAA
AAAAAAAGAAACAACAAAAAAAAAAAAAACTCGAGGGGGCCCGGTACCCAATTCGCCCTATAGTGAGTC
GTATTACAATTCACTGGCCGTCGTTTACAACGTCGTGACTGGGAAACCCTGGCGTTACCAACTTAATCGCCTTGCA
GCACATCCCCTTTCGCCAGCTGGCGTAATAGCGAAAAGGCCCGCACCGATCGCCCTTCCCAACAGTTGCGCAGCCTGA
ATGGCGAATGGCAAATTGTAAGCGTTAAATATTTTGTTAAATCCCGTTAAATTCCCGTTAAATCACTCATTTTTAAC
CAATAGGCCGAAATCGGC
```

FIG. 1D

```
                                                                                                                  56
CCTAACGGCAAAAACATCAAGAAAGAGGTGGGCAAGATCCTGTGCACTGACTGCGC

M   K   S   Q   T   G   E   V   G   E   K   Q   S   L                                   14
CACCCGGCCCAAGCTGAAGAAG ATG AAG AGC CAG ACA GGA GAG GTG GGT GAG AAG CAG TCG CTC                                  120

K   C   E   A   A   G   N   P   Q   S   Y   R   W   F   K   D   G   K                                          34
AAG TGT GAG GCA GCG GGA AAC CCC CAG TCC TAT CGC TGG TTC AAG GAT GGC AAG                                         180

E   L   N   R   S   R   D   I   R   I   K   Y   G   N   V   R   K   N   S   R                                  54
GAA CTC AAC CGG AGT CGT GAT ATT CGC ATC AAG TAT GGC AAT GTC AGA AAG AAC TCA CGG                                 240

L   Q   F   N   K   V   R   V   E   D   A   G   E   Y   C   V   C   E   A   E   N                              74
CTA CAG TTC AAC AAA GTG AGG GTG GAG GAT GCC GAG TAC TGT GTC TGT GAG GCC GAG AAC                                 300

I   L   G   K   D   T   V   R   G   H   R   L   C   N   E   T   A   K   S   V   T   L                          94
ATC CTT GGG AAG GAC ACC GTG AGG GGC CAT CTC TGC AAT GAG ACC GCC AAG AGC GTG ACT CTG                             360

S   S   W   S   G   H   A   R   K   C   N   Y   S   A   K   S   Y   C   K   P   N   G                         114
TCA TCC TGG TCG GGA CAT GCA AGG AAG TGC AAT TAC TCC AAG AGC TAC TGT AAA CCA AAC GGA                             420

G   G   V   C   Y   T   Y   I   E   N   Q   L   S   C   K   C   L   Y   M   P   D   P   K                     134
GGA GGC GTG TGC TAC TAC ATC GAG AAC CAG CTC TCC TGC AAA TGT CCA TAT ATG CCA GAT CCT AAG                         480

F   F   Q   Q   R   R   C   E   K   L   R   L   V   S   S   Q   W   T   S                                     154
TTC TTC GGA CAG CAG AGA TGT GAG AAA CTG CGA TTG GTC AGT TCG CAA TGG TCA ACT TCT                                 540

Q   S   V   L   T   D   T   P   G   T   G   V   R   L   Y   P   D   K                                         174
CAA AGT GTC CTG ACA GAT ACA CCG GGG ACA GGT GTC AGG TTG TAC CCT GAT AAG                                         600

P   T   L   D   L   N   *                                                                                      181
CCA ACC TTG GAT TTG AAT TGA                                                                                     624
```

FIG. 2A

AGGAGGCTGAGGAGCTGTACCAGAAGAGAGTGCTGACAATTACTGGTATCTGTGTGGCCCTGCTGTCGTGGGCATCGT
CTGTGGTCGCCTACTGCAAGACCAAAAACAGAGGAGCAGATGCATCATCTCCGGCAGAACATGTGCCAGCC
CACCAGAACCGAAGCCTGGCCAACGGGCCCAGCCACCCTGGACCCTGAGGAGATCCAGATGGCAGATTACATCT
CCAAAAATGTGCCAGCTACAGACCACGTGATCCGGAGGAAGCTGAGACCAGTTCTCTGGGAGCCACTCCTGTTCACC
TTCTCACCACTGCTCCACAGCCACCTCCAGCCACAGACATGAGAGCCACACGTGGAGCCTGGAACGTTCAGAG
AGCCTGACCTCGGATTCCCAGTCAGGCATCATCAGTAGGCACCAGCAAGTGCAACAGCCCAGCATGTGTGG
AGGCACGGGCGCGGAGGCAGCAGCCTACACAGCCAGGGCTGCCATGCCACCCTACCATGACTCCAT
AGACTCGCTGCGTGACTCTCCACACAGTGAAAGGTACGTGTCAGCCTTGACCACGCCCGCTCGCCCTGTGGAC
TTCCACTACTCGCTGCCACGCAGGTGCCGACTTTCGAGATCACGTGCCAACTCGCTGCGCTGTCGCTGCCGC
CCGCCGCGCCCATCAGCTACCGCTGGGAGCAGCAGCCGCTCCTGCGCATCCAGCCGCCCGGCCCGGGCCGGG
GTCGGGGCCCGGAGCGGACATGCAGCGGCAGCTACGACAGCTACTACCCTGCGGCCGCGGGCCGCGGGCAGC
GCCTGCGCGTGGGAGGCAGCTTGGGCAGCCTGCCCGCCAGCCCCCTTCCGCCATCCCGGAGGACGAGTACGAGACCA
CGCAGGAGTGCGCCCCCCGCCGCCCGCCGGCCG

FIG. 2B

```
CAGCTACAGCGACAGCAGCAGCAGCAGCAGCGAGAGGAGCAGCAGCAGCAGCAGCAGCAG    60

CAGCGAGAGCGGCAGCAGCAGCAGGAGCAGCAGCAACAACAGCAGCATCTCTCGTCCCGC   120

TGCGCCCCAGAGCCGCGGCCGCAGCAACAGCCGCAGCCCCGCAGCCCCGCAGCCCGGAG    180

AGCCGCCGCCCGTTCGCGAGCCGCAGCCGCCGGCGGCATGAGGCGCGACCCGGCCCCCGG   240

CTTCTCCATGCTGCTCTTCGGTGTGTCGCTCGCCTGCTACTCGCCCAGCCTCAAGTCAGT   300

GCAGGACCAGGCGTACAAGGCACCCGTGGTGGTGGAGGGCAAGGTACAGGGGCTGGTCCC   360

AGCCGGCGGCTCCAGCTCCAACAGCACCCGAGAGCCGCCCGCCTCGGGTCGGGTGGCGTT   420

GGTAAAGGTGCTGGACAAGTGGCCGCTCCGGAGCGGGGGGCTGCAGCGCGAGCAGGTGAT   480

CAGCGTGGGCTCCTGTGTGCCGCTCGAAAGGAACCAGCGCTACATCTTTTTCCTGGAGCC   540

CACGGAACAGCCCTTAGTCTTTAAGACGGCCTTTGCCCCCCTGATACCAACGGCAAAAAT   600

CTCAAGAAAGAGGTGGGCAAGATCCTGTGCACTGACTGCGCCACCCGGCCCAAGTTGAAG   660
      M  K  S  Q  T  G  Q  V  G  E  K  Q  S  L  K  C  E  A  A     19
AAGATGAAGAGCCAGACGGGACAGGTGGGTGAGAAGCAATCGCTGAAGTGTGAGGCAGCA   720
   A  G  N  P  Q  P  S  Y  R  W  F  K  D  G  K  E  L  N  R  S    39
GCCGGTAATCCCCAGCCTTCCTACCGTTGGTTCAAGGATGGCAAGGAGCTCAACCGCAGC   780
   R  D  I  R  I  K  Y  G  N  G  R  K  N  S  R  L  Q  F  N  K    59
CGAGACATTCGCATCAAATATGGCAACGGCAGAAAGAACTCACGACTACAGTTCAACAAG   840
   V  K  V  E  D  A  G  E  Y  V  C  E  A  E  N  I  L  G  K  D    79
GTGAAGGTGGAGGACGCTGGGGAGTATGTCTGCGAGGCCGAGAACATCCTGGGGAAGGAC   900
   T  V  R  G  R  L  Y  V  N  S  V  S  T  T  L  S  S  W  S  G    99
ACCGTCCGGGGCCGGCTTTACGTCAACAGCGTGAGCACCACCCTGTCATCCTGGTCGGGG   960
   H  A  R  K  C  N  E  T  A  K  S  Y  C  V  N  G  G  V  C  Y   119
CACGCCCGGAAGTGCAACGAGACAGCCAAGTCCTATTGCGTCAATGGAGGCGTCTGCTAC  1020
```

FIG. 3A

```
        Y   I   E   G   I   N   Q   L   S   C   K   C   P   N   G   F   F   G   Q   R   139
TACATCGAGGGCATCAACCAGCTCTCCTGCAAATGTCCAAATGGATTCTTCGGACAGAGA 1080

C   L   E   K   L   P   L   R   L   Y   M   P   D   P   K   Q   K   H   L   G   159
TGTTTGGAGAAACTGCCTTTGCGATTGTACATGCCAGATCCTAAGCAAAAGCACCTTGGA 1140

F   E   L   K   E   A   E   E   L   Y   Q   K   R   V   L   T   I   T   G   I   179
TTTGAATTAAAGGAAGCCGAGGAGCTGTACCAGAAGAGGGTCCTGACCATCACGGGCATC 1200

C   V   A   L   L   V   V   G   I   V   C   V   V   A   Y   C   K   T   K   K   199
TGCGTGGCTCTGCTGGTCGTGGGCATCGTCTGTGTGGTGGCCTACTGCAAGACCAAAAAA 1260

Q   R   K   Q   M   H   N   H   L   R   Q   N   M   C   P   A   H   Q   N   R   219
CAGCGGAAGCAGATGCACAACCACCTCCGGCAGAACATGTGCCCGGCCCATCAGAACCGG 1320

S   L   A   N   G   P   S   H   P   R   L   D   P   E   E   I   Q   M   A   D   239
AGCTTGGCCAATGGGCCCAGCCACCCCCGGCTGGACCCAGAGGAGATCCAGATGGCAGAT 1380

Y   I   S   K   N   V   P   A   T   D   H   V   I   R   R   E   T   E   T   T   259
TATATTTCCAAGAACGTGCCAGCCACAGACCATGTCATCAGGAGAGAAACTGAGACCACC 1440

F   S   G   S   H   S   C   S   P   S   H   H   C   S   T   A   T   P   T   S   279
TTCTCTGGGAGCCACTCCTGTTCTCCTTCTCACCACTGCTCCACAGCCACACCCACCTCC 1500

S   H   R   H   E   S   H   T   W   S   L   E   R   S   E   S   L   T   S   D   299
AGCCACAGACACGAGAGCCACACGTGGAGCCTGGAACGTTCTGAGAGCCTGACTTCTGAC 1560

S   Q   S   G   I   M   L   S   S   V   G   T   S   K   C   N   S   P   A   C   319
TCCCAGTCGGGGATCATGCTATCATCAGTGGGTACCAGCAAATGCAACAGCCCAGCATGT 1620

V   E   A   R   A   R   R   A   A   A   Y   N   L   E   E   R   R   R   A   T   339
GTGGAGGCCCGGGCAAGGCGGGCAGCAGCCTACAACCTGGAGGAGCGGCGCAGGGCCACC 1680

A   P   P   Y   H   D   S   V   D   S   L   R   D   S   P   H   S   E   R   Y   359
GCGCCACCCTATCACGATTCCGTGGACTCCCTTCGCGACTCCCCACACAGCGAGAGGTAC 1740

V   S   A   L   T   T   P   A   R   L   S   P   V   D   F   H   Y   S   L   A   379
GTGTCGGCCCTGACCACGCCCGCGCGCCTCTCGCCCGTGGACTTCCACTACTCGCTGGCC 1800

T   Q   V   P   T   F   E   I   T   S   P   N   S   A   H   A   V   S   L   P   399
ACGCAGGTGCCAACTTTCGAGATCACGTCCCCCAACTCGGCGCACGCCGTGTCGCTGCCG 1860

P   A   A   P   I   S   Y   R                                               407
CCGGCGGCGCCCATCAGTTACCGC                                                         1884
```

FIG. 3B

```
CGGGCGGCGGGGGCGCAGCGCGGCAGCGGAGAGCTGAGGCCGTCCCACCGCCTGGGACCC    60
                 M  S  E  S  R  R  R  G  R  G  R  G  K  K  H  P  E    17
CGTGCAGAATGTCGGAGTCCAGGAGGAGGGGCCGCGGCCGCGGCAAGAAGCACCCAGAGG   120

G  R  K  R  E  R  E  P  D  P  G  E  K  A  T  R  P  K  L  K    37
GGAGGAAGCGGGAGAGGGAGCCCGATCCCGGGGAGAAAGCCACCCGGCCCAAGTTGAAGA   180

K  M  K  S  Q  T  G  Q  V  G  E  K  Q  S  L  K  C  E  A  A    57
AGATGAAGAGCCAGACGGGACAGGTGGGTGAGAAGCAATCGCTGAAGTGTGAGGCAGCAG   240

A  G  N  P  Q  P  S  Y  R  W  F  K  D  G  K  E  L  N  R  S    77
CCGGTAATCCCCAGCCTTCCTACCGTTGGTTCAAGGATGGCAAGGAGCTCAACCGCAGCC   300

R  D  I  R  I  K  Y  G  N  G  R  K  N  S  R  L  Q  F  N  K    97
GAGACATTCGCATCAAATATGGCAACGGCAGAAAGAACTCACGACTACAGTTCAACAAGG   360

V  K  V  E  D  A  G  E  Y  V  C  E  A  E  N  I  L  G  K  D   117
TGAAGGTGGAGGACGCTGGGGAGTATGTCTGCGAGGCCGAGAACATCCTGGGGAAGGACA   420

T  V  R  G  R  L  Y  V  N  S  V  S  T  T  L  S  S  W  S  G   137
CCGTCCGGGGCCGGCTTTACGTCAACAGCGTGAGCACCACCCTGTCATCCTGGTCGGGGC   480

H  A  R  K  C  N  E  T  A  K  S  Y  C  V  N  G  G  V  C  Y   157
ACGCCCGGAAGTGCAACGAGACAGCCAAGTCCTATTGCGTCAATGGAGGCGTCTGCTACT   540

Y  I  E  G  I  N  Q  L  S  C  K  C  P  N  G  F  F  G  Q  R   177
ACATCGAGGGCATCAACCAGCTCTCCTGCAAATGTCCAAATGGATTCTTCGGACAGAGAT   600

C  L  E  K  L  P  L  R  L  Y  M  P  D  P  K  Q  K  A  E  E   197
GTTTGGAGAAACTGCCTTTGCGATTGTACATGCCAGATCCTAAGCAAAAAGCCGAGGAGC   660

L  Y  Q  K  R  V  L  T  I  T  G  I  C  V  A  L  L  V  V  G   217
TGTACCAGAAGAGGGTCCTGACCATCACGGGCATCTGCGTGGCTCTGCTGGTCGTGGGCA   720

I  V  C  V  V  A  Y  C  K  T  K  K  Q  R  K  Q  M  H  N  H   237
TCGTCTGTGTGGTGGCCTACTGCAAGACCAAAAAACAGCGGAAGCAGATGCACAACCACC   780
```

FIG. 4A

```
L   R   Q   N   M   C   P   A   H   Q   N   R   S   L   A   N   G   P   S   H      257
TCCGGCAGAACATGTGCCCGGCCCATCAGAACCGGAGCTTGGCCAATGGGCCCAGCCACC              840

P   R   L   D   P   E   E   I   Q   M   A   D   Y   I   S   K   N   V   P   A      277
CCCGGCTGGACCCAGAGGAGATCCAGATGGCAGATTATATTTCCAAGAACGTGCCAGCCA              900

T   D   H   V   I   R   R   E   T   E   T   T   F   S   G   S   H   S   C   S      297
CAGACCATGTCATCAGGAGAGAAACTGAGACCACCTTCTCTGGGAGCCACTCCTGTTCTC              960

P   S   H   H   C   S   T   A   T   P   T   S   S   H   R   H   E   S   H   T      317
CTTCTCACCACTGCTCCACAGCCACACCCACCTCCAGCCACAGACACGAGAGCCACACGT             1020

W   S   L   E   R   S   E   S   L   T   S   D   S   Q   S   G   I   M   L   S      337
GGAGCCTGGAACGTTCTGAGAGCCTGACTTCTGACTCCCAGTCGGGGATCATGCTATCAT             1080

S   V   G   T   S   K   C   N   S   P   A   C   V   E   A   R   A   R   R   A      357
CAGTGGGTACCAGCAAATGCAACAGCCCAGCATGTGTGGAGGCCCGGGCAAGGCGGGCAG             1140

A   A   Y   N   L   E   E   R   R   R   A   T   A   P   P   Y   H   D   S   V      377
CAGCCTACAACCTGGAGGAGCGGCGCAGGGCCACCGCGCCACCCTATCACGATTCCGTGG             1200

D   S   L   R   D   S   P   H   S   E   R   Y   V   S   A   L   T   T   P   A      397
ACTCCCTTCGCGACTCCCCACACAGCGAGAGGTACGTGTCGGCCCTGACCACGCCCGCGC             1260

R   L   S   P   V   D   F   H   Y   S   L   A   T   Q   V   P   T   F   E   I      417
GCCTCTCGCCCGTGGACTTCCACTACTCGCTGGCCACGCAGGTGCCAACTTTCGAGATCA             1320

T   S   P   N   S   A   H   A   V   S   L   P   P   A   A   P   I   S   Y   R      437
CGTCCCCCAACTCGGCGCACGCCGTGTCGCTGCCGCCGGCGGCGCCCATCAGTTACCGCC             1380

L   A   E   Q   Q   P   L   L   R   H   P   A   P   P   G   P   G   P   G   P      457
TGGCCGAGCAGCAGCCGTTACTGCGGCACCCGGCGCCCCCGGCCCGGGACCCGGACCCG              1440

G   P   G   P   G   P   G   A   D   T   G   I                                       469
GGCCCGGGCCCGGGCCCGGCGCAGACACCGGAATTC                                      1476
```

FIG. 4B

```
        1                                                                    50
ndf     MSERKEGRGK  GKGKKKDRGS  RGKPGPAEGD  PSPALPPRLK  EMKSQESAAG
hrg-b   MSERKEGRGK  GKGKKKERGS  GKKPESAAGS  QSPALPPRLK  EMKSQESAAG
        MSESRRRGR.  GRGKKHPEGR  KREREPDP..  GEKATRPKLK  KMKSQTGQVG
        ..........  ..........  ..........  ..........  .MKSQTGQVG
        ..........  ..........  ..........  ..........  .MKSQTGEVG
        ..........  ..........  ..........  ..........  ..........

51                                                                   100
ndf     SKLVLRCETS  SEYSSLRFKW  FKNGNELNRK  NKPENIKIQK  KPGKSELRIN
hrg-b   SKLVLRCETS  SEYSSLRFKW  FKNGNELNRK  NKPQNIKIQK  KPGKSELRIN
        EKQSLKCEAA  AGNPQPSYRW  FKDGKELNR.  SRDIRIKYGN  GRKNSRLQFN
        EKQSLKCEAA  AGNPQPSYRW  FKDGKELNR.  SRDIRIKYGN  GRKNSRLQFN
        EKQSLKCEAA  AGNPQPSYRW  FKDGKELNR.  SRDIRIKYGN  VRKNSRLQFN
        ..........  ..........  ..........  ....RIKYGN  GRKNSRLQFN 101                                                                  150
ndf     KASLADSGEY  MCKVISKLGN  DSASANITIV  ESNEFITGMP  ASTETAYVSS
hrg-b   KASLADSGEY  MCKVISKLGN  DSASANITIV  ESNEIITGMP  ASTEGAYVSS
        KVKVEDAGEY  VCEAENILGK  DTVRGRLYV.  ..........  ..........
        KVKVEDAGEY  VCEAENILGK  DTVRGRLYV.  ..........  ..........
        KVKVEDAGEY  VCEAENILGK  DTVRGRLYV.  ..........  ..........
        KVKVEDAGEY  VCEAENILGK  DTVRGRLYV.  ..........  ..........

151                                                                  200
ndf     ESPIRISVST  EGANTSSSTS  TSTTGTSHLI  KCAEKEKTFC  VNGGECFTVK
hrg-b   ESPIRISVST  EGANTSSSTS  TSTTGTSHLV  KCAEKEKTFC  VNGGECFMVK
        .....NSVST  ....TLSSWS  ......GHAR  KCNETAKSYC  VNGGVCYYIE
        .....NSVST  ....TLSSWS  ......GHAR  KCNETAKSYC  VNGGVCYYIE
        .....NSVST  ....TLSSWS  ......GHAR  KCNETAKSYC  VNGGVCYYIE
        .....NSVST  ....TLSSWS  ......GHAR  KCNETAKSYC  VNGGVCYYIE 201                                                                  250
ndf     DLSNPSRYLC  KCQPGFTGAR  CTENV.....  .PMKVQ....  .TQEKAEELY
hrg-b   DLSNPSRYLC  KCPNEFTGDR  CQNYVMASFY  KHLGIE....  .FME.AEELY
        GINQLS...C  KCPNGFFGQR  CLEKLPLRLY  MPDPKQK...  .....AEELY
        GINQLS...C  KCPNGFFGQR  CLEKLPLRLY  MPDPKQKHLG  FELKEAEELY
        GINQLS...C  KCPNGFFGQR  CLEKLPLRLY  MPDPKQK...  .....AEELY
        GINQLS...C  KCPNGFFGQR  CLEKLPLRLY  MPDPKQSVL.. .....AEELY 251                                                                  300
ndf     QKRVLTITGI  CIALLVVGIM  CVVAYCKTKK  QRQKLHDRLR  QSLRSERSNL
hrg-b   QKRVLTITGI  CIALLVVGIM  CVVAYCKTKK  QRKKLHDRLR  QSLRSERNNM
        QKRVLTITGI  CVALLVVGIV  CVVAYCKTKK  QRKQMHNHLR  QNMCPAHQN.
        QKRVLTITGI  CVALLVVGIV  CVVAYCKTKK  QRKQMHNHLR  QNMCPAHQN.
        QKRVLTITGI  CVALLVVGIV  CVVAYCKTKK  QRRQMHHHLR  QNMCPAHQN.
        ..WDTPGTGV  SSSQWSTSPS  TLDN......  ..........  ..........

301                                                                  350
ndf     VNIANGPHHP  NPPPENVQLV  NQYVSKNVIS  SEHIVEREVE  TSFSTSHYTS
hrg-b   MNIANGPHHP  NPPPENVQLV  NQYVSKNVIS  SEHIVEREAE  TSFSTSHYTS
        RSLANGPSHP  RLDPEEIQM.  ADYISKNVPA  TDHVIRRETE  TTFSGSHSCS
        RSLANGPSHP  RLDPEEIQM.  ADYISKNVPA  TDHVIRRETE  TTFSGSHSCS
        RSLANGPSHP  RLDPEEIQM.  ADYISKNVPA  TDHVIRREAE  TTFSGSHSCS
        ..........  ..........  ..........  ..........  ..........
```

FIG. 5A

```
          351                                                           400
ndf       TAHHSTTVTQ  TP.....SHS  WSNGHTESVI  SESNSVIMMS  SVENSRHSSP
hrg-b     TAHHSTTVTQ  TP.....SHS  WSNGHTESIL  SESHSVIVMS  SVENSRHSSP
          PSHHCSTATP  TSSHRHESHT  WSLERSESLT  SDSQSGIMLS  SVGTSKCNSP
          PSHHCSTATP  TSSHRHESHT  WSLERSESLT  SDSQSGIMLS  SVGTSKCNSP
          PSHHCSTATP  TSSHRHESHT  WSLERSESLT  SDSQSGIMLS  SVGTSKCNSP
          ..........  ..........  ..........  ..........  ..........

401                                                           450
ndf       A..GGPRGRL  HGLGGPRD.N  SFLRHARETP  DSYRDSPHSE  R.........
hrg-b     T..GGPRGRL  NGTGGPRECN  SFLRHARETP  DSYRDSPHSE  RYVSAMTTPA
          ACVEARARRA  AAYNLEERRR  ATAPPYHDSV  DSLRDSPHSE  RYVSALTTPA
          ACVEARARRA  AAYNLEERRR  ATAPPYHDSV  DSLRDSPHSE  RYVSALTTPA
          ACVEARARRA  AAYSQEERRR  AAMPPYHDSI  DSLRDSPHSE  RYVSALTTPA
          ..........  ..........  ..........  ..........  ..........

451                                                           500
ndf       ..........  ..........  ..........  ..........  ..........
hrg-b     RMSPVDFHTP  SSPKSPPSEM  SPPVSSMTVS  MPSMAVSPFM  EEERPLLLVT
          RLSPVDFHYS  LATQVPTFEI  TSPNSAHAVS  LPPAAPISYR  LAEQQPLLRH
          RLSPVDFHYS  LATQVPTFEI  TSPNSAHAVS  LPPAAPISYR  ..........
          RLSPVDFHYS  LATQVPTFEI  TSPNSAHAVS  LPPAAPISYR  LAEQQPLLRH
          ..........  ..........  ..........  ..........  ..........

501                                                           550
ndf       ..........  ..........  ..........  ..........  ..........
hrg-b     PPRLREKKFD  HHPQQFSSFH  HNPAHDSNSL  PASPLRIVED  EEYETTQEYE
          PAPPGPGPGP  GPGPGPGADT  GI........  ..........  ..........
          ..........  ..........  ..........  ..........  ..........
          PAPPGPGPGS  GPGADMQRSY  DSYYYPAAGP  GPRRSACALG  GSLGSLPASP
          ..........  ..........  ..........  ..........  ..........

551                                                           600
ndf       ..........  ..........  ..........  ..........  ..........
hrg-b     PAQEPVKKLA  NSRRAKRTKP  NGHIANRLEV  DSNTSSQSSN  SESETEDERV
          ..........  ..........  ..........  ..........  ..........
          ..........  ..........  ..........  ..........  ..........
          FRIPEDDEYE  TTQECAPPPP  PRPRTRGASR  RTSAGPRRWR  RSRLNGLAAQ
          ..........  ..........  ..........  ..........  ..........

601                                                           650
ndf       ..........  ..........  ..........  ..........  ..........
hrg-b     GEDTPFLGIQ  NPLAASLEAT  PAFRLADSRT  NPAGRFSTQE  EIQARLSSVI
          ..........  ..........  ..........  ..........  ..........
          ..........  ..........  ..........  ..........  ..........
          RARAARDSLS  LSSGSGCGSA  SASDDDADDA  DGALAAESTP  FLGLRAAHDA
          ..........  ..........  ..........  ..........  ..........

651                                                           696
ndf       ..........  ..........  ..........  ..........  ......
hrg-b     ANQDPIAV*.  ..........  ..........  ..........  ......
          ..........  ..........  ..........  ..........  ......
          ..........  ..........  ..........  ..........  ......
          LRSDSPPLCP  AADSRTYYSL  DSHSTRASSR  HSRGPPTRAK  QDSGPL
          ..........  ..........  ..........  ..........  ......
```

FIG. 5B

```
GHARKCNETAKSYCVNGGVCYYIEGINQLS...CKCPNGFFGQRCLEKLP
SHLVKCAEKEKTFCVNGGECFMVKDLSNPSRYLCKCQPGFTGARCTENVP
SHLIKCAEKEKTFCVNGGECFTVKDLSNPSRYLCKCQPGFTGARCTENVP
SHLVKCAEKEKTFCVNGGECFMVKDLSNPSRYLCKCPNEFTGDRCQNYVM
SHLTKCDIKQKAFCVNGGECYMVKDLPNPPRYLCRCPNEFTGDRCQNYVM
GKRDPCLRKYKDFCIH.GECKYVKELRAPS...CICHPGYHGERCHGLSL
NSDSECPLSHDGYCLHDGVCMYIEALDKYA...CNCVVGYIGERCQYRDL
KKKNPCNAEFQNFCIH.GECKYIEHLEAVT...CKCQQEYFGERCGEKSM
SHFNDCPDSHTQFCFH.GTCRFLVQEDKPA...CVCHSGYVGARCEHADL
```

FIG. 6

```
                                                                                      2
CGGGCGGCGGGGGCGCAGCGGAGCGCGGAGAGCTGAGGCCGTCCCACCCGCTGGGACCCCGTGCAGA ATG TCG          74
                                                                   M   S

E   S   R   R   G   R   G   R   G   K   H   P   E   G   R   K   R   E              22
GAG TCC AGG AGG GGC CGC GGC CGC GGC AAG CAC CCA GAG GGG AGG AAG CGG GAG             134

R   E   P   D   P   G   E   K   A   T   R   P   K   K   M   S   Q                  42
AGG GAG CCC GAT CCC GGG GAG AAA GCC ACC CGG CCC AAG AAG ATG AGC CAG                 194

T   G   Q   V   G   E   K   Q   S   L   K   E   A   A   G   N   P   Q              62
ACG GGA CAG GTG GGT GAG AAG CAA TCG CTG AAG GAG GCA GCC GGT AAT CCC CAG             254

P   S   Y   R   W   F   K   D   G   K   E   L   N   R   S   D   I   R   I          82
CCT TCC TAC CGT TGG TTC AAG GAT GGC AAG GAG CTC AAC CGC AGC GAC ATT CGC ATC         314

K   Y   G   N   G   R   K   N   S   R   L   Q   F   N   K   V   E   D             102
AAA TAT GGC AAC GGC AGA AAG AAC TCA CGA CTA CAG TTC AAC AAG GTG GAG GAC             374

A   G   E   Y   V   C   E   A   E   N   I   L   G   K   D   T   V   R   R         122
GCT GGG GAG TAT GTC TGC GAG GCC ATC CTG GGG AAG GAC ACC GTC CGG CGG                 434

L   Y   V   N   S   V   S   T   L   S   S   W   G   V   H   A   I   E   G         142
CTT TAC GTC AAC AGC GTG AGC ACC CTG TCA TCC TGG GGC GTC CAC GCC ATC GAG             494

N   E   T   A   K   S   Y   C   P   N   G   F   G   Q   R   K   A   E   K         162
AAC GAG ACA GCC AAG TCC TAT TGC CCA AAT GGA TTC TTC GGA CAG AAG GCC GAG             554

L   E   K   C   L                                                                  182
                                                                                    614
 N   Q   L   Y   M   P   D   P   K   Q   K   A   E   L   Y   Q   K   R             202
AAC CAG CTC TAC ATG CCA GAT CCT AAG CAA AAA GCC GAG CTG TAC CAG AAG AGG             674

P   L   R   T   G   I   C   V   A   L   V   G   I   V   C   R   V                 222
CCT TTG CGA ACG ATC TGC GTG GCT CTG GTC GGC ATC GTC TGT GTG GTG                     734

V   L   T                                                                          
GTC CTG ACC
```

FIG. 7A

| A GCC | Y TAC | C TGC | K AAG | T ACC | K AAA | K AAG | Q CAG | R CGG | K AAG | Q CAG | M ATG | H CAC | N AAC | L CTC | R CGG | Q CAG | N AAC | M ATG | 242 794 |
|---|---|---|---|---|---|---|---|---|---|---|---|---|---|---|---|---|---|---|---|
| C TGC | P CCG | A GCC | H CAT | Q CAG | N AAC | R CGG | L TTG | S AGC | A GCC | N AAT | G GGG | P CCC | S AGC | P CCC | R CGG | L CTG | D GAC | P CCA | 262 854 |
| E GAG | E GAG | I ATC | Q CAG | M ATG | A GCA | D GAT | Y TAT | I ATT | S TCC | K AAG | N AAC | V GTG | P CCA | A GCC | T ACA | D GAC | H CAT | V GTC | I ATC | 282 914 |
| R AGG | R AGA | E GAA | T ACT | E GAG | T ACC | T ACC | F TTC | S TCT | G GGG | S AGC | H CAC | C TGT | S TCC | P CCT | S TCT | H CAC | H CAC | C TGC | 302 974 |
| S TCC | T ACA | A GCC | T ACA | P CCC | T ACC | S TCC | D GAC | S AGC | H CAC | R AGA | H CAC | E GAG | S AGC | T ACG | W TGG | S AGC | L CTG | E GAA | R CGT | 322 1034 |
| S TCT | E GAG | S AGC | L CTG | T ACT | S TCT | D GAC | Q CAG | E GAG | R AGG | M ATG | L CTA | S TCA | T ACA | S TCA | G GGT | V GTG | T ACC | S AGC | 342 1094 |
| K AAA | C TGC | N AAC | S AGC | P CCA | C TGT | V GTG | E GAG | A GCC | R AGG | I ATC | R AGG | A GCA | A GCA | A GCC | Y TAC | A GCC | N AAC | L CTG | 362 1154

```
CCG TTA CTG CGG CAC CCG GCG CCC CCC GGC GAC AGC TAT GGA CCC GGA CCC GGG CCC GGG     1454
 P   G   A   D   M   Q   S   Y   D   G   Y   Y   P   A   P   G   P   G             482
CCC GGC GCA GAC ATG CAG CGC AGC GAC TAT TAT GAC CGC TAC TAC CCG GCG GGG CCC GGA    1514
 P   R   G   T   C   A   L   G   S   L   G   S   P   A   S   P   F                 502
CCG CGG GGG ACC TGC GCG CTC GGC AGC CTG GGC AGC CCG GCG CTG CCT GCC AGC CCC TTC    1574
 R   I   P   D   E   Y   E   Q   T   T   Q   E   C   A   P   P   P   P             522
CGC ATC CCC GAG GAC TAC GAG CAG ACC ACG CAG GAG TGC GCG CCC CCG CCG CCG CCG CCG    1634
 R   P   R   A   G   R   S   A   S   R   T   R   A   G   P   R   W   R   R         542
CGG CCG CGC GCG CGC GGT GCG TCC AGG CGC ACG TCG GCG CGC GGG CCC CGC CGC TGG CGC    1694
 S   R   L   N   G   L   A   A   Q   R   A   S   A   R   D   D   S   L   S   L     562
TCG CGC CTC AAC GGG CTG GCG GCG CAG CGC GCA GCC GCG GCG CGG AGG GAC GAC TCG CTG    1754
 S   G   S   G   S   A   E   S   T   P   F   L   G   D   D   A   H   D   A   D     582
AGC GGC TCG GGC GGC GCC GAG AGC ACA CCT TTC CTG GGC GAC GAC GCG GCG CAC GAC GAC    1814
 G   A   L   A   P   P   L   C   P   A   A   D   A   D   R   G   A   Y   S   L     602
GGG GCG CTG GCG CCG CCG CTG TGC CCG GCG GCC GAC GCG AGG GGG CGT GGG GCG TAC TCA    1874
 R   S   D   S   P   L   C   S   S   R   H   S   R   G   P   P   P   R   A   K     622
CGC TCG GAC TCG CCG CTG TGC TCG TCC CGC CAC AGC CGC GGG CCG CCG CCC CGG GCC AAG    1934
 S   H   S   T   R   A   S   R   A   K   Q                                         642
AGC CAC AGC ACG CGG GCC GCC AGC GCC AGA CAC AGC CGC GGG CCG CCG CCC CGG GCC AAG    1994
 D   S   A   P   L   *                                                             648
GAC TCG GCG CCA CTC TAG                                                           2012
GGCCCCGCGCGCGCCCCTCCGCCCCGCCCCCACTATCTTTAAGGAGACCAGAGACCGCCTACTGGAGAGAAAGGA        2091
GGAAAAAGAAATAAAAATATTTTATTTCTATAAAGGAAAAAAGTATAACAAAATGTTTATTTTCATTTTAGCAA        2170
AAATTGTCTTATATACTAGCTAACGGCAAAGGCGTTTTTATAGGAAACTATTTATATGTAACATCCTGATTTACAGC     2249
TTCGGAAAAAAAAAGAAA                                                                2268
```

FIG. 7C 6,133,423

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 2467 base pairs
      (B) TYPE: nucleic acid
      (C) STRANDEDNESS: single
      (D) TOPOLOGY: circular (ii) MOLECULE TYPE: cDNA (ix) FEATURE:
      (A) NAME/KEY: Coding Sequence
      (B) LOCATION: 79...1893
      (D) OTHER INFORMATION:

(xi) SEQUENCE DESCRIPTION: SEQ ID NO:1:

```
CCTAACGGCA AAAACATCAA GAAAGAGGTG GGCAAGATCC TGTGCACTGA CTGCGCCACC        60

CGGCCCAAGC TGAAGAAG ATG AAG AGC CAG ACA GGA GAG GTG GGT GAG AAG        111
                    Met Lys Ser Gln Thr Gly Glu Val Gly Glu Lys
                     1               5                      10

CAG TCG CTC AAG TGT GAG GCA GCG GCG GGA AAC CCC CAG CCC TCC TAT        159
Gln Ser Leu Lys Cys Glu Ala Ala Ala Gly Asn Pro Gln Pro Ser Tyr
             15                  20                  25

CGC TGG TTC AAG GAT GGC AAG GAA CTC AAC CGG AGT CGT GAT ATT CGC        207
Arg Trp Phe Lys Asp Gly Lys Glu Leu Asn Arg Ser Arg Asp Ile Arg
         30                  35                  40

ATC AAG TAT GGC AAT GTC AGA AAG AAC TCA CGG CTA CAG TTC AAC AAA        255
Ile Lys Tyr Gly Asn Val Arg Lys Asn Ser Arg Leu Gln Phe Asn Lys
     45                  50                  55

GTG AGG GTG GAG GAT GCC GGG GAG TAC GTC TGT GAG GCC GAG AAC ATC        303
Val Arg Val Glu Asp Ala Gly Glu Tyr Val Cys Glu Ala Glu Asn Ile
 60                  65                  70                  75

CTT GGG AAG GAC ACC GTG AGG GGC CGA CTC CAT GTC AAC AGC GTG AGC        351
Leu Gly Lys Asp Thr Val Arg Gly Arg Leu His Val Asn Ser Val Ser
                 80                  85                  90

ACC ACT CTG TCA TCC TGG TCG GGA CAT GCC CGG AAG TGC AAT GAG ACC        399
Thr Thr Leu Ser Ser Trp Ser Gly His Ala Arg Lys Cys Asn Glu Thr
             95                 100                 105

GCC AAG TCC TAC TGT GTG AAT GGA GGC GTG TGC TAC TAC ATC GAG GGC        447
Ala Lys Ser Tyr Cys Val Asn Gly Gly Val Cys Tyr Tyr Ile Glu Gly
         110                 115                 120

ATC AAC CAG CTC TCC TGC AAA TGT CCA AAC GGA TTC TTC GGA CAG AGA        495
Ile Asn Gln Leu Ser Cys Lys Cys Pro Asn Gly Phe Phe Gly Gln Arg
     125                 130                 135

TGT TTG GAG AAA CTG CCT TTG CGA TTG TAC ATG CCA GAT CCT AAG CAA        543
Cys Leu Glu Lys Leu Pro Leu Arg Leu Tyr Met Pro Asp Pro Lys Gln
140                 145                 150                 155

AAG GCT GAG GAG CTG TAC CAG AAG AGA GTG CTG ACA ATT ACT GGT ATC        591
Lys Ala Glu Glu Leu Tyr Gln Lys Arg Val Leu Thr Ile Thr Gly Ile
                 160                 165                 170

TGT GTG GCC CTG CTG GTC GTG GGC ATC GTC TGT GTG GTC GCC TAC TGC        639
Cys Val Ala Leu Leu Val Val Gly Ile Val Cys Val Val Ala Tyr Cys
             175                 180                 185

AAG ACC AAA AAA CAG AGG AGG CAG ATG CAT CAT CAT CTC CGG CAG AAC        687
Lys Thr Lys Lys Gln Arg Arg Gln Met His His His Leu Arg Gln Asn
         190                 195                 200

ATG TGC CCA GCC CAC CAG AAC CGA AGC CTG GCC AAC GGG CCC AGC CAC        735
Met Cys Pro Ala His Gln Asn Arg Ser Leu Ala Asn Gly Pro Ser His
     205                 210                 215

CCT CGG CTG GAC CCT GAG GAG ATC CAG ATG GCA GAT TAC ATC TCC AAA        783
Pro Arg Leu Asp Pro Glu Glu Ile Gln Met Ala Asp Tyr Ile Ser Lys
220                 225                 230                 235

AAT GTG CCA GCT ACA GAC CAC GTG ATC CGG AGG GAA GCT GAG ACC ACG        831
Asn Val Pro Ala Thr Asp His Val Ile Arg Arg Glu Ala Glu Thr Thr
                 240                 245                 250

TTC TCT GGG AGC CAC TCC TGT TCA CCT TCT CAC CAC TGC TCC ACA GCC        879
Phe Ser Gly Ser His Ser Cys Ser Pro Ser His His Cys Ser Thr Ala
             255                 260                 265

ACG CCC ACC TCC AGC CAC AGA CAT GAG AGC CAC ACG TGG AGC CTG GAA        927
Thr Pro Thr Ser Ser His Arg His Glu Ser His Thr Trp Ser Leu Glu
         270                 275                 280

CGT TCA GAG AGC CTG ACC TCG GAT TCC CAG TCA GGC ATC ATG CTA TCA        975
Arg Ser Glu Ser Leu Thr Ser Asp Ser Gln Ser Gly Ile Met Leu Ser
```

```
           285                 290                 295
TCA GTA GGC ACC AGC AAG TGC AAC AGC CCA GCA TGT GTG GAG GCA CGG    1023
Ser Val Gly Thr Ser Lys Cys Asn Ser Pro Ala Cys Val Glu Ala Arg
300                 305                 310                 315

GCG CGG AGG GCA GCA GCC TAC AGC CAG GAG GAG CGG CGC AGG GCT GCC    1071
Ala Arg Arg Ala Ala Ala Tyr Ser Gln Glu Glu Arg Arg Arg Ala Ala
                320                 325                 330

ATG CCA CCC TAC CAT GAC TCC ATA GAC TCG CTG CGT GAC TCT CCA CAC    1119
Met Pro Pro Tyr His Asp Ser Ile Asp Ser Leu Arg Asp Ser Pro His
            335                 340                 345

AGT GAA AGG TAC GTG TCA GCC TTG ACC ACG CCC GCT CGC CTC TCG CCC    1167
Ser Glu Arg Tyr Val Ser Ala Leu Thr Thr Pro Ala Arg Leu Ser Pro
        350                 355                 360

GTG GAC TTC CAC TAC TCG CTG GCC ACG CAG GTG CCG ACT TTC GAG ATC    1215
Val Asp Phe His Tyr Ser Leu Ala Thr Gln Val Pro Thr Phe Glu Ile
365                 370                 375

ACG TCG CCC AAC TCT GAG CAT GCC GTG TCG CTG CCG CCC GCC GCG CCC    1263
Thr Ser Pro Asn Ser Glu His Ala Val Ser Leu Pro Pro Ala Ala Pro
380                 385                 390                 395

ATC AGC TAC CGC CTG GCG GAG CAG CAG CCG CTC CTG CGG CAT CCA GCG    1311
Ile Ser Tyr Arg Leu Ala Glu Gln Gln Pro Leu Leu Arg His Pro Ala
                400                 405                 410

CCG CCC GGC CCG GGG CCG GGG TCG GGG CCC GGA GCG GAC ATG CAG CGC    1359
Pro Pro Gly Pro Gly Pro Gly Ser Gly Pro Gly Ala Asp Met Gln Arg
            415                 420                 425

AGC TAC GAC AGC TAC TAC TAC CCT GCG GCG GGG CCC GGG CCG CGG CGC    1407
Ser Tyr Asp Ser Tyr Tyr Tyr Pro Ala Ala Gly Pro Gly Pro Arg Arg
        430                 435                 440

AGC GCC TGC GCG CTG GGA GGC AGC TTG GGC AGC CTG CCC GCC AGC CCC    1455
Ser Ala Cys Ala Leu Gly Gly Ser Leu Gly Ser Leu Pro Ala Ser Pro
    445                 450                 455

TTC CGC ATC CCG GAG GAC GAC GAG TAC GAG ACC ACG CAG GAG TGC GCG    1503
Phe Arg Ile Pro Glu Asp Asp Glu Tyr Glu Thr Thr Gln Glu Cys Ala
460                 465                 470                 475

CCC CCG CCG CCG CCG CGG CCG CGC ACG CGC GGC GCG TCC CGC AGG ACG    1551
Pro Pro Pro Pro Pro Arg Pro Arg Thr Arg Gly Ala Ser Arg Arg Thr
                480                 485                 490

TCG GCG GGG CCG CGG CGC TGG CGG CGC TCC CGG CTC AAC GGG TTG GCG    1599
Ser Ala Gly Pro Arg Arg Trp Arg Arg Ser Arg Leu Asn Gly Leu Ala
            495                 500                 505

GCG CAG CGC GCA CGC GCG GCG CGG GAC TCG CTG TCA TTG AGC AGC GGT    1647
Ala Gln Arg Ala Arg Ala Ala Arg Asp Ser Leu Ser Leu Ser Ser Gly
        510                 515                 520

TCG GGC TGC GGC TCG GCG TCG GCC TCG GAC GAC GAC GCG GAC GAC GCG    1695
Ser Gly Cys Gly Ser Ala Ser Ala Ser Asp Asp Asp Ala Asp Asp Ala
    525                 530                 535

GAC GGG GCG CTG GCG GCC GAG AGC ACG CCA TTC CTC GGC CTG CGA GCG    1743
Asp Gly Ala Leu Ala Ala Glu Ser Thr Pro Phe Leu Gly Leu Arg Ala
540                 545                 550                 555

GCG CAC GAC GCG TTG CGC TCG GAC TCG CCG CCG CTG TGC CCC GCG GCC    1791
Ala His Asp Ala Leu Arg Ser Asp Ser Pro Pro Leu Cys Pro Ala Ala
                560                 565                 570

GAC AGC AGG ACT TAC TAC TCC CTG GAC AGC CAC AGC ACG CGC GCC AGC    1839
Asp Ser Arg Thr Tyr Tyr Ser Leu Asp Ser His Ser Thr Arg Ala Ser
            575                 580                 585

AGC AGA CAC AGC CGG GGG CCG CCC ACG AGG GCC AAG CAG GAC TCG GGG    1887
Ser Arg His Ser Arg Gly Pro Pro Thr Arg Ala Lys Gln Asp Ser Gly
        590                 595                 600

CCC CTC TAAGGCCCCC CGCCTCGCCC GCCCCACGTC TCCAAGGAGA GCGGAGACCA CC   1945
Pro Leu
```

-continued

Pro Leu
    605

```
GACTGGAGAG GGAAAAGGAG CGAACAAAGA AATAAAAATA TTTTTATTTT CTATAAAAGG    2005

AAAAAAGTAT AACAAAATGT TTTATTTTCA TTTTAGCAAA AAAAATTGTC TTATAATACT    2065

AGCTAACGGC AAAGACGTTT TTATAGGGAA ACTATTTATA TGTAACATCC TGATTTACAG    2125

CTTCGGAAAA AAAAAAGAA ACAACAAAAA AAAAAAAAA AAAAACTCGA GGGGGGGCCC    2185

GGTACCCAAT TCGCCCTATA GTGAGTCGTA TTACAATTCA CTGGCCGTCG TTTTACAACG    2245

TCGTGACTGG GAAAACCCTG GCGTTACCCA ACTTAATCGC CTTGCAGCAC ATCCCCCTTT    2305

CGCCAGCTGG CGTAATAGCG AAAAGGCCCG CACCGATCGC CCTTCCCAAC AGTTGCGCAG    2365

CCTGAATGGC GAATGGCAAA TTGTAAGCGT TAATATTTTG TTAAAATTCC CGTTAAATTT    2425

TTGTTAAATC ACTCATTTTT TAACCAATAG GCCGAAATCG GC                       2467
```

(2) INFORMATION FOR SEQ ID NO:2:

(i) SEQUENCE CHARACTERISTICS:
        (A) LENGTH: 605 amino acids
        (B) TYPE: amino acid
        (C) STRANDEDNESS: Not Relevant
        (D) TOPOLOGY: linear (ii) MOLECULE TYPE: protein (v) FRAGMENT TYPE: internal (xi) SEQUENCE DESCRIPTION: SEQ ID NO:2:

```
Met Lys Ser Gln Thr Gly Glu Val Gly Glu Lys Gln Ser Leu Lys Cys
  1               5                  10                  15

Glu Ala Ala Gly Asn Pro Gln Pro Ser Tyr Arg Trp Phe Lys Asp
             20                  25                  30

Gly Lys Glu Leu Asn Arg Ser Arg Asp Ile Arg Ile Lys Tyr Gly Asn
         35                  40                  45

Val Arg Lys Asn Ser Arg Leu Gln Phe Asn Lys Val Arg Val Glu Asp
     50                  55                  60

Ala Gly Glu Tyr Val Cys Glu Ala Glu Asn Ile Leu Gly Lys Asp Thr
 65                  70                  75                  80

Val Arg Gly Arg Leu His Val Asn Ser Val Ser Thr Thr Leu Ser Ser
                 85                  90                  95

Trp Ser Gly His Ala Arg Lys Cys Asn Glu Thr Ala Lys Ser Tyr Cys
                100                 105                 110

Val Asn Gly Gly Val Cys Tyr Tyr Ile Glu Gly Ile Asn Gln Leu Ser
            115                 120                 125

Cys Lys Cys Pro Asn Gly Phe Phe Gly Gln Arg Cys Leu Glu Lys Leu
        130                 135                 140

Pro Leu Arg Leu Tyr Met Pro Asp Pro Lys Gln Lys Ala Glu Glu Leu
145                 150                 155                 160

Tyr Gln Lys Arg Val Leu Thr Ile Thr Gly Ile Cys Val Ala Leu Leu
                165                 170                 175

Val Val Gly Ile Val Cys Val Val Ala Tyr Cys Lys Thr Lys Lys Gln
            180                 185                 190

Arg Arg Gln Met His His His Leu Arg Gln Asn Met Cys Pro Ala His
        195                 200                 205

Gln Asn Arg Ser Leu Ala Asn Gly Pro Ser His Pro Arg Leu Asp Pro
    210                 215                 220

Glu Glu Ile Gln Met Ala Asp Tyr Ile Ser Lys Asn Val Pro Ala Thr
```

```
            225                 230                 235                 240
Asp His Val Ile Arg Arg Glu Ala Glu Thr Thr Phe Ser Gly Ser His
                    245                 250                 255
Ser Cys Ser Pro Ser His His Cys Ser Thr Ala Thr Pro Thr Ser Ser
                260                 265                 270
His Arg His Glu Ser His Thr Trp Ser Leu Glu Arg Ser Glu Ser Leu
            275                 280                 285
Thr Ser Asp Ser Gln Ser Gly Ile Met Leu Ser Ser Val Gly Thr Ser
        290                 295                 300
Lys Cys Asn Ser Pro Ala Cys Val Glu Ala Arg Ala Arg Arg Ala Ala
305                 310                 315                 320
Ala Tyr Ser Gln Glu Glu Arg Arg Ala Ala Met Pro Pro Tyr His
                325                 330                 335
Asp Ser Ile Asp Ser Leu Arg Asp Ser Pro His Ser Glu Arg Tyr Val
                340                 345                 350
Ser Ala Leu Thr Thr Pro Ala Arg Leu Ser Pro Val Asp Phe His Tyr
            355                 360                 365
Ser Leu Ala Thr Gln Val Pro Thr Phe Glu Ile Thr Ser Pro Asn Ser
        370                 375                 380
Glu His Ala Val Ser Leu Pro Pro Ala Ala Pro Ile Ser Tyr Arg Leu
385                 390                 395                 400
Ala Glu Gln Gln Pro Leu Leu Arg His Pro Ala Pro Pro Gly Pro Gly
                405                 410                 415
Pro Gly Ser Gly Pro Gly Ala Asp Met Gln Arg Ser Tyr Asp Ser Tyr
                420                 425                 430
Tyr Tyr Pro Ala Ala Gly Pro Gly Pro Arg Arg Ser Ala Cys Ala Leu
            435                 440                 445
Gly Gly Ser Leu Gly Ser Leu Pro Ala Ser Pro Phe Arg Ile Pro Glu
        450                 455                 460
Asp Asp Glu Tyr Glu Thr Thr Gln Glu Cys Ala Pro Pro Pro Pro
465                 470                 475                 480
Arg Pro Arg Thr Arg Gly Ala Ser Arg Arg Thr Ser Ala Gly Pro Arg
                485                 490                 495
Arg Trp Arg Arg Ser Arg Leu Asn Gly Leu Ala Ala Gln Arg Ala Arg
                500                 505                 510
Ala Ala Arg Asp Ser Leu Ser Leu Ser Ser Gly Ser Cys Gly Ser
            515                 520                 525
Ala Ser Ala Ser Asp Asp Asp Ala Asp Asp Ala Asp Gly Ala Leu Ala
        530                 535                 540
Ala Glu Ser Thr Pro Phe Leu Gly Leu Arg Ala Ala His Asp Ala Leu
545                 550                 555                 560
Arg Ser Asp Ser Pro Pro Leu Cys Pro Ala Ala Asp Ser Arg Thr Tyr
                565                 570                 575
Tyr Ser Leu Asp Ser His Ser Thr Arg Ala Ser Ser Arg His Ser Arg
                580                 585                 590
Gly Pro Pro Thr Arg Ala Lys Gln Asp Ser Gly Pro Leu
            595                 600                 605

(2) INFORMATION FOR SEQ ID NO:3:

(i) SEQUENCE CHARACTERISTICS:
        (A) LENGTH: 1607 base pairs
        (B) TYPE: nucleic acid
        (C) STRANDEDNESS: single
        (D) TOPOLOGY: linear
```

(ii) MOLECULE TYPE: cDNA (ix) FEATURE:
    (A) NAME/KEY: Coding Sequence
    (B) LOCATION: 79...621
    (D) OTHER INFORMATION:

(xi) SEQUENCE DESCRIPTION: SEQ ID NO:3:

```
CCTAACGGCA AAAACATCAA GAAAGAGGTG GGCAAGATCC TGTGCACTGA CTGCGCCACC            60

CGGCCCAAGC TGAAGAAG ATG AAG AGC CAG ACA GGA GAG GTG GGT GAG AAG           111
                    Met Lys Ser Gln Thr Gly Glu Val Gly Glu Lys
                      1               5                  10

CAG TCG CTC AAG TGT GAG GCA GCG GCG GGA AAC CCC CAG CCC TCC TAT           159
Gln Ser Leu Lys Cys Glu Ala Ala Ala Gly Asn Pro Gln Pro Ser Tyr
             15                  20                  25

CGC TGG TTC AAG GAT GGC AAG GAA CTC AAC CGG AGT CGT GAT ATT CGC           207
Arg Trp Phe Lys Asp Gly Lys Glu Leu Asn Arg Ser Arg Asp Ile Arg
         30                  35                  40

ATC AAG TAT GGC AAT GTC AGA AAG AAC TCA CGG CTA CAG TTC AAC AAA           255
Ile Lys Tyr Gly Asn Val Arg Lys Asn Ser Arg Leu Gln Phe Asn Lys
     45                  50                  55

GTG AGG GTG GAG GAT GCC GGG GAG TAC GTC TGT GAG GCC GAG AAC ATC           303
Val Arg Val Glu Asp Ala Gly Glu Tyr Val Cys Glu Ala Glu Asn Ile
 60              65                  70                  75

CTT GGG AAG GAC ACC GTG AGG GGC CGA CTC CAT GTC AAC AGC GTG AGC           351
Leu Gly Lys Asp Thr Val Arg Gly Arg Leu His Val Asn Ser Val Ser
                 80                  85                  90

ACC ACT CTG TCA TCC TGG TCG GGA CAT GCC CGG AAG TGC AAT GAG ACC           399
Thr Thr Leu Ser Ser Trp Ser Gly His Ala Arg Lys Cys Asn Glu Thr
             95                 100                 105

GCC AAG TCC TAC TGT GTG AAT GGA GGC GTG TGC TAC TAC ATC GAG GGC           447
Ala Lys Ser Tyr Cys Val Asn Gly Gly Val Cys Tyr Tyr Ile Glu Gly
        110                 115                 120

ATC AAC CAG CTC TCC TGC AAA TGT CCA AAC GGA TTC TTC GGA CAG AGA           495
Ile Asn Gln Leu Ser Cys Lys Cys Pro Asn Gly Phe Phe Gly Gln Arg
    125                 130                 135

TGT TTG GAG AAA CTG CCT TTG CGA TTG TAC ATG CCA GAT CCT AAG CAA           543
Cys Leu Glu Lys Leu Pro Leu Arg Leu Tyr Met Pro Asp Pro Lys Gln
140                 145                 150                 155

AGT GTC CTG TGG GAT ACA CCG GGG ACA GGT GTC AGC AGT TCG CAA TGG           591
Ser Val Leu Trp Asp Thr Pro Gly Thr Gly Val Ser Ser Ser Gln Trp
                160                 165                 170

TCA ACT TCT CCA AGC ACC TTG GAT TTG AAT TGAAGGAGGC TGAGGAGCTG TAC         644
Ser Thr Ser Pro Ser Thr Leu Asp Leu Asn
                175                 180

CAGAAGAGAG TGCTGACAAT TACTGGTATC TGTGTGGCCC TGCTGGTCGT GGGCATCGTC         704

TGTGTGGTCG CCTACTGCAA GACCAAAAAA CAGAGGAGGC AGATGCATCA TCATCTCCGG         764

CAGAACATGT GCCCAGCCCA CCAGAACCGA AGCCTGGCCA ACGGGCCCAG CCACCCTCGG         824

CTGGACCCTG AGGAGATCCA GATGGCAGAT TACATCTCCA AAAATGTGCC AGCTACAGAC         884

CACGTGATCC GGAGGGAAGC TGAGACCACG TTCTCTGGGA GCCACTCCTG TTCACCTTCT         944

CACCACTGCT CCACAGCCAC GCCCACCTCC AGCCACAGAC ATGAGAGCCA CACGTGGAGC        1004

CTGGAACGTT CAGAGAGCCT GACCTCGGAT TCCCAGTCAG GCATCATGCT ATCATCAGTA        1064

GGCACCAGCA AGTGCAACAG CCCAGCATGT GTGGAGGCAC GGGCGCGGAG GGCAGCAGCC        1124

TACAGCCAGG AGGAGCGGCG CAGGGCTGCC ATGCCACCCT ACCATGACTC CATAGACTCG        1184

CTGCGTGACT CTCCACACAG TGAAAGGTAC GTGTCAGCCT TGACCACGCC CGCTCGCCTC        1244
```

-continued

```
TCGCCCGTGG ACTTCCACTA CTCGCTGGCC ACGCAGGTGC CGACTTTCGA GATCACGTCG    1304

CCCAACTCTG CGCATGCCGT GTCGCTGCCG CCCGCCGCGC CCATCAGCTA CCGCCTGGCG    1364

GAGCAGCAGC CGCTCCTGCG GCATCCAGCG CCGCCCGGCC CGGGGCCGGG GTCGGGGCCC    1424

GGAGCGGACA TGCAGCGCAG CTACGACAGC TACTACTACC CTGCGGCGGG GCCCGGGCCG    1484

CGGCGCAGCG CCTGCGCGCT GGGAGGCAGC TTGGGCAGCC TGCCCGCCAG CCCCTTCCGC    1544

ATCCCGGAGG ACGACGAGTA CGAGACCACG CAGGAGTGCG CGCCCCCGCC GCCGCCGCGG    1604

CCG                                                                   1607
```

(2) INFORMATION FOR SEQ ID NO:4:

(i) SEQUENCE CHARACTERISTICS:
        (A) LENGTH: 181 amino acids
        (B) TYPE: amino acid
        (C) STRANDEDNESS: Not Relevant
        (D) TOPOLOGY: linear (ii) MOLECULE TYPE: protein (v) FRAGMENT TYPE: internal (xi) SEQUENCE DESCRIPTION: SEQ ID NO:4:

```
Met Lys Ser Gln Thr Gly Glu Val Gly Glu Lys Gln Ser Leu Lys Cys
 1               5                  10                  15

Glu Ala Ala Gly Asn Pro Gln Pro Ser Tyr Arg Trp Phe Lys Asp
            20                  25                  30

Gly Lys Glu Leu Asn Arg Ser Arg Asp Ile Arg Ile Lys Tyr Gly Asn
        35                  40                  45

Val Arg Lys Asn Ser Arg Leu Gln Phe Asn Lys Val Arg Val Glu Asp
    50                  55                  60

Ala Gly Glu Tyr Val Cys Glu Ala Glu Asn Ile Leu Gly Lys Asp Thr
 65                  70                  75                  80

Val Arg Gly Arg Leu His Val Asn Ser Val Ser Thr Thr Leu Ser Ser
                85                  90                  95

Trp Ser Gly His Ala Arg Lys Cys Asn Glu Thr Ala Lys Ser Tyr Cys
            100                 105                 110

Val Asn Gly Gly Val Cys Tyr Tyr Ile Glu Gly Ile Asn Gln Leu Ser
        115                 120                 125

Cys Lys Cys Pro Asn Gly Phe Phe Gly Gln Arg Cys Leu Glu Lys Leu
    130                 135                 140

Pro Leu Arg Leu Tyr Met Pro Asp Pro Lys Gln Ser Val Leu Trp Asp
145                 150                 155                 160

Thr Pro Gly Thr Gly Val Ser Ser Ser Gln Trp Ser Thr Ser Pro Ser
                165                 170                 175

Thr Leu Asp Leu Asn
            180
```

(2) INFORMATION FOR SEQ ID NO:5:

(i) SEQUENCE CHARACTERISTICS:
        (A) LENGTH: 1884 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence (B) LOCATION: 664...1883
(D) OTHER INFORMATION:

(xi) SEQUENCE DESCRIPTION: SEQ ID NO:5:

```
CAGCTACAGC GACAGCAGCA GCAGCAGCAG CGAGAGGAGC AGCAGCAGCA GCAGCAGCAG      60

CAGCGAGAGC GGCAGCAGCA GCAGGAGCAG CAGCAACAAC AGCAGCATCT CTCGTCCCGC     120

TGCGCCCCCA GAGCCGCGGC CGCAGCAACA GCCGCAGCCC CGCAGCCCCG CAGCCCGGAG     180

AGCCGCCGCC CGTTCGCGAG CCGCAGCCGC CGGCGGCATG AGGCGCGACC CGGCCCCCGG     240

CTTCTCCATG CTGCTCTTCG GTGTGTCGCT CGCCTGCTAC TCGCCCAGCC TCAAGTCAGT     300

GCAGGACCAG GCGTACAAGG CACCCGTGGT GGTGGAGGGC AAGGTACAGG GGCTGGTCCC     360

AGCCGGCGGC TCCAGCTCCA ACAGCACCCG AGAGCCGCCC GCCTCGGGTC GGGTGGCGTT     420

GGTAAAGGTG CTGGACAAGT GGCCGCTCCG GAGCGGGGGG CTGCAGCGCG AGCAGGTGAT     480

CAGCGTGGGC TCCTGTGTGC CGCTCGAAAG GAACCAGCGC TACATCTTTT TCCTGGAGCC     540

CACGGAACAG CCCTTAGTCT TTAAGACGGC CTTTGCCCCC CTGATACCAA CGGCAAAAAT     600

CTCAAGAAAG AGGTGGGCAA GATCCTGTGC ACTGGCTGCG CCACCCGGCC CAAGTTGAAG     660
```

```
AAG ATG AAG AGC CAG ACG GGA CAG GTG GGT GAG AAG CAA TCG CTG AAG      708
    Met Lys Ser Gln Thr Gly Gln Val Gly Glu Lys Gln Ser Leu Lys
    1               5                  10                  15

TGT GAG GCA GCA GCC GGT AAT CCC CAG CCT TCC TAC CGT TGG TTC AAG      756
Cys Glu Ala Ala Ala Gly Asn Pro Gln Pro Ser Tyr Arg Trp Phe Lys
                    20                  25                  30

GAT GGC AAG GAG CTC AAC CGC AGC CGA GAC ATT CGC ATC AAA TAT GGC      804
Asp Gly Lys Glu Leu Asn Arg Ser Arg Asp Ile Arg Ile Lys Tyr Gly
                35                  40                  45

AAC GGC AGA AAG AAC TCA CGA CTA CAG TTC AAC AAG GTG AAG GTG GAG      852
Asn Gly Arg Lys Asn Ser Arg Leu Gln Phe Asn Lys Val Lys Val Glu
            50                  55                  60

GAC GCT GGG GAG TAT GTC TGC GAG GCC GAG AAC ATC CTG GGG AAG GAC      900
Asp Ala Gly Glu Tyr Val Cys Glu Ala Glu Asn Ile Leu Gly Lys Asp
65                  70                  75

ACC GTC CGG GGC CGG CTT TAC GTC AAC AGC GTG AGC ACC ACC CTG TCA      948
Thr Val Arg Gly Arg Leu Tyr Val Asn Ser Val Ser Thr Thr Leu Ser
80                  85                  90                  95

TCC TGG TCG GGG CAC GCC CGG AAG TGC AAC GAG ACA GCC AAG TCC TAT      996
Ser Trp Ser Gly His Ala Arg Lys Cys Asn Glu Thr Ala Lys Ser Tyr
                    100                 105                 110

TGC GTC AAT GGA GGC GTC TGC TAC TAC ATC GAG GGC ATC AAC CAG CTC     1044
Cys Val Asn Gly Gly Val Cys Tyr Tyr Ile Glu Gly Ile Asn Gln Leu
                115                 120                 125

TCC TGC AAA TGT CCA AAT GGA TTC TTC GGA CAG AGA TGT TTG GAG AAA     1092
Ser Cys Lys Cys Pro Asn Gly Phe Phe Gly Gln Arg Cys Leu Glu Lys
            130                 135                 140

CTG CCT TTG CGA TTG TAC ATG CCA GAT CCT AAG CAA AAG CAC CTT GGA     1140
Leu Pro Leu Arg Leu Tyr Met Pro Asp Pro Lys Gln Lys His Leu Gly
145                 150                 155

TTT GAA TTA AAG GAA GCC GAG GAG CTG TAC CAG AAG AGG GTC CTG ACC     1188
Phe Glu Leu Lys Glu Ala Glu Glu Leu Tyr Gln Lys Arg Val Leu Thr
160                 165                 170                 175

ATC ACG GGC ATC TGC GTG GCT CTG CTG GTC GTG GGC ATC GTC TGT GTG     1236
Ile Thr Gly Ile Cys Val Ala Leu Leu Val Val Gly Ile Val Cys Val
                    180                 185                 190

GTG GCC TAC TGC AAG ACC AAA AAA CAG CGG AAG CAG ATG CAC AAC CAC     1284
Val Ala Tyr Cys Lys Thr Lys Lys Gln Arg Lys Gln Met His Asn His
                195                 200                 205
```

```
CTC CGG CAG AAC ATG TGC CCG GCC CAT CAG AAC CGG AGC TTG GCC AAT    1332
Leu Arg Gln Asn Met Cys Pro Ala His Gln Asn Arg Ser Leu Ala Asn
        210                 215                 220

GGG CCC AGC CAC CCC CGG CTG GAC CCA GAG GAG ATC CAG ATG GCA GAT    1380
Gly Pro Ser His Pro Arg Leu Asp Pro Glu Glu Ile Gln Met Ala Asp
225                 230                 235

TAT ATT TCC AAG AAC GTG CCA GCC ACA GAC CAT GTC ATC AGG AGA GAA    1428
Tyr Ile Ser Lys Asn Val Pro Ala Thr Asp His Val Ile Arg Arg Glu
240                 245                 250                 255

ACT GAG ACC ACC TTC TCT GGG AGC CAC TCC TGT TCT CCT TCT CAC CAC    1476
Thr Glu Thr Thr Phe Ser Gly Ser His Ser Cys Ser Pro Ser His His
            260                 265                 270

TGC TCC ACA GCC ACA CCC ACC TCC AGC CAC AGA CAC GAG AGC CAC ACG    1524
Cys Ser Thr Ala Thr Pro Thr Ser Ser His Arg His Glu Ser His Thr
            275                 280                 285

TGG AGC CTG GAA CGT TCT GAG AGC CTG ACT TCT GAC TCC CAG TCG GGG    1572
Trp Ser Leu Glu Arg Ser Glu Ser Leu Thr Ser Asp Ser Gln Ser Gly
        290                 295                 300

ATC ATG CTA TCA TCA GTG GGT ACC AGC AAA TGC AAC AGC CCA GCA TGT    1620
Ile Met Leu Ser Ser Val Gly Thr Ser Lys Cys Asn Ser Pro Ala Cys
305                 310                 315

GTG GAG GCC CGG GCA AGG CGG GCA GCA GCC TAC AAC CTG GAG GAG CGG    1668
Val Glu Ala Arg Ala Arg Arg Ala Ala Ala Tyr Asn Leu Glu Glu Arg
320                 325                 330                 335

CGC AGG GCC ACC GCG CCA CCC TAT CAC GAT TCC GTG GAC TCC CTT CGC    1716
Arg Arg Ala Thr Ala Pro Pro Tyr His Asp Ser Val Asp Ser Leu Arg
            340                 345                 350

GAC TCC CCA CAC AGC GAG AGG TAC GTG TCG GCC CTG ACC ACG CCC GCG    1764
Asp Ser Pro His Ser Glu Arg Tyr Val Ser Ala Leu Thr Thr Pro Ala
            355                 360                 365

CGC CTC TCG CCC GTG GAC TTC CAC TAC TCG CTG GCC ACG CAG GTG CCA    1812
Arg Leu Ser Pro Val Asp Phe His Tyr Ser Leu Ala Thr Gln Val Pro
        370                 375                 380

ACT TTC GAG ATC ACG TCC CCC AAC TCG GCG CAC GCC GTG TCG CTG CCG    1860
Thr Phe Glu Ile Thr Ser Pro Asn Ser Ala His Ala Val Ser Leu Pro
385                 390                 395

CCG GCG GCG CCC ATC AGT TAC CGC                                    1884
Pro Ala Ala Pro Ile Ser Tyr Arg
400                 405
```

(2) INFORMATION FOR SEQ ID NO:6:

(i) SEQUENCE CHARACTERISTICS:
        (A) LENGTH: 407 amino acids
        (B) TYPE: amino acid
        (C) STRANDEDNESS: Not Relevant
        (D) TOPOLOGY: linear (ii) MOLECULE TYPE: protein (v) FRAGMENT TYPE: internal (xi) SEQUENCE DESCRIPTION: SEQ ID NO:6:

```
Met Lys Ser Gln Thr Gly Gln Val Gly Glu Lys Gln Ser Leu Lys Cys
1               5                   10                  15

Glu Ala Ala Gly Asn Pro Gln Pro Ser Tyr Arg Trp Phe Lys Asp
            20                  25                  30

Gly Lys Glu Leu Asn Arg Ser Arg Asp Ile Arg Ile Lys Tyr Gly Asn
        35                  40                  45

Gly Arg Lys Asn Ser Arg Leu Gln Phe Asn Lys Val Lys Val Glu Asp
50                  55                  60
```

Ala Gly Glu Tyr Val Cys Glu Ala Glu Asn Ile Leu Gly Lys Asp Thr
 65                  70                  75                  80

Val Arg Gly Arg Leu Tyr Val Asn Ser Val Ser Thr Thr Leu Ser Ser
                 85                  90                  95

Trp Ser Gly His Ala Arg Lys Cys Asn Glu Thr Ala Lys Ser Tyr Cys
            100                 105                 110

Val Asn Gly Gly Val Cys Tyr Tyr Ile Glu Gly Ile Asn Gln Leu Ser
        115                 120                 125

Cys Lys Cys Pro Asn Gly Phe Phe Gly Gln Arg Cys Leu Glu Lys Leu
    130                 135                 140

Pro Leu Arg Leu Tyr Met Pro Asp Pro Lys Gln Lys His Leu Gly Phe
145                 150                 155                 160

Glu Leu Lys Glu Ala Glu Glu Leu Tyr Gln Lys Arg Val Leu Thr Ile
                165                 170                 175

Thr Gly Ile Cys Val Ala Leu Leu Val Val Gly Ile Val Cys Val Val
            180                 185                 190

Ala Tyr Cys Lys Thr Lys Lys Gln Arg Lys Gln Met His Asn His Leu
        195                 200                 205

Arg Gln Asn Met Cys Pro Ala His Gln Asn Arg Ser Leu Ala Asn Gly
210                 215                 220

Pro Ser His Pro Arg Leu Asp Pro Glu Glu Ile Gln Met Ala Asp Tyr
225                 230                 235                 240

Ile Ser Lys Asn Val Pro Ala Thr Asp His Val Ile Arg Arg Glu Thr
                245                 250                 255

Glu Thr Thr Phe Ser Gly Ser His Ser Cys Ser Pro Ser His His Cys
            260                 265                 270

Ser Thr Ala Thr Pro Thr Ser Ser His Arg His Glu Ser His Thr Trp
        275                 280                 285

Ser Leu Glu Arg Ser Glu Ser Leu Thr Ser Asp Ser Gln Ser Gly Ile
        290                 295                 300

Met Leu Ser Ser Val Gly Thr Ser Lys Cys Asn Ser Pro Ala Cys Val
305                 310                 315                 320

Glu Ala Arg Ala Arg Ala Ala Tyr Asn Leu Glu Glu Arg Arg
                325                 330                 335

Arg Ala Thr Ala Pro Pro Tyr His Asp Ser Val Asp Ser Leu Arg Asp
            340                 345                 350

Ser Pro His Ser Glu Arg Tyr Val Ser Ala Leu Thr Thr Pro Ala Arg
        355                 360                 365

Leu Ser Pro Val Asp Phe His Tyr Ser Leu Ala Thr Gln Val Pro Thr
370                 375                 380

Phe Glu Ile Thr Ser Pro Asn Ser Ala His Ala Val Ser Leu Pro Pro
385                 390                 395                 400

Ala Ala Pro Ile Ser Tyr Arg
                405

(2) INFORMATION FOR SEQ ID NO:7:

(i) SEQUENCE CHARACTERISTICS:
        (A) LENGTH: 1476 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence (B) LOCATION: 69...1475
(D) OTHER INFORMATION:

(xi) SEQUENCE DESCRIPTION: SEQ ID NO:7:

```
CGGGCGGCGG GGGCGCAGCG CGGCAGCGGA GAGCTGAGGC CGTCCCACCG CCTGGGACCC          60

CGTGCAGA ATG TCG GAG TCC AGG AGG AGG GGC CGC GGC CGC GGC AAG AAG         110
         Met Ser Glu Ser Arg Arg Arg Gly Arg Gly Arg Gly Lys Lys
         1               5                   10

CAC CCA GAG GGG AGG AAG CGG GAG AGG GAG CCC GAT CCC GGG GAG AAA         158
His Pro Glu Gly Arg Lys Arg Glu Arg Glu Pro Asp Pro Gly Glu Lys
15              20                  25                  30

GCC ACC CGG CCC AAG TTG AAG AAG ATG AAG AGC CAG ACG GGA CAG GTG         206
Ala Thr Arg Pro Lys Leu Lys Lys Met Lys Ser Gln Thr Gly Gln Val
            35                  40                  45

GGT GAG AAG CAA TCG CTG AAG TGT GAG GCA GCA GCC GGT AAT CCC CAG         254
Gly Glu Lys Gln Ser Leu Lys Cys Glu Ala Ala Ala Gly Asn Pro Gln
    50                  55                  60

CCT TCC TAC CGT TGG TTC AAG GAT GGC AAG GAG CTC AAC CGC AGC CGA         302
Pro Ser Tyr Arg Trp Phe Lys Asp Gly Lys Glu Leu Asn Arg Ser Arg
65                  70                  75

GAC ATT CGC ATC AAA TAT GGC AAC GGC AGA AAG AAC TCA CGA CTA CAG         350
Asp Ile Arg Ile Lys Tyr Gly Asn Gly Arg Lys Asn Ser Arg Leu Gln
80              85                  90

TTC AAC AAG GTG AAG GTG GAG GAC GCT GGG GAG TAT GTC TGC GAG GCC         398
Phe Asn Lys Val Lys Val Glu Asp Ala Gly Glu Tyr Val Cys Glu Ala
95              100                 105                 110

GAG AAC ATC CTG GGG AAG GAC ACC GTC CGG GGC CGG CTT TAC GTC AAC         446
Glu Asn Ile Leu Gly Lys Asp Thr Val Arg Gly Arg Leu Tyr Val Asn
            115                 120                 125

AGC GTG AGC ACC ACC CTG TCA TCC TGG TCG GGG CAC GCC CGG AAG TGC         494
Ser Val Ser Thr Thr Leu Ser Ser Trp Ser Gly His Ala Arg Lys Cys
        130                 135                 140

AAC GAG ACA GCC AAG TCC TAT TGC GTC AAT GGA GGC GTC TGC TAC TAC         542
Asn Glu Thr Ala Lys Ser Tyr Cys Val Asn Gly Gly Val Cys Tyr Tyr
    145                 150                 155

ATC GAG GGC ATC AAC CAG CTC TCC TGC AAA TGT CCA AAT GGA TTC TTC         590
Ile Glu Gly Ile Asn Gln Leu Ser Cys Lys Cys Pro Asn Gly Phe Phe
160                 165                 170

GGA CAG AGA TGT TTG GAG AAA CTG CCT TTG CGA TTG TAC ATG CCA GAT         638
Gly Gln Arg Cys Leu Glu Lys Leu Pro Leu Arg Leu Tyr Met Pro Asp
175             180                 185                 190

CCT AAG CAA AAA GCC GAG GAG CTG TAC CAG AAG AGG GTC CTG ACC ATC         686
Pro Lys Gln Lys Ala Glu Glu Leu Tyr Gln Lys Arg Val Leu Thr Ile
            195                 200                 205

ACG GGC ATC TGC GTG GCT CTG CTG GTC GTG GGC ATC GTC TGT GTG GTG         734
Thr Gly Ile Cys Val Ala Leu Leu Val Val Gly Ile Val Cys Val Val
        210                 215                 220

GCC TAC TGC AAG ACC AAA AAA CAG CGG AAG CAG ATG CAC AAC CAC CTC         782
Ala Tyr Cys Lys Thr Lys Lys Gln Arg Lys Gln Met His Asn His Leu
    225                 230                 235

CGG CAG AAC ATG TGC CCG GCC CAT CAG AAC CGG AGC TTG GCC AAT GGG         830
Arg Gln Asn Met Cys Pro Ala His Gln Asn Arg Ser Leu Ala Asn Gly
240                 245                 250

CCC AGC CAC CCC CGG CTG GAC CCA GAG GAG ATC CAG ATG GCA GAT TAT         878
Pro Ser His Pro Arg Leu Asp Pro Glu Glu Ile Gln Met Ala Asp Tyr
255             260                 265                 270

ATT TCC AAG AAC GTG CCA GCC ACA GAC CAT GTC ATC AGG AGA GAA ACT         926
Ile Ser Lys Asn Val Pro Ala Thr Asp His Val Ile Arg Arg Glu Thr
            275                 280                 285
```

```
GAG ACC ACC TTC TCT GGG AGC CAC TCC TGT TCT CCT TCT CAC CAC TGC        974
Glu Thr Thr Phe Ser Gly Ser His Ser Cys Ser Pro Ser His His Cys
        290                 295                 300

TCC ACA GCC ACA CCC ACC TCC AGC CAC AGA CAC GAG AGC CAC ACG TGG       1022
Ser Thr Ala Thr Pro Thr Ser Ser His Arg His Glu Ser His Thr Trp
        305                 310                 315

AGC CTG GAA CGT TCT GAG AGC CTG ACT TCT GAC TCC CAG TCG GGG ATC       1070
Ser Leu Glu Arg Ser Glu Ser Leu Thr Ser Asp Ser Gln Ser Gly Ile
        320                 325                 330

ATG CTA TCA TCA GTG GGT ACC AGC AAA TGC AAC AGC CCA GCA TGT GTG       1118
Met Leu Ser Ser Val Gly Thr Ser Lys Cys Asn Ser Pro Ala Cys Val
335                 340                 345                 350

GAG GCC CGG GCA AGG CGG GCA GCA GCC TAC AAC CTG GAG GAG CGG CGC       1166
Glu Ala Arg Ala Arg Arg Ala Ala Ala Tyr Asn Leu Glu Glu Arg Arg
                355                 360                 365

AGG GCC ACC GCG CCA CCC TAT CAC GAT TCC GTG GAC TCC CTT CGC GAC       1214
Arg Ala Thr Ala Pro Pro Tyr His Asp Ser Val Asp Ser Leu Arg Asp
            370                 375                 380

TCC CCA CAC AGC GAG AGG TAC GTG TCG GCC CTG ACC ACG CCC GCG CGC       1262
Ser Pro His Ser Glu Arg Tyr Val Ser Ala Leu Thr Thr Pro Ala Arg
        385                 390                 395

CTC TCG CCC GTG GAC TTC CAC TAC TCG CTG GCC ACG CAG GTG CCA ACT       1310
Leu Ser Pro Val Asp Phe His Tyr Ser Leu Ala Thr Gln Val Pro Thr
400                 405                 410

TTC GAG ATC ACG TCC CCC AAC TCG GCG CAC GCC GTG TCG CTG CCG CCG       1358
Phe Glu Ile Thr Ser Pro Asn Ser Ala His Ala Val Ser Leu Pro Pro
415                 420                 425                 430

GCG GCG CCC ATC AGT TAC CGC CTG GCC GAG CAG CAG CCG TTA CTG CGG       1406
Ala Ala Pro Ile Ser Tyr Arg Leu Ala Glu Gln Gln Pro Leu Leu Arg
                435                 440                 445

CAC CCG GCG CCC CCC GGC CCG GGA CCC GGA CCC GGG CCC GGG CCC GGG       1454
His Pro Ala Pro Pro Gly Pro Gly Pro Gly Pro Gly Pro Gly Pro Gly
            450                 455                 460

CCC GGC GCA GAC ACC GGA ATT C                                          1476
Pro Gly Ala Asp Thr Gly Ile
        465
```

(2) INFORMATION FOR SEQ ID NO:8:

(i) SEQUENCE CHARACTERISTICS:
        (A) LENGTH: 469 amino acids
        (B) TYPE: amino acid
        (C) STRANDEDNESS: Not Relevant
        (D) TOPOLOGY: linear (ii) MOLECULE TYPE: protein (v) FRAGMENT TYPE: internal (xi) SEQUENCE DESCRIPTION: SEQ ID NO:8:

```
Met Ser Glu Ser Arg Arg Gly Arg Gly Arg Gly Lys Lys His Pro
1               5                   10                  15

Glu Gly Arg Lys Arg Glu Arg Glu Pro Asp Pro Gly Glu Lys Ala Thr
                20                  25                  30

Arg Pro Lys Leu Lys Lys Met Lys Ser Gln Thr Gly Gln Val Gly Glu
            35                  40                  45

Lys Gln Ser Leu Lys Cys Glu Ala Ala Ala Gly Asn Pro Gln Pro Ser
        50                  55                  60

Tyr Arg Trp Phe Lys Asp Gly Lys Glu Leu Asn Arg Ser Arg Asp Ile
65                  70                  75                  80

Arg Ile Lys Tyr Gly Asn Gly Arg Lys Asn Ser Arg Leu Gln Phe Asn
```

```
                    85                  90                  95
Lys Val Lys Val Glu Asp Ala Gly Glu Tyr Val Cys Glu Ala Glu Asn
                100                 105                 110

Ile Leu Gly Lys Asp Thr Val Arg Gly Arg Leu Tyr Val Asn Ser Val
                115                 120                 125

Ser Thr Thr Leu Ser Ser Trp Ser Gly His Ala Arg Lys Cys Asn Glu
130                 135                 140

Thr Ala Lys Ser Tyr Cys Val Asn Gly Val Cys Tyr Tyr Ile Glu
145                 150                 155                 160

Gly Ile Asn Gln Leu Ser Cys Lys Cys Pro Asn Gly Phe Phe Gly Gln
                165                 170                 175

Arg Cys Leu Glu Lys Leu Pro Leu Arg Leu Tyr Met Pro Asp Pro Lys
                180                 185                 190

Gln Lys Ala Glu Glu Leu Tyr Gln Lys Arg Val Leu Thr Ile Thr Gly
                195                 200                 205

Ile Cys Val Ala Leu Leu Val Val Gly Ile Val Cys Val Val Ala Tyr
                210                 215                 220

Cys Lys Thr Lys Lys Gln Arg Lys Gln Met His Asn His Leu Arg Gln
225                 230                 235                 240

Asn Met Cys Pro Ala His Gln Asn Arg Ser Leu Ala Asn Gly Pro Ser
                245                 250                 255

His Pro Arg Leu Asp Pro Glu Glu Ile Gln Met Ala Asp Tyr Ile Ser
                260                 265                 270

Lys Asn Val Pro Ala Thr Asp His Val Ile Arg Arg Glu Thr Glu Thr
                275                 280                 285

Thr Phe Ser Gly Ser His Ser Cys Ser Pro Ser His His Cys Ser Thr
                290                 295                 300

Ala Thr Pro Thr Ser Ser His Arg His Glu Ser His Thr Trp Ser Leu
305                 310                 315                 320

Glu Arg Ser Glu Ser Leu Thr Ser Asp Ser Gln Ser Gly Ile Met Leu
                325                 330                 335

Ser Ser Val Gly Thr Ser Lys Cys Asn Ser Pro Ala Cys Val Glu Ala
                340                 345                 350

Arg Ala Arg Arg Ala Ala Ala Tyr Asn Leu Glu Glu Arg Arg Arg Ala
                355                 360                 365

Thr Ala Pro Pro Tyr His Asp Ser Val Asp Ser Leu Arg Asp Ser Pro
370                 375                 380

His Ser Glu Arg Tyr Val Ser Ala Leu Thr Thr Pro Ala Arg Leu Ser
385                 390                 395                 400

Pro Val Asp Phe His Tyr Ser Leu Ala Thr Gln Val Pro Thr Phe Glu
                405                 410                 415

Ile Thr Ser Pro Asn Ser Ala His Ala Val Ser Leu Pro Pro Ala Ala
                420                 425                 430

Pro Ile Ser Tyr Arg Leu Ala Glu Gln Gln Pro Leu Leu Arg His Pro
                435                 440                 445

Ala Pro Pro Gly Pro Gly Pro Gly Pro Gly Pro Gly Pro Gly Pro Gly
                450                 455                 460

Ala Asp Thr Gly Ile
465
```

(2) INFORMATION FOR SEQ ID NO:9:

(i) SEQUENCE CHARACTERISTICS:
    (A) LENGTH: 422 amino acids (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

Met Ser Glu Arg Lys Glu Gly Arg Gly Lys Gly Lys Gly Lys Lys Lys
1               5                   10                  15

Asp Arg Gly Ser Arg Gly Lys Pro Gly Pro Ala Glu Gly Asp Pro Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
50                  55                  60

Ser Leu Arg Phe Lys Trp Phe Lys Asn Gly Asn Glu Leu Asn Arg Lys
65                  70                  75                  80

Asn Lys Pro Glu Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Phe Ile Thr Gly Met Pro Ala Ser Thr Glu
130                 135                 140

Thr Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Ile Lys Cys Ala Glu Lys Glu Lys Thr Phe Cys Val Asn
            180                 185                 190

Gly Gly Glu Cys Phe Thr Val Lys Asp Leu Ser Asn Pro Ser Arg Tyr
        195                 200                 205

Leu Cys Lys Cys Gln Pro Gly Phe Thr Gly Ala Arg Cys Thr Glu Asn
210                 215                 220

Val Pro Met Lys Val Gln Thr Gln Glu Lys Ala Glu Glu Leu Tyr Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Gln
            260                 265                 270

Lys Leu His Asp Arg Leu Arg Gln Ser Leu Arg Ser Glu Arg Ser Asn
        275                 280                 285

Leu Val Asn Ile Ala Asn Gly Pro His His Pro Asn Pro Pro Pro Glu
290                 295                 300

Asn Val Gln Leu Val Asn Gln Tyr Val Ser Lys Asn Val Ile Ser Ser
305                 310                 315                 320

Glu His Ile Val Glu Arg Glu Val Glu Thr Ser Phe Ser Thr Ser His
                325                 330                 335

Tyr Thr Ser Thr Ala His His Ser Thr Thr Val Thr Gln Thr Pro Ser
            340                 345                 350

His Ser Trp Ser Asn Gly His Thr Glu Ser Val Ile Ser Glu Ser Asn
        355                 360                 365

Ser Val Ile Met Met Ser Ser Val Glu Asn Ser Arg His Ser Ser Pro
370                 375                 380

Ala Gly Gly Pro Arg Gly Arg Leu His Gly Leu Gly Pro Arg Asp
385                 390                 395                 400

Asn Ser Phe Leu Arg His Ala Arg Glu Thr Pro Asp Ser Tyr Arg Asp
            405                 410                 415

Ser Pro His Ser Glu Arg
            420

(2) INFORMATION FOR SEQ ID NO:10:

(i) SEQUENCE CHARACTERISTICS:
       (A) LENGTH: 645 amino acids
       (B) TYPE: amino acid
       (C) STRANDEDNESS: Not Relevant
       (D) TOPOLOGY: linear (ii) MOLECULE TYPE: protein (xi) SEQUENCE DESCRIPTION: SEQ ID NO:10:

Met Ser Glu Arg Lys Glu Gly Arg Gly Lys Gly Lys Gly Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
            35                  40                  45

Ala Gly Ser Lys Leu Val Leu Arg Cys Glu Thr Ser Ser Glu Tyr Ser
50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
            85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Thr Gly Thr
            165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr
            210                 215                 220

Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
            245                 250                 255

Ala Leu Leu Val Val Gly Ile Met Cys Val Val Ala Tyr Cys Lys Thr
            260                 265                 270

Lys Lys Gln Arg Lys Lys Leu His Asp Arg Leu Arg Gln Ser Leu Arg
            275                 280                 285

Ser Glu Arg Asn Asn Met Met Asn Ile Ala Asn Gly Pro His His Pro
290                 295                 300

Asn Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
            325                 330                 335

Phe Ser Thr Ser His Tyr Thr Ser Thr Ala His His Ser Thr Thr Val
            340                 345                 350

Thr Gln Thr Pro Ser His Ser Trp Ser Asn Gly His Thr Glu Ser Ile
            355                 360                 365

Leu Ser Glu Ser His Ser Val Ile Val Met Ser Val Glu Asn Ser
370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
                420                 425                 430

Met Thr Thr Pro Ala Arg Met Ser Pro Val Asp Phe His Thr Pro Ser
            435                 440                 445

Ser Pro Lys Ser Pro Pro Ser Glu Met Ser Pro Val Ser Ser Met
450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
                500                 505                 510

Asp Ser Asn Ser Leu Pro Ala Ser Pro Leu Arg Ile Val Glu Asp Glu
                515                 520                 525

Glu Tyr Glu Thr Thr Gln Glu Tyr Glu Pro Ala Gln Glu Pro Val Lys
                530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
                580                 585                 590

Phe Leu Gly Ile Gln Asn Pro Leu Ala Ala Ser Leu Glu Ala Thr Pro
            595                 600                 605

Ala Phe Arg Leu Ala Asp Ser Arg Thr Asn Pro Ala Gly Arg Phe Ser
610                 615                 620

Thr Gln Glu Glu Ile Gln Ala Arg Leu Ser Ser Val Ile Ala Asn Gln
625                 630                 635                 640

Asp Pro Ile Ala Val
            645

(2) INFORMATION FOR SEQ ID NO:11:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:11:

```
Gly His Ala Arg Lys Cys Asn Glu Thr Ala Lys Ser Tyr Cys Val Asn
1               5                   10                  15

Gly Gly Val Cys Tyr Tyr Ile Glu Gly Ile Asn Gln Leu Ser Cys Lys
            20                  25                  30

Cys Pro Asn Gly Phe Phe Gly Gln Arg Cys Leu Glu Lys Leu Pro
            35                  40                  45
```

(2) INFORMATION FOR SEQ ID NO:12:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
            35                  40                  45

Val Pro
    50
```

(2) INFORMATION FOR SEQ ID NO:13:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

```
Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Gln Pro Gly Phe Thr Gly Ala Arg Cys Thr Glu Asn
            35                  40                  45

Val Pro
    50
```

(2) INFORMATION FOR SEQ ID NO:14:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30
```

```
Leu Cys Lys Cys Pro Asn Glu Phe Thr Gly Asp Arg Cys Gln Asn Tyr
        35                  40                  45

Val Met
    50

(2) INFORMATION FOR SEQ ID NO:15:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

Ser His Leu Thr Lys Cys Asp Ile Lys Gln Lys Ala Phe Cys Val Asn
1               5                   10                  15

Gly Gly Glu Cys Tyr Met Val Lys Asp Leu Pro Asn Pro Pro Arg Tyr
                20                  25                  30

Leu Cys Arg Cys Pro Asn Glu Phe Thr Gly Asp Arg Cys Gln Asn Tyr
        35                  40                  45

Val Met
    50

(2) INFORMATION FOR SEQ ID NO:16:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

Gly Lys Arg Asp Pro Cys Leu Arg Lys Tyr Lys Asp Phe Cys Ile His
1               5                   10                  15

Gly Glu Cys Lys Tyr Val Lys Glu Leu Arg Ala Pro Ser Cys Ile Cys
                20                  25                  30

His Pro Gly Tyr His Gly Glu Arg Cys His Gly Leu Ser Leu
        35                  40                  45

(2) INFORMATION FOR SEQ ID NO:17:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:17:

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
                20                  25                  30

Cys Val Val Gly Tyr Ile Gly Glu Arg Cys Gln Tyr Arg Asp Leu
        35                  40                  45

(2) INFORMATION FOR SEQ ID NO:18:

(i) SEQUENCE CHARACTERISTICS:
```

(A) LENGTH: 46 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:18:

Lys Lys Lys Asn Pro Cys Asn Ala Glu Phe Gln Asn Phe Cys Ile His
1               5                   10                  15

Gly Glu Cys Lys Tyr Ile Glu His Leu Glu Ala Val Thr Cys Lys Cys
            20                  25                  30

Gln Gln Glu Tyr Phe Gly Glu Arg Cys Gly Glu Lys Ser Met
        35                  40                  45

(2) INFORMATION FOR SEQ ID NO:19:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:19:

Ser His Phe Asn Asp Cys Pro Asp Ser His Thr Gln Phe Cys Phe His
1               5                   10                  15

Gly Thr Cys Arg Phe Leu Val Gln Glu Asp Lys Pro Ala Cys Val Cys
            20                  25                  30

His Ser Gly Tyr Val Gly Ala Arg Cys Glu His Ala Asp Leu
        35                  40                  45

(2) INFORMATION FOR SEQ ID NO:20:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:20:

Val Leu Thr Ile Thr Gly Ile Cys Val Ala Leu Leu Val Val Gly Ile
1               5                   10                  15

Val Cys Val Val Ala Tyr Cys
            20

(2) INFORMATION FOR SEQ ID NO:21:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Coding Sequence
        (B) LOCATION: 9...9
        (D) OTHER INFORMATION: where Xaa at position 9 is
            Isoleucine or Valine
        (A) NAME/KEY: Other
        (B) LOCATION: 17...17
        (D) OTHER INFORMATION: where Xaa at position 17 is
            Methionine or Valine (xi) SEQUENCE DESCRIPTION: SEQ ID NO:21:

Val Leu Thr Ile Thr Gly Ile Cys Xaa Ala Leu Leu Val Val Gly Ile
 1               5                  10                  15

Xaa Cys Val Val Ala Tyr Cys
            20

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:22:

GACTTGGCTC TCTCG                                                   15

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:23:

GGACTCCGAC ATTCT                                                   15

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

Met Ala Leu Pro Val Thr Ala Leu Leu Leu Pro Leu Ala Leu Leu Leu
 1               5                  10                  15

His Ala Ala Arg Pro
            20

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:25:

AAAAAGAATT CCTCCATGTC AACAGCGTG                                    29

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:26:

TCCTCTCTCG AGTCACTTAG GATCTGGCAT GTA                               33

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:27:

CACAGTCCAC CCCTCAG                                                      17

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

GCTCTGGTAA GCAAACATGG                                                   20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:29:

TGTGAACTCC TCTGGCCTGT                                                   20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:30:

GAAGGGGCTG GGCATTTAAT                                                   20

(2) INFORMATION FOR SEQ ID NO:31:

(i) SEQUENCE CHARACTERISTICS:
        (A) LENGTH: 2268 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 69...2009
        (D) OTHER INFORMATION:

(xi) SEQUENCE DESCRIPTION: SEQ ID NO:31:

CGGGCGGCGG GGGCGCAGCG CGGCAGCGGA GAGCTGAGGC CGTCCCACCG CCTGGGACCC        60

CGTGCAGA ATG TCG GAG TCC AAG AGG AGG GGC CGC GGC CGC GGC AAG AAG       110
         Met Ser Glu Ser Lys Arg Arg Gly Arg Gly Arg Gly Lys Lys
           1               5                  10

CAC CCA GAG GGG AGG AAG CGG GAG AGG GAG CCC GAT CCC GGG GAG AAA        158
His Pro Glu Gly Arg Lys Arg Glu Arg Glu Pro Asp Pro Gly Glu Lys

-continued

```
15                  20                  25                  30
GCC ACC CGG CCC AAG TTG AAG AAG ATG AAG AGC CAG ACG GGA CAG GTG        206
Ala Thr Arg Pro Lys Leu Lys Lys Met Lys Ser Gln Thr Gly Gln Val
                35                  40                  45

GGT GAG AAG CAA TCG CTG AAG TGT GAG GCA GCA GCC GGT AAT CCC CAG        254
Gly Glu Lys Gln Ser Leu Lys Cys Glu Ala Ala Ala Gly Asn Pro Gln
            50                  55                  60

CCT TCC TAC CGT TGG TTC AAG GAT GGC AAG GAG CTC AAC CGC AGC CGA        302
Pro Ser Tyr Arg Trp Phe Lys Asp Gly Lys Glu Leu Asn Arg Ser Arg
            65                  70                  75

GAC ATT CGC ATC AAA TAT GGC AAC GGC AGA AAG AAC TCA CGA CTA CAG        350
Asp Ile Arg Ile Lys Tyr Gly Asn Gly Arg Lys Asn Ser Arg Leu Gln
        80                  85                  90

TTC AAC AAG GTG AAG GTG GAG GAC GCT GGG GAG TAT GTC TGC GAG GCC        398
Phe Asn Lys Val Lys Val Glu Asp Ala Gly Glu Tyr Val Cys Glu Ala
95                  100                 105                 110

GAG AAC ATC CTG GGG AAG GAC ACC GTC CGG GGC CGG CTT TAC GTC AAC        446
Glu Asn Ile Leu Gly Lys Asp Thr Val Arg Gly Arg Leu Tyr Val Asn
                115                 120                 125

AGC GTG AGC ACC ACC CTG TCA TCC TGG TCG GGG CAC GCC CGG AAG TGC        494
Ser Val Ser Thr Thr Leu Ser Ser Trp Ser Gly His Ala Arg Lys Cys
            130                 135                 140

AAC GAG ACA GCC AAG TCC TAT TGC GTC AAT GGA GGC GTC TGC TAC TAC        542
Asn Glu Thr Ala Lys Ser Tyr Cys Val Asn Gly Gly Val Cys Tyr Tyr
            145                 150                 155

ATC GAG GGC ATC AAC CAG CTC TCC TGC AAA TGT CCA AAT GGA TTC TTC        590
Ile Glu Gly Ile Asn Gln Leu Ser Cys Lys Cys Pro Asn Gly Phe Phe
        160                 165                 170

GGA CAG AGA TGT TTG GAG AAA CTG CCT TTG CGA TTG TAC ATG CCA GAT        638
Gly Gln Arg Cys Leu Glu Lys Leu Pro Leu Arg Leu Tyr Met Pro Asp
175                 180                 185                 190

CCT AAG CAA AAA GCC GAG GAG CTG TAC CAG AAG AGG GTC CTG ACC ATC        686
Pro Lys Gln Lys Ala Glu Glu Leu Tyr Gln Lys Arg Val Leu Thr Ile
                195                 200                 205

ACG GGC ATC TGC GTG GCT CTG CTG GTC GTG GGC ATC GTC TGT GTG GTG        734
Thr Gly Ile Cys Val Ala Leu Leu Val Val Gly Ile Val Cys Val Val
            210                 215                 220

GCC TAC TGC AAG ACC AAA AAA CAG CGG AAG CAG ATG CAC AAC CAC CTC        782
Ala Tyr Cys Lys Thr Lys Lys Gln Arg Lys Gln Met His Asn His Leu
            225                 230                 235

CGG CAG AAC ATG TGC CCG GCC CAT CAG AAC CGG AGC TTG GCC AAT GGG        830
Arg Gln Asn Met Cys Pro Ala His Gln Asn Arg Ser Leu Ala Asn Gly
        240                 245                 250

CCC AGC CAC CCC CGG CTG GAC CCA GAG GAG ATG CAG ATG GCA GAT TAT        878
Pro Ser His Pro Arg Leu Asp Pro Glu Glu Met Gln Met Ala Asp Tyr
255                 260                 265                 270

ATT TCC AAG AAC GTG CCA GCC ACA GAC CAT GTC ATC AGG AGA GAA ACT        926
Ile Ser Lys Asn Val Pro Ala Thr Asp His Val Ile Arg Arg Glu Thr
                275                 280                 285

GAG ACC ACC TTC TCT GGG AGC CAC TCC TGT TCT CCT TCT CAC CAC TGC        974
Glu Thr Thr Phe Ser Gly Ser His Ser Cys Ser Pro Ser His His Cys
            290                 295                 300

TCC ACA GCC ACA CCC ACC TCC AGC CAC AGA CAC GAG AGC CAC ACG TGG       1022
Ser Thr Ala Thr Pro Thr Ser Ser His Arg His Glu Ser His Thr Trp
            305                 310                 315

AGC CTG GAA CGT TCT GAG AGC CTG ACT TCT GAC TCC CAG TCG GGG ATC       1070
Ser Leu Glu Arg Ser Glu Ser Leu Thr Ser Asp Ser Gln Ser Gly Ile
            320                 325                 330

ATG CTA TCA TCA GTG GGT ACC AGC AAA TGC AAC AGC CCA GCA TGT GTG       1118
Met Leu Ser Ser Val Gly Thr Ser Lys Cys Asn Ser Pro Ala Cys Val
```

```
Met Leu Ser Ser Val Gly Thr Ser Lys Cys Asn Ser Pro Ala Cys Val
335                 340                 345                 350

GAG GCC CGG GCA AGG CGG GCA GCA GCC TAC AAC CTG GAG GAG CGG CGC            1166
Glu Ala Arg Ala Arg Arg Ala Ala Ala Tyr Asn Leu Glu Glu Arg Arg
                355                 360                 365

AGG GCC ACC GCG CCA CCC TAT CAC GAT TCC GTG GAC TCC CTT CGC GAC            1214
Arg Ala Thr Ala Pro Pro Tyr His Asp Ser Val Asp Ser Leu Arg Asp
            370                 375                 380

TCC CCA CAC AGC GAG AGG TAC GTG TCG GCC CTG ACC ACG CCC GCG CGC            1262
Ser Pro His Ser Glu Arg Tyr Val Ser Ala Leu Thr Thr Pro Ala Arg
        385                 390                 395

CTC TCG CCC GTG GAC TTC CAC TAC TCG CTG GCC ACG CAG GTG CCA ACT            1310
Leu Ser Pro Val Asp Phe His Tyr Ser Leu Ala Thr Gln Val Pro Thr
    400                 405                 410

TTC GAG ATC ACG TCC CCC AAC TCG GCG CAC GCC GTG TCG CTG CCG CCG            1358
Phe Glu Ile Thr Ser Pro Asn Ser Ala His Ala Val Ser Leu Pro Pro
415                 420                 425                 430

GCG GCG CCC ATC AGT TAC CGC CTG GCC GAG CAG CAG CCG TTA CTG CGG            1406
Ala Ala Pro Ile Ser Tyr Arg Leu Ala Glu Gln Gln Pro Leu Leu Arg
                435                 440                 445

CAC CCG GCG CCC CCC GGC CCG GGA CCC GGA CCC GGG CCC GGG CCC GGG            1454
His Pro Ala Pro Pro Gly Pro Gly Pro Gly Pro Gly Pro Gly Pro Gly
            450                 455                 460

CCC GGC GCA GAC ATG CAG CGC AGC TAT GAC AGC TAC TAT TAC CCC GCG            1502
Pro Gly Ala Asp Met Gln Arg Ser Tyr Asp Ser Tyr Tyr Tyr Pro Ala
        465                 470                 475

GCG GGG CCC GGA CCG CGG CGC GGG ACC TGC GCG CTC GGC GGC AGC CTG            1550
Ala Gly Pro Gly Pro Arg Arg Gly Thr Cys Ala Leu Gly Gly Ser Leu
    480                 485                 490

GGC AGC CTG CCT GCC AGC CCC TTC CGC ATC CCC GAG GAC GAC GAG TAC            1598
Gly Ser Leu Pro Ala Ser Pro Phe Arg Ile Pro Glu Asp Asp Glu Tyr
495                 500                 505                 510

GAG ACC ACG CAG GAG TGC GCG CCC CCG CCG CCG CGG CCG CGC GCG            1646
Glu Thr Thr Gln Glu Cys Ala Pro Pro Pro Pro Arg Pro Arg Ala
                515                 520                 525

CGC GGT GCG TCC CGC AGG ACG TCG GCG GGG CCC CGG CGC TGG CGC CGC            1694
Arg Gly Ala Ser Arg Arg Thr Ser Ala Gly Pro Arg Arg Trp Arg Arg
            530                 535                 540

TCG CGC CTC AAC GGG CTG GCG GCG CAG CGC GCA CGG GCG GCG AGG GAC            1742
Ser Arg Leu Asn Gly Leu Ala Ala Gln Arg Ala Arg Ala Ala Arg Asp
        545                 550                 555

TCG CTG TCG CTG AGC AGC GGC TCG GGC GGC GGC TCA GCC TCG GCG TCG            1790
Ser Leu Ser Leu Ser Ser Ser Gly Gly Gly Gly Ser Ala Ser Ala Ser
    560                 565                 570

GAC GAC GAC GCG GAC GAC GCG GAC GGG GCG CTG GCG GCC GAG AGC ACA            1838
Asp Asp Asp Ala Asp Asp Ala Asp Gly Ala Leu Ala Ala Glu Ser Thr
575                 580                 585                 590

CCT TTC CTG GGC CTG CGT GGG GCG CAC GAC GCG CTG CGC TCG GAC TCG            1886
Pro Phe Leu Gly Leu Arg Gly Ala His Asp Ala Leu Arg Ser Asp Ser
                595                 600                 605

CCG CCA CTG TGC CCG GCG GCC GAC AGC AGG ACT TAC TAC TCA CTG GAC            1934
Pro Pro Leu Cys Pro Ala Ala Asp Ser Arg Thr Tyr Tyr Ser Leu Asp
            610                 615                 620

AGC CAC AGC ACG CGG GCC AGC AGC AGA CAC AGC CGC GGG CCG CCC CCG            1982
Ser His Ser Thr Arg Ala Ser Ser Arg His Ser Arg Gly Pro Pro Pro
        625                 630                 635

CGG GCC AAG CAG GAC TCG GCG CCA CTC TAGGGCCCCG CCGCGCGCCC CTCCGCC         2036
Arg Ala Lys Gln Asp Ser Ala Pro Leu
    640                 645
```

-continued

```
CCGCCCGCCC CACTATCTTT AAGGAGACCA GAGACCGCCT ACTGGAGAGA AAGGAGGAAA    2096

AAAGAAATAA AAATATTTTT ATTTTCTATA AAAGGAAAAA AGTATAACAA AATGTTTTAT    2156

TTTCATTTTA GCAAAAATTG TCTTATAATA CTAGCTAACG GCAAAGGCGT TTTTATAGGG    2216

AAACTATTTA TATGTAACAT CCTGATTTAC AGCTTCGGAA AAAAAAAGA AA             2268
```

(2) INFORMATION FOR SEQ ID NO:32:

(i) SEQUENCE CHARACTERISTICS:
        (A) LENGTH: 647 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:32:

```
Met Ser Glu Ser Lys Arg Arg Gly Arg Gly Arg Gly Lys Lys His Pro
  1               5                  10                  15

Glu Gly Arg Lys Arg Glu Arg Glu Pro Asp Pro Gly Glu Lys Ala Thr
             20                  25                  30

Arg Pro Lys Leu Lys Lys Met Lys Ser Gln Thr Gly Gln Val Gly Glu
         35                  40                  45

Lys Gln Ser Leu Lys Cys Glu Ala Ala Gly Asn Pro Gln Pro Ser
     50                  55                  60

Tyr Arg Trp Phe Lys Asp Gly Lys Glu Leu Asn Arg Ser Arg Asp Ile
 65                  70                  75                  80

Arg Ile Lys Tyr Gly Asn Gly Arg Lys Asn Ser Arg Leu Gln Phe Asn
                 85                  90                  95

Lys Val Lys Val Glu Asp Ala Gly Glu Tyr Val Cys Glu Ala Glu Asn
            100                 105                 110

Ile Leu Gly Lys Asp Thr Val Arg Gly Arg Leu Tyr Val Asn Ser Val
            115                 120                 125

Ser Thr Thr Leu Ser Ser Trp Ser Gly His Ala Arg Lys Cys Asn Glu
        130                 135                 140

Thr Ala Lys Ser Tyr Cys Val Asn Gly Gly Val Cys Tyr Tyr Ile Glu
145                 150                 155                 160

Gly Ile Asn Gln Leu Ser Cys Lys Cys Pro Asn Gly Phe Phe Gly Gln
                165                 170                 175

Arg Cys Leu Glu Lys Leu Pro Leu Arg Leu Tyr Met Pro Asp Pro Lys
            180                 185                 190

Gln Lys Ala Glu Glu Leu Tyr Gln Lys Arg Val Leu Thr Ile Thr Gly
        195                 200                 205

Ile Cys Val Ala Leu Leu Val Val Gly Ile Val Cys Val Val Ala Tyr
    210                 215                 220

Cys Lys Thr Lys Lys Gln Arg Lys Gln Met His Asn His Leu Arg Gln
225                 230                 235                 240

Asn Met Cys Pro Ala His Gln Asn Arg Ser Leu Ala Asn Gly Pro Ser
                245                 250                 255

His Pro Arg Leu Asp Pro Glu Glu Met Gln Met Ala Asp Tyr Ile Ser
            260                 265                 270

Lys Asn Val Pro Ala Thr Asp His Val Ile Arg Arg Glu Thr Glu Thr
        275                 280                 285

Thr Phe Ser Gly Ser His Ser Cys Ser Pro Ser His His Cys Ser Thr
    290                 295                 300
```

Ala Thr Pro Thr Ser Thr His Arg His Glu Ser His Thr Trp Ser Leu
305                 310                 315                 320

Glu Arg Ser Glu Ser Leu Thr Ser Asp Ser Gln Ser Gly Ile Met Leu
            325                 330                 335

Ser Ser Val Gly Thr Ser Lys Cys Asn Ser Pro Ala Cys Val Glu Ala
            340                 345                 350

Arg Ala Arg Arg Ala Ala Ala Tyr Asn Leu Glu Glu Arg Arg Arg Ala
        355                 360                 365

Thr Ala Pro Pro Tyr His Asp Ser Val Asp Ser Leu Arg Asp Ser Pro
    370                 375                 380

His Ser Glu Arg Tyr Val Ser Ala Leu Thr Thr Pro Ala Arg Leu Ser
385                 390                 395                 400

Pro Val Asp Phe His Tyr Ser Leu Ala Thr Gln Val Pro Thr Phe Glu
                405                 410                 415

Ile Thr Ser Pro Asn Ser Ala His Ala Val Ser Leu Pro Pro Ala Ala
            420                 425                 430

Pro Ile Ser Tyr Arg Leu Ala Glu Gln Gln Pro Leu Leu Arg His Pro
        435                 440                 445

Ala Pro Pro Gly Pro Gly Pro Gly Pro Gly Pro Gly Pro Gly Pro Gly
450                 455                 460

Ala Asp Met Gln Arg Ser Tyr Asp Ser Tyr Tyr Tyr Pro Ala Ala Gly
465                 470                 475                 480

Pro Gly Pro Arg Arg Gly Thr Cys Ala Leu Gly Gly Ser Leu Gly Ser
                485                 490                 495

Leu Pro Ala Ser Pro Phe Arg Ile Pro Glu Asp Asp Glu Tyr Glu Thr
            500                 505                 510

Thr Gln Glu Cys Ala Pro Pro Pro Pro Arg Pro Arg Ala Arg Gly
        515                 520                 525

Ala Ser Arg Arg Thr Ser Ala Gly Pro Arg Arg Trp Arg Arg Ser Arg
530                 535                 540

Leu Asn Gly Leu Ala Ala Gln Arg Ala Arg Ala Ala Arg Asp Ser Leu
545                 550                 555                 560

Ser Leu Ser Ser Gly Ser Gly Gly Ser Ala Ser Ala Ser Asp Asp
            565                 570                 575

Asp Ala Asp Asp Ala Asp Gly Ala Leu Ala Ala Glu Ser Thr Pro Phe
            580                 585                 590

Leu Gly Leu Arg Gly Ala His Asp Ala Leu Arg Ser Asp Ser Pro Pro
        595                 600                 605

Leu Cys Pro Ala Ala Asp Ser Arg Thr Tyr Tyr Ser Leu Asp Ser His
    610                 615                 620

Ser Thr Arg Ala Ser Ser Arg His Ser Arg Gly Pro Pro Arg Ala
625                 630                 635                 640

Lys Gln Asp Ser Ala Pro Leu
            645

(2) INFORMATION FOR SEQ ID NO:33:

(i) SEQUENCE CHARACTERISTICS:
        (A) LENGTH: 139 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:33:

-continued

```
Arg Ile Lys Tyr Gly Asn Gly Arg Lys Asn Ser Arg Leu Gln Phe Asn
 1               5                  10                  15

Lys Val Arg Val Glu Asp Ala Gly Glu Tyr Val Cys Glu Ala Glu Asn
            20                  25                  30

Ile Leu Gly Lys Asp Thr Val Arg Gly Arg Leu His Val Asn Ser Val
            35                  40                  45

Ser Thr Thr Leu Ser Ser Trp Ser Gly His Ala Arg Lys Cys Asn Glu
        50                  55                  60

Thr Ala Lys Ser Tyr Cys Val Asn Gly Gly Val Cys Tyr Tyr Ile Glu
 65                  70                  75                  80

Gly Ile Asn Gln Leu Ser Cys Lys Cys Pro Asn Gly Phe Phe Gly Gln
                85                  90                  95

Arg Cys Leu Glu Lys Leu Pro Leu Arg Leu Tyr Met Pro Asp Pro Lys
            100                 105                 110

Gln Ser Val Leu Trp Asp Thr Pro Gly Thr Gly Val Ser Ser Ser Gln
            115                 120                 125

Trp Ser Thr Ser Pro Ser Thr Leu Asp Leu Asn
        130                 135
```

DON-1 GENE AND POLYPEPTIDES AND USES THEREFOR

This application is a divisional of application Ser. No. 08/753,007, filed Nov. 19, 1996, which is a continuation-in-part of application Ser. No. 08/699,591, filed Aug. 19, 1996, now abandoned.

BACKGROUND OF THE INVENTION

This invention relates to a new gene, called don-1, related to growth factors such as the neuregulins, and methods of preparing and using alternate splice forms of this gene to express new Don-1 polypeptides. The invention also relates to the use of these new genes and corresponding polypeptides.

The growth, differentiation, and survival of many cell types depends on the binding of protein ligands to specific cell surface receptors. Misregulation of this interaction has been implicated in a wide variety of tumors and developmental irregularities. For example, the epidermal growth factor receptor (EGFR) family of receptor-type tyrosine kinases are frequently overexpressed, mutated, or deleted in carcinomas of the breast, lung, ovary, brain, and gastrointestinal tract (Prignent et al., *Prog. Growth Factor Res.*, 4:1–24, 1992). This family of receptors, which includes receptors referred to as EGFR, erbB2 (also called "neu" or HER2, the human homolog of erbB2), erbB3 (HER3), and erbB4 (HER4), respectively, may play an important role in the modulation of tumor growth and progression. In particular, it has been shown in several studies that overexpression of erbB2 in a variety of human adenocarcinomas, e.g., in breast and ovarian cancer, correlates with a poor prognosis (see, e.g., Slamon et al., *Science*, 235:177–182, 1987).

One group of ligands that bind to this family of receptors is referred to as the neuregulin family of ligands, which all share a common structural domain known as an EGF motif that contains six cysteines. This motif not only allows these ligands to bind to the receptors, but to mediate biological effects as well (Barbacci et al, *J. Biol. Chem.*, 270:9585–9589, 1995)). Although there appear to be multiple ligands capable of binding to and activating members of the EGFR family, the growth factors that bind to and activate the other members of this receptor family, erbB2, erbB3, and erbB4, are less well characterized.

Neuregulins are also referred to as neu differentiation factors (NDF), glial growth factors (GGF), heregulins, and acetylcholine-receptor-inducing activity (ARIA) ligands, all of which are expressed as variant splice forms of a single gene. These different names reflect the diverse biological activities of the neuregulins in vitro, as glial cell mitogens, receptor binding proteins, mammary differentiation factors, and muscle trophic factors.

Each of the neuregulin glycoproteins has been shown to activate one or more of the receptors erbB2, erbB3, and erbB4 (for a review, see Ben-Baruch et al., *Proc. Soc. Exp. Biol. Med.*, 206:221–227, 1994). These factors were first purified on the basis of their ability to activate, i.e., cause phosphorylation of, the erbB2 receptor, although it has been shown subsequently that these factors do not bind erbB2 directly (Tzahar et al., *J. Biol. Chem.*, 269:25226–25233, 1994). In addition, it has been shown that NDF causes the differentiation of human mammary tumor cells (Peles et al., *Cell*, 69:559–572, 1992).

SUMMARY OF THE INVENTION

The present invention relates to the identification and characterization of a new gene, referred to as don-1, and alternate splice variants of don-1, which are related to the neuregulin gene family. The invention also relates to the polypeptides encoded by don-1. Don-1 mRNA transcripts were expressed in various tissues including murine brain, spleen, and lung, and human fetal brain and fetal lung. No Don-1 transcripts were detected in normal adult human tissues; however, Don-1 transcripts were detected in several human carcinoma cells. In each case, message sizes were about 3.0 kb and 4.4 kb (human) and 4.0 kb (murine).

Both murine and human cDNAs corresponding to various splice variants of don-1 have been cloned. A murine CDNA corresponding to a first splice variant of this gene is represented by SEQ ID NO:1, and the amino acid sequence of the polypeptide it encodes is represented by SEQ ID NO:2, which is a membrane-bound polypeptide approximately 605 amino acids in length (FIGS. 1A–1D). A second murine cDNA corresponding to a second splice variant of the don-1 gene is represented by SEQ ID NO:3, and the amino acid sequence of the polypeptide it encodes is represented by SEQ ID NO:4, which is a secreted polypeptide about 181 amino acids in length (FIGS. 2A–2B).

A human cDNA corresponding to a first splice variant of the human don-1 gene is represented by SEQ ID NO:5, and the amino acid sequence of the polypeptide it encodes is represented by SEQ ID NO:6, which is a membrane-bound polypeptide approximately 407 amino acids in length (FIGS. 3A–3B). A second human cDNA corresponding to a second splice variant of the human don-1 gene is represented by SEQ ID NO:7, and the amino acid sequence of the polypeptide it encodes is represented by SEQ ID NO:8, which is a membrane-bound polypeptide of about 469 amino acids in length (FIGS. 4A–4B).

A third human cDNA corresponding to a third splice variant of the human don-1 gene was isolated by further screening of a human fetal lung library. This sequence had an extended sequence compared to the first two clones, and included a termination codon. This sequence is represented by SEQ ID NO:31, and the amino acid sequence of the polypeptide it encodes is represented by SEQ ID NO:32, which is a membrane-bound polypeptide of about 647 amino acids in length (FIGS. 7A–7C). This sequence appears to be an extended version of the second splice variant (SEQ ID NO:8), although three amino acids differ at the 3' end of SEQ ID NO:32. This third splice variant extends a further 178 amino acids compared to the second human splice variant, and is 94% homologous to murine Don-1 (SEQ ID NO:2) over this region.

In addition, the invention relates to methods of obtaining additional novel ligands that activate some or all members of the EGF receptor family of receptor-type tyrosine kinases, and methods of treating and diagnosing cell proliferative diseases.

In general, the invention features an isolated nucleic acid which encodes a mammalian Don-1 polypeptide, e.g., a polypeptide encoded by any splice variant of a don-1 gene. For example, the nucleic acid can include all or a portion of the nucleotide sequence of, e.g., FIGS. 1A–D, SEQ ID NO:1 (murine), FIGS. 2A–2B, SEQ ID NO:3 (murine), FIGS. 3A–3B, SEQ ID NO:5 (human), FIGS. 4A–4B, SEQ ID NO:7 (human), FIGS. 7A–7C, SEQ ID NO:31 (human), the sequence encoding the epidermal growth factor (EGF) domain of Don-1 having SEQ ID NO:11, or the extracellular domain of Don-1.

The term "nucleic acid" encompasses both RNA and DNA, including cDNA, genomic DNA, and synthetic (e.g., chemically synthesized) DNA. The nucleic acid may be double-stranded or single-stranded. Where single-stranded, the nucleic acid may be a sense strand or an antisense strand.

By "isolated nucleic acid" is meant a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences which are immediately contiguous to the coding sequence. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

A nucleic acid sequence that is "substantially identical" to a don-1 nucleotide sequence is at least 80% or 85%, preferably 90%, and more preferably 95% or more (e.g. 99%) identical to the nucleotide sequence of the human don-1 cDNA of SEQ ID NO:5, NO:7, or NO:31, or the murine don-1 cDNA of SEQ ID NO:1 or NO:3. For purposes of comparison of nucleic acids, the length of the reference nucleic acid sequence will generally be at least 40 nucleotides, preferably at least 60 nucleotides, more preferably at least 75 to 110, or more nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705).

The invention also encompasses nucleic acid sequences that encode forms of Don-1 in which naturally occurring amino acid sequences are altered or deleted.

The invention also features isolated nucleic acid sequences that encode one or more portions or domains of Don-1, including but not limited to the Ig domain, the TM domain, the extracellular domain, the cytoplasmic domain, and various functional domains of Don-1, such as the EGF domain. The nucleic acids also include those of the don-1 gene contained in A.T.C.C. deposit numbers 98096, 98097, or 98098.

Preferred nucleic acids encode polypeptides that are soluble under normal physiological conditions. Also within the invention are nucleic acids encoding fusion proteins in which a portion of Don-1 (e.g., one or more domains) is fused to an unrelated protein or polypeptide (e.g., a marker polypeptide or a fusion partner) to create a fusion protein. For example, the polypeptide can be fused to a hexahistidine tag to facilitate purification of bacterially expressed protein, or to a hemagglutinin tag to facilitate purification of protein expressed in eukaryotic cells.

The fusion partner can be, for example, a polypeptide which facilitates secretion, e.g., a secretory sequence. Such a fused protein is typically referred to as a preprotein. The secretory sequence can be cleaved by the host cell to form the mature protein. Also within the invention are nucleic acids that encode mature Don-1 fused to a polypeptide sequence to produce an inactive proprotein. Proproteins can be converted into the active form of the protein by removal of the inactivating sequence.

The nucleic acids further include nucleic acids that hybridize, e.g., under stringent hybridization conditions (as defined herein), to all or a portion (e.g., the TM or EGF domains) of the nucleotide sequence of SEQ ID NO:1, 3, 5, 7, 31, or its complement, or to the nucleotide sequence of the don-1 gene contained in A.T.C.C. deposit 98096, 98097, or 98098, e.g., nucleic acids that encode polypeptides that activates receptor-type tyrosine kinases that have a molecular weight of about 185 kDa.

The hybridizing portion of the hybridizing nucleic acids are preferably 20, 30, 50, or 70 bases long. Preferably, the hybridizing portion of the hybridizing nucleic acid is 80%, more preferably 95%, or even 98% identical to the sequence of a portion or all of a nucleic acid encoding a Don-1 polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by a naturally-occurring Don-1 polypeptide, e.g., as determined in the p185 assay described below.

Hybridizing nucleic acids can be additional splice variants of the don-1 gene. Thus, they may encode a protein which is shorter or longer than the different forms of Don-1 described herein. Hybridizing nucleic acids may also encode proteins that are related to Don-1 (e.g, proteins encoded by genes which include a portion having a relatively high degree of identity to the don-1 gene described herein).

In another embodiment, the invention features cells, e.g., transformed host cells, harboring a nucleic acid encompassed by the invention. By "transformed cell" is meant a cell into which (or into an ancestor of which) has been introduced, by means of recombinant DNA techniques, a DNA molecule encoding a Don-1 polypeptide.

The invention also features vectors and plasmids that include a nucleic acid of the invention which is operably linked to a transcription and/or translation sequence to enable expression, e.g., expression vectors. By "operably linked" is meant that a selected nucleic acid, e.g., a DNA molecule encoding a Don-1 polypeptide, is positioned adjacent to one or more sequence elements, e.g., a promoter, which direct transcription and/or translation of the sequence such that the sequence elements can control transcription and/or translation of the selected nucleic acid.

The invention also features purified or isolated Don-1 polypeptides. As used herein, both "protein" and "polypeptide" mean any chain of amino acids, regardless of length or post-translational modification (e.g., glycosylation or phosphorylation). Thus, the term "Don-1 polypeptide" (or Don-1) includes full-length, naturally occurring Don-1 protein, as well as recombinantly or synthetically produced polypeptides that correspond to a full-length, naturally occurring Don-1 protein or to particular domains or portions of a naturally occurring protein.

By a "purified" or "isolated" compound is meant a composition which is at least 60% by weight (dry weight) the compound of interest, e.g., a Don-1 polypeptide or antibody. Preferably the preparation is at least 75%, more preferably at least 90%, and most preferably at least 99%, by weight the compound of interest. Purity can be measured by any appropriate standard method, e.g., column chromatography, polyacrylamide gel electrophoresis, or HPLC analysis.

Preferred Don-1 polypeptides include a sequence substantially identical to all or a portion of a naturally occurring Don-1 polypeptide, e.g., including all or a portion of the human sequence shown in FIGS. 3A–3B (SEQ ID NO:6), FIGS. 4A–4B (SEQ ID NO:8), or FIGS. 7A –7C (SEQ ID NO:32), or the murine sequence shown in FIGS. 1A–1D (SEQ ID NO:2) or FIGS. 3A–3B (SEQ ID NO:6). Polypeptides "substantially identical" to the Don-1 polypeptide sequences described herein have an amino acid sequence that is at least 80% or 85%, preferably 90%, and more preferably 95% or more (e.g. 99%) identical to the amino acid sequence of the Don-1 polypeptides of SEQ ID NOs:2, 4, 6, or 8. For purposes of comparison, the length of the reference Don-1 polypeptide sequence will generally be at least 16 amino acids, preferably at least 20 amino acids, more preferably at least 25 amino acids, and most preferably 35 amino acids.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, many other polypeptides will meet the same criteria.

The polypeptides of the invention include, but are not limited to: recombinant polypeptides, natural polypeptides, and synthetic polypeptides as well as polypeptides, which are preproteins or proproteins.

Polypeptides identical or substantially identical to one or more domains of human, murine, or other mammalian Don-1, e.g., the EGF domain (e.g., SEQ ID NO:11)(about amino acid 142 to about amino acid 178 of human Don-1 cDNA SEQ ID NOs:8 and 32, or amino acids 104 to 140 of human Don-1 cDNA SEQ ID NO:6 described herein), or the transmembrane (TM) domain (e.g., SEQ ID NO:20)(about amino acid 203 to about amino acid 225 of human Don-1 cDNA SEQ ID NOs:8 and 32, or amino acids 173 to 195 of human Don-1 cDNA SEQ ID NO:6 described herein), are also within the scope of the invention.

Polypeptides encoded by the don-1 gene contained in A.T.C.C. deposit 98096, 98097, or 98098 are also included within the invention.

Preferred polypeptides are those which are soluble under normal physiological conditions. Also within the invention are soluble fusion proteins in which a full-length form of Don-1 or a portion (e.g., one or more domains) thereof is fused to an unrelated protein or polypeptide (i.e., a fusion partner) to create a fusion protein.

The invention also features isolated polypeptides (and the nucleic acids that encode these polypeptides) that include a first portion and a second portion; the first portion includes a Don-1 polypeptide, e.g., the epidermal growth factor (EGF) domain of Don-1, and the second portion includes an immunoglobulin constant (Fc) region or a detectable marker.

In addition, the invention features a pharmaceutical composition which includes a Don-1 polypeptide and a physiologically acceptable or inert carrier, such as saline.

The invention also features purified or isolated antibodies that specifically bind to a Don-1 polypeptide, or a specific region or domain of a naturally occurring Don-1 protein. By "specifically binds" is meant an antibody that recognizes and binds to a particular antigen, e.g., a Don-1 polypeptide, but which does not substantially recognize and bind to other molecules in a sample, e.g., a biological sample, which naturally includes Don-1. In a preferred embodiment the antibody is a monoclonal antibody.

The invention also features antagonists and agonists of Don-1. Antagonists can inhibit one or more of the functions of Don-1. Suitable antagonists include large or small molecules, antibodies to Don-1, and Don-1 polypeptides which compete with a native form of Don-1. Agonists of Don-1 enhance or facilitate one or more of the functions of Don-1. Suitable agonists include, for example, large or small molecules and anti-idiotype antibodies that mimic the biological effects of Don-1.

Also within the invention are nucleic acid molecules that can be used to interfere with Don-1 expression, e.g., antisense molecules and ribozymes.

In another aspect, the invention features a method for detecting a Don-1 polypeptide. This method includes: obtaining a biological sample; contacting the sample with an antibody, that specifically binds a Don-1 polypeptide, under conditions that allow the formation of Don-1-antibody complexes; and detecting the complexes, if any, as an indication of the presence of Don-1 in the biological sample.

In another aspect, the invention features a method for stimulating proliferation of a cell, by administering to the cell an amount of a Don-1 polypeptide effective to stimulate proliferation of the cell. The invention also features a method for decreasing proliferation of a cell, by administering to the cell an amount of a Don-1 polypeptide inhibitor effective to decrease proliferation of the cell. This method can be used to treat tumors, e.g., adenocarcinomas, caused by the over-proliferation of cells in a patient. Preferably the inhibitor is an antibody which selectively binds to Don-1.

In another embodiment, the invention features a method of obtaining a splice variant cDNA of the don-1 gene. The method includes the steps of obtaining a labeled probe comprising an isolated nucleic acid that encodes all or a portion of the epidermal growth factor (EGF) domain of Don-1, e.g., having the amino acid sequence of SEQ ID NO:11; screening a nucleic acid fragment library with the labeled probe under conditions that allow hybridization of the probe to nucleic acid fragments in the library to form nucleic acid duplexes, isolating labeled duplexes, if any; and preparing a full-length cDNA from the fragments in any labeled duplex to obtain a splice variant cDNA of the don-1 gene.

The invention further features a method of obtaining a gene related to the don-1 gene, by obtaining a labeled probe comprising an isolated nucleic acid that encodes all or a portion of the transmembrane (TM) domain of Don-1, e.g., having the amino acid sequence of SEQ ID NO:20; screening a nucleic acid fragment library with the labeled probe under conditions that allow hybridization of the probe to nucleic acid fragments in the library to form nucleic acid duplexes; isolating labeled duplexes, if any; and preparing a full-length gene sequence from the nucleic acid fragments in any labeled duplex to obtain a gene related to the don-1 gene.

The invention also features a purified protein that functionally interacts with Don-1, and a nucleic acid that encodes a protein that functionally interacts with Don-1.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting Other features and advantages of the invention will be apparent from the following detailed descriptions, and from the claims.

BRIEF DESCRIPTION OF THE DRAWINGS

FIGS. 1A–1D is a representation of the nucleic acid (SEQ ID NO:1) of a murine cDNA corresponding to a membrane-bound splice variant of the don-1 gene, and the amino acid sequence (SEQ ID NO:2) it encodes.

FIGS. 2A–2B is a representation of the nucleic acid (SEQ ID NO:3) of a second murine cDNA corresponding to a secreted splice variant of the don-1 gene, and the amino acid sequence (SEQ ID NO:4) it encodes.

FIGS. 3A–3B is a representation of the nucleic acid (SEQ ID NO:5) of a human cDNA corresponding to a membrane-bound splice variant of the human don-1 gene, and the amino acid sequence (SEQ ID NO:6) it encodes.

FIGS. 4A–4B is a representation of the nucleic acid (SEQ ID NO:7) of a human cDNA corresponding to a second splice variant of the human don-1 gene, and the amino acid sequence (SEQ ID NO:8) it encodes.

FIGS. 5A–5B is a multi-sequence alignment of the amino acid SEQ ID NOs:2, 4, 6, and 8 of FIGS. 1A–1D to 4A–4B, as well as the amino acid sequence of rat neu differentiation factor (NDF)(Genbank Accession No. A38220; SEQ ID NO:9) and human heregulin-β (Genbank Accession No. B43273; SEQ ID NO:10). In this figure, an asterisk above the aligned sequences indicates the location of conserved cysteines in the EGF domain. The transmembrane domains are boxed.

FIG. 6 is a representation of a sequence alignment of the EGF domain of Don-1 (SEQ ID No:11) with the growth factor domains of members of the neuregulin/heregulin family and human heparin binding-EGF (hb-EGF). The domain is bounded by cysteines, and contains a total of six conserved cysteines. FIG. 6 shows additional amino acids upstream and downstream of the EGF domain. Amino acid sequences correspond to a Don-1 EGF polypeptide (SEQ ID NO:11), human heregulin-α (Genbank Accession No. A43273, SEQ ID NO:12), rat NDF (Genbank Accession No. A38220; SEQ ID NO:13), human heregulin-β1 (Genbank Accession No. A43273; SEQ ID NO:14), chicken ARIA (Genbank Accession No. A45769; SEQ ID NO:15); human heparin binding-EGF (Genbank Accession No. A38432; SEQ ID NO:16); human EGF (Genbank Accession No. P01133; SEQ ID NO:17); human amphiregulin (Genbank Accession No. 179040; SEQ ID NO:18); and human TGF-α (Genbank Accession No. 339546; SEQ ID NO:19).

FIGS. 7A–7C is a representation of the nucleic acid (SEQ ID NO:31) of a human cDNA corresponding to a third splice variant of the human don-1 gene, and the amino acid sequence (SEQ ID NO:32) it encodes.

DETAILED DESCRIPTION

Don-1 polypeptides, described here for the first time, are a family of novel glycoprotein ligands related to epidermal growth factors such as the neuregulins. The different Don-1 polypeptides are encoded by different splice variants of the don-1 gene. Don-1 plays a role in proliferation of carcinomas including adenocarcinoma, myeloma, glioma, melanomas, as well as in cell differentiation, proliferation, and survival.

Don-1 polypeptides have a mosaic grouping of functional domains similar to those found in neuregulins (Wen et al., Cell, 69, 559–572, 1992). For example, similar to NDF, both secreted and membrane-bound forms of Don-1 polypeptides include an EGF domain, which enables these ligands to bind to EGF receptors, and to mediate biological effects. As described herein, the EGF domain can also be used to obtain additional splice variants of the don-1 gene.

Also like NDF, membrane-bound forms of Don-1 (SEQ ID NOs:2, 6, 8, and 32) contain a recognized Ig domain, a transmembrane (TM) domain (VLTITGICVALLVVGIVCVVAYC, SEQ ID NO:20), and a cytoplasmic domain. The Ig domain should be important in protein—protein interactions. As described herein, the TM domain can be used to obtain additional new genes related to the don-1 gene. A secreted form of murine Don-1 (SEQ ID NO:4) is a variant splice form that lacks the transmembrane sequence. These domains are described in detail below.

As shown in FIGS. 5A–5B, comparison of a sequence of a human cDNA of Don-1 (SEQ ID NO:8) isolated from human fetal brain, revealed that the EGF domain (about amino acid 142 to about amino acid 178) is 100% identical to the EGF domain in the mouse Don-1 amino acid sequence of SEQ ID NO:2 (about amino acids 104 to 140). In addition, the TM domains (boxed in FIGS. 5A–5B) appear to be highly conserved between mouse and human Don-1 (identical; SEQ ID NO:20), and between Don-1, NDF, and heregulin (2 differences of 23 amino acids). The generic TM domain sequence is VLTITGICX$_1$ALLVVGIX$_2$CVVAYC (SEQ ID NO:21), where $X_1$ is I or V, and $X_2$ is M or V.

The two neighboring basic amino acids adjacent the transmembrane region (amino acids Lys-171 and Arg-172 in the human SEQ ID NO:6; amino acids Lys-201 and Arg-202 in the human SEQ ID NOs:8 and 32; amino acids Lys-163 and Arg-164 in the murine form SEQ ID NO:2) provide for the possibility of processing these proteins with proteolytic enzymes to detach them from the cell membrane.

FIGS. 5A–5B shows the primary structure of both murine and human forms of Don-1 (SEQ ID NOs:2, 4, 6, and 8), as well as the primary structures of rat NDF (SEQ ID NO:9), human heregulin-β (SEQ ID NO:10). As can be seen from this figure, these sequences have highly conserved Ig, EGF (extracellular) and TM domains. Further, there is high homology in the cytoplasmic domains.

Expression of Don-1 in human tissues appeared to be restricted to fetal brain and lung tissues. No Don-1 transcripts were detected in normal adult human tissues using a murine Don-1 cDNA as a probe. However, Don-1 transcripts were detected in a human colon adenocarcinoma cell line SW480 and in a human melanoma cell line G361. In these tissues there were two major Don-1 transcripts of about 4.4 kb and about 3 kb each.

Overall, the human Don-1 cDNA of SEQ ID NO:8 described herein is 95% identical and 98% similar (based on conservative substitutions) at the amino acid level to the murine Don-1 cDNA of SEQ ID NO:2 described herein. The highest homology between the two forms is found in the EGF and transmembrane domains, suggesting that both domains have important functional roles. High homology between the two forms is also found in the Ig and cytoplasmic domains.

Don-1 Proteins and Polypeptides

Don-1 proteins and polypeptides and Don-1 fusion proteins can be prepared for a wide range of uses including, but not limited to, generation of antibodies, preparation of reagents for diagnostic assays, identification of other molecules involved in neoplastic and proliferation (particularly adenocarcinoma), preparation of reagents for use in screening assays for neoplasm modulators, and preparation of therapeutic agents for treatment of tumor-related disorders.

The don-1 gene was originally isolated from a screen of a murine choroid plexus cDNA library. Further screening of other murine and human tissue sources yielded three additional clones of this gene, all representing different splice variants. Based on these cDNA sequences, the don-1 gene can also be obtained by chemical synthesis using one of the methods described in Engels et al. (*Agnew. Chem. Int. Ed. Engl.*, 28:716–734, 1989). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

In particular, FIGS. 1A–1D shows the cDNA of one murine splice variant of don-1 (SEQ ID NO:1), which encodes a predicted protein of about 605 amino acids (SEQ ID NO:2). This clone was isolated from a murine lung cDNA library. The Ig domain begins at a cysteine at about location 16 and extends to a cysteine at about location 70, and should be important in protein—protein interactions. The EGF domain (SEQ ID NO:11), which is predicted to contain the active part of the protein, begins at a cysteine at about amino acid location 104 and extends to a cysteine at about amino acid location 140 in this cDNA.

The spacing of the 6 cysteine resides and an important glycine residue (amino acid 137) in the EGF domain, are conserved between Don-1 and EGF, although homology over this region reveals that Don-1 is more similar to NDF (47% identity) than EGF (35% identity). In general, the EGF domain of Don-1 related polypeptides requires the following formula: the first C, followed by 7 amino acids; the second C, followed by 4 or 5 amino acids; the third C, followed by 10–13 amino acids; the fourth C, followed by 1 amino acid; the fifth C, followed by 8 amino acids; and then the sixth C.

The EGF domain of Don-1 (CNETAKSYCVNGGVCYYIEGINQLSCKCPNGFFGQ-RC, SEQ ID NO:11) is identical in all five splice variants, both murine and human. Thus, probes designed based on the nucleotide region encoding this EGF domain can be used, as described herein, to obtain, in humans, mice, and other animals, additional splice variant cDNAs of the don-1 gene.

The murine Don-1 polypeptide of FIGS. 1A–1D also includes a TM domain of approximately 23 amino acids extending from about amino acid location 165 to about amino acid location 187. Immediately prior to the TM domain are two basic residues (amino acids 163 and 164) that should function as a proteolytic cleavage site. This would result in the release of soluble ligand from the cell membrane. The cytoplasmic domain of Don-1 extends from about amino acid 183 to about amino acid 605.

The Don-1 TM domain (VLTITGICVALLVVGIVCVVAYC, SEQ ID NO:20), like the EGF domain, is also highly conserved in the murine and human membrane-bound splice variants of Don-1 that include this domain (murine SEQ ID NO:4 does not). In fact, the TM domain is identical in both human splice variants and the membrane-bound form of the murine splice variants. As shown in FIGS. 5A–5B, this Don-1 TM domain is also highly conserved in other, related proteins, such as rat NDF, and human heregulin-β. Thus, probes designed based on the nucleotide region encoding this TM domain can be used as described herein to obtain, in humans, mice, and other animals, additional genes related to the don-1 gene.

FIGS. 2A–2B shows a second murine cDNA that corresponds to another splice variant of murine don-1 (SEQ ID NO:3), which encodes a Don-1 polypeptide of 181 amino acids (SEQ ID NO:4). To obtain the nucleotide and amino acids sequences in FIGS. 2A–2B, a 1.4 kb cDNA that contained an open reading frame of 139 amino acids was isolated from a mouse choroid plexus library. This partial clone contained no 5' ATG initiation codon and terminated after the EGF domain. This original clone was then used as a probe to isolate other mouse and human splice variants. The other murine splice variant, SEQ ID NO:1 (FIGS. 1A–1D), represents a longer, transmembrane-bound version of the original clone. Based on the high homology between the two mouse clones over the Ig and EGF domains, the chimeric clone of FIGS. 2A–2B was constructed and designated as the murine Don-1 cDNA of SEQ ID NO:3. This cDNA encompasses the nucleotide sequence encoding the first 42 amino acids of murine Don-1 SEQ ID NO:2, and the remaining 139 amino acids of the original murine Don-1 clone. This resulting chimera is 181 amino acids in length.

This splice variant does not contain a TM domain, and is thus a secreted protein. The structure of this second splice variant is identical to the polypeptide of SEQ ID NO:2 from amino acid I to amino acid 155. Thus, the EGF domain (SEQ ID No:11), which is predicted to contain the biologically active part of the protein, begins at about amino acid location 104 and extends to amino about acid location 140 in this cDNA.

FIGS. 3A–3B shows a cDNA of a human splice variant of the don-1 gene (SEQ ID NO:5), which encodes a polypeptide of about 407 amino acids in length (SEQ ID NO:6). This clone was isolated from a human fetal lung cDNA library. This polypeptide includes an apparent Ig domain extending from a cysteine at about location 16 to a cysteine at about location 70; an EGF domain extending from a cysteine at about location 104 to a cysteine at about amino acid location 140; a transmembrane domain from about amino acid 173 to about amino acid 195; and a cytoplasmic domain of approximately 211 amino acids extending from about amino acid 196 to about amino acid 407. In addition, this splice variant includes an extra 8 amino acids in the juxtamembrane region (at locations 157 to 164) compared to the other three splice variants.

FIGS. 4A–4B shows a second human cDNA corresponding to another splice variant of human don-1 (SEQ ID NO:7), which encodes a polypeptide of about 469 amino acids in length (SEQ ID NO:8). This second human clone was also isolated from a human fetal lung cDNA library. This polypeptide includes an apparent Ig domain extending from a cysteine at about location 54 to a cysteine at about location 108; an EGF domain extending from about amino acid location 142 to about amino acid location 178; a transmembrane domain from about amino acid location 203 to about amino acid location 225; and a cytoplasmic domain of approximately 243 amino acids extending from about amino acid 226 to amino acid 469.

FIGS. 7A–7C shows a third human cDNA corresponding to a third splice variant of the human don-1 gene (SEQ ID NO:31), which encodes a polypeptide of about 647 amino acids in length (SEQ ID NO:32). This third human clone was also isolated from a human fetal lung cDNA library. This polypeptide includes an apparent Ig domain extending from a cysteine at about location 54 to a cysteine at about location 108; an EGF domain extending from about amino acid location 142 to about amino acid location 178; a transmembrane domain from about amino acid location 203 to about amino acid location 225; and a cytoplasmic domain of approximately 421 amino acids extending from about amino acid 226 to amino acid 647 (which is the end of the polypeptide in view of the termination codon).

The invention encompasses, but is not limited to, Don-1 proteins and polypeptides that are functionally related to Don-1 encoded by the nucleotide sequences of FIGS. 1A–1D (murine SEQ ID NO:1), FIGS. 2A–2B (murine SEQ ID NO:3), FIGS. 3A–3B (human SEQ ID NO:5), FIGS. 4A–4B (human SEQ ID NO:7), and FIGS. 7A–7C (human SEQ ID NO:31). Functionally related proteins and polypeptides include any protein or polypeptide sharing a functional characteristic with Don-1, e.g., the ability to affect cell differentiation, proliferation, or survival, and those that are active in the p185 assay described herein.

Such functionally related Don-1 polypeptides include, but are not limited to, polypeptides with additions or substitutions of amino acid residues within the amino acid sequence encoded by the don-1 cDNA sequences described herein which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. The function of the new polypeptide can then be tested in the p185 assay described herein.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to don-1 DNA (using random mutagenesis techniques well known in the art) and the resulting mutant Don-1 proteins can be tested for activity, site-directed mutations of the don-1 coding sequence can be engineered (using site-directed mutagenesis techniques well known to those skilled in the art) to generate mutant Don-1 polypeptides with increased function, e.g., greater modulation of cell proliferation, differentiation or survival, or decreased function, e.g., down-modulation of cell proliferation, differentiation, or survival.

To design functionally related and/or variant Don-1 polypeptides, it is useful to distinguish between conserved positions and variable positions. FIGS. 5A–5B shows an alignment between the amino acid sequences of the human and murine Don-1 polypeptides. This alignment can be used to determine the conserved and variable amino acid positions. To preserve Don-1 function, it is preferable that conserved residues are not altered. Moreover, alteration of non-conserved residues are preferably conservative alterations, e.g., a basic amino acid is replaced by a different basic amino acid. To produce altered function variants, it is preferable to make non-conservative changes at variable and/or conserved positions. Deletions at conserved and variable positions can also be used to create altered function variants.

Other mutations to the don-1 coding sequence can be made to generate Don-1 polypeptides that are better suited for expression, scale up, etc. in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X-T), and/or an amino acid deletion at the second position of any one or more of such recognition sequences, will prevent glycosylation at the modified tripeptide sequence. (See, e.g., Miyajima et al., *EMBO J.*, 5:1193, 1986).

Preferred Don-1 polypeptides are those polypeptides, or variants thereof, that activate receptor-type tyrosine kinases which have a molecular weight of 185 kDa, which includes p185 (erbB2). Activating Don-1 polypeptides can be determined by a standard p185 assay as described herein. Briefly, the activity of the EGF domain of Don-1 was ascertained by testing the ability of an EGF domain-containing fusion polypeptide to phosphorylate a 185 kDa protein in the breast adenocarcinoma cell line MDA-MB453. Serum-starved cells were treated with EGF, NDF, conditioned media from mock-transfected or Don-1 EFG-transfected 293Ebna cells as described below. Analysis of phosphorylated proteins by Western blotting revealed that Don-1 EGF induced phosphorylation of p185 at a level comparable to saturating amounts of NDF, which represented an approximate ten-fold increase in phosphorylation over uninduced cells. This result demonstrates that the EGF domain of Don-1 binds and activates a known member of the EGFR family, p185.

Preferred Don-1 polypeptides and variants have 20%, 50%, 75%, 90%, or even 100% or more of the activity of the human form of Don-1 (SEQ ID NOs:6, 8, and 32) described herein. Such comparisons are generally based on equal concentrations of the molecules being compared. The comparison can also be based on the amount of protein or polypeptide required to reach 50% of the maximal activation obtainable.

In addition to the don-1 cDNA sequences described above, additional splice variants of the don-1 gene, and related family members of the don-1 gene present in the mouse, humans, or other species can be identified and readily isolated without undue experimentation by well known molecular biological techniques given the specific sequences described herein. Further, genes may exist at other genetic loci within the genome that encode proteins which have extensive homology to Don-1 polypeptides or one or more domains of Don-1 polypeptides. These genes can be identified via similar techniques.

For example, to obtain additional splice variants of the don-1 gene, an oligonucleotide probe based on the cDNA sequences described herein, or fragments thereof, e.g., the nucleotide region encoding the EGF domain can be labeled and used to screen a cDNA library constructed from mRNA obtained from an organism of interest. To obtain additional neuregulin-related genes related to the don-1 gene, an oligonucleotide probe based on the nucleotide region encoding the TM domain of Don-1, can be used to screen a suitable cDNA library.

The preferred method of labeling is to use $^{32}$P-labeled ATP with polynucleotide kinase, as is well known in the art, to radiolabel the oligonucleotide probe. However other methods may be used to label the oligonucleotide, including, but not limited to, biotinylation or enzyme labeling.

Hybridization is performed under stringent conditions. Alternatively, a labeled fragment can be used to screen a genomic library derived from the organism of interest, again, using appropriately stringent conditions. Such stringent conditions are well known, and will vary predictably depending on the specific organisms from which the library and the labeled sequences are derived.

Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular SSC or SSPE concentration. Then assume that 1% mismatching results in 1° C. decrease in the $T_m$ and reduce the temperature of the final wash accordingly (for example, if sequences with $\geq 95\%$ identity with the probe are sought, decrease the final wash temperature by 5° C.). Note that this assumption is very approximate, and the actual change in $T_m$ can be between 0.5° and 1.5° C. per 1% mismatch.

As used herein, high stringency conditions include hybridizing at 68° C. in 5×SSC/5×Denhardt solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the desired level of identity between the probe and the target nucleic acid.

For guidance regarding such conditions see, for example, Sambrook et al., 1989, Molecular Cloning, A Laboratory Manual, Cold Springs Harbor Press, N.Y.; and Ausubel et al. (eds.), 1995, Current Protocols in Molecular Biology, (John Wiley & Sons, N.Y.) at Unit 2.10.

In one approach, appropriate human cDNA libraries can be screened. Such cDNA libraries can, for example, include human breast, human prostate, or fetal human brain or lung cDNA libraries. For example, panels of human breast cells can be screened for don-1 expression by, for example, Northern blot analysis. Upon detection of don-1 transcript, cDNA libraries can be constructed from RNA isolated from the appropriate cell line, utilizing standard techniques well known to those of skill in the art. The human cDNA library can then be screened with a don-1 probe to isolate a human don-1 cDNA. As described below, this method was used to determine the human don-1 cDNAs in FIGS. 2A–2B, 4A–4B, and 7A–C.

Alternatively, a human total genomic DNA library can be screened using don-1 probes. Don-1-positive clones can then be sequenced and, further, the intron/exon structure of the human don-1 gene can be elucidated. Once genomic sequence is obtained, oligonucleotide primers can be designed based on the sequence for use in the isolation, via, for example Reverse Transcriptase-coupled PCR, of human don-1 cDNA.

Further, a previously unknown gene sequence can be isolated by performing PCR using two degenerate oligonucleotide primer pools designed on the basis of nucleotide sequences within the don-1 cDNAs defined herein. The template for the reaction can be cDNA obtained by reverse transcription of mRNA prepared from human or non-human cell lines or tissue known or suspected to express a don-1 gene allele. The PCR product can be subcloned and sequenced to insure that the amplified sequences represent the sequences of a don-1 or don-1-like gene nucleic acid sequence.

The PCR fragment can then be used to isolate a full length cDNA clone by a variety of methods. For example, the amplified fragment can be labeled and used to screen a bacteriophage cDNA library. Alternatively, the labeled fragment can be used to screen a genomic library.

PCR technology also can be used to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of useful cloning strategies, see e.g., Sambrook et al., supra; and Ausubel et al., supra.

In cases where the gene identified is the normal (wild type) gene, this gene can be used to isolate mutant alleles of the gene. Such an isolation is preferable in processes and disorders which are known or suspected to have a genetic basis. Mutant alleles can be isolated from individuals either known or suspected to have a genotype which contributes to tumor, e.g., adenocarcinoma, proliferation or progression. Mutant alleles and mutant allele gene products can then be utilized in the therapeutic and diagnostic assay systems described below.

A cDNA of a mutant gene can be isolated, for example, by using PCR, a technique which is well-known to one skilled in the art. In this case, the first cDNA strand can be synthesized by hybridizing a oligo-dT oligonucleotide to mRNA isolated from tissue known or suspected of being expressed in an individual putatively carrying the mutant allele, and by extending the new strand with reverse transcriptase. The second strand of the cDNA can then be synthesized using an oligonucleotide that hybridizes specifically to the 5'- end of the normal gene. Using these two primers, the product is then amplified via PCR, cloned into a suitable vector, and subjected to DNA sequence analysis by methods well known in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof can then be labeled and used as a probe to identify the corresponding mutant allele in the library. The clone containing this gene can then be purified through methods routinely practiced in the art, and subjected to sequence analysis using standard techniques as described herein.

Additionally, an expression library can be constructed using DNA isolated from or cDNA synthesized from a tissue known to or suspected of expressing the gene of interest in an individual suspected of or known to carry the mutant allele. In this manner, gene products made by the putatively mutant tissue can be expressed and screened using standard antibody screening techniques in conjunction with antibodies raised against the normal gene product, as described herein. For screening techniques, see, for example, Harlow, E. and Lane, eds., 1988, "Antibodies: A Laboratory Manual," Cold Spring Harbor Press, Cold Spring Harbor.

In cases where the mutation results in an expressed gene product with altered function (e.g., as a result of a missense mutation), a polyclonal set of antibodies is likely to cross-react with the mutant gene product. Library clones detected via their reaction with such labeled antibodies can be purified and subjected to sequence analysis as described herein.

Polypeptides corresponding to one or more domains of full-length Don-1 protein, e.g., the Ig, TM, and EGF domains, are also within the scope of the invention. Preferred polypeptides are those which are soluble under normal physiological conditions. Also within the invention are fusion proteins in which a portion (e.g., one or more domains) of Don-1 is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of Don-1 is joined in-frame to a nucleotide sequence encoding the fusion partner. Fusion partners include, but are not limited to, the constant region of an immunoglobulin (IgFc). A fusion protein in which a Don-1 polypeptide is fused to IgFc can be more stable and have a longer half-life in the body than the Don-1 polypeptide on its own.

Also within the scope of the invention are various soluble forms of Don-1. For example, the entire extracellular domain of Don-1 or a portion or domain thereof can be expressed on its own or fused to a solubilization partner, e.g., an immunoglobulin.

The invention also features Don-1 polypeptides which can inhibit proliferation of adenocarcinoma cells. The ability of the Don-1 polypeptides to inhibit proliferation of carcinoma cells can be determined using a standard proliferation assay, as follows. Cell, e.g., adenocarcinoma cell, proliferation and viability can be measured by the cleavage of MTT as described by the manufacturer (Boehringer Mannheim, Catalog No. 1465007). Briefly, cells ($2 \times 10^3$) are seeded in separate 100 µL volumes into 96 well tissue culture plates with media containing various concentrations of a Don-1 polypeptide. The plates are then incubated for various times (1 to 3 days) in a humidified atmosphere of 5% $CO_2$ at 37° C. 0.5 mg/ml MTT labeling reagent is added to each well, and the plates are incubated for an additional four hours at 37° C. 100 µL of solubilization buffer is then added to each well and the plates are allowed to stand for 12 hours at 37° C. The spectrophotometrical absorbance at 550 and 690 nm is then measured as a gauge of cell proliferation and viability.

In general, Don-1 proteins according to the invention can be produced by transformation (transfection, transduction, or infection) of a host cell with all or part of a Don-1-encoding DNA fragment (e.g., one of the cDNAs described herein) in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention. The Don-1 protein can be produced in a prokaryotic host (e.g., *E. coli* or *B. subtilis*) or in a eukaryotic host (e.g., Saccharomyces or Pichia; mammalian cells, e.g., COS, NIH 3T3 CHO, BHK, 293, or HeLa cells; or insect cells).

Proteins and polypeptides can also be produced in plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al., supra; expression vehicles may be chosen from those provided, e.g., in Cloning Vectors: A Laboratory Manual (P. H. Pouwels et al., 1985, Supp. 1987).

The host cells harboring the expression vehicle can be cultured in conventional nutrient media adapted as need for activation of a chosen gene, repression of a chosen gene, selection of transformants, or amplification of a chosen gene.

One preferred expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a Don-1 protein would be inserted into the pMAMneo vector in an orientation designed to allow expression. The recombinant Don-1 protein would be isolated as described below. Other preferable host cells that can be used in conjunction with the pMAMneo expression vehicle include COS cells and CHO cells (ATCC Accession Nos. CRL 1650 and CCL 61, respectively).

Don-1 polypeptides can be produced as fusion proteins. For example, the expression vector pUR278 (Ruther et al., *EMBO J*. 2:1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect cell expression system, *Autographa californica* nuclear polyhidrosis virus (AcNPV), which grows in *Spodoptera frugiperda* cells, is used as a vector to express foreign genes. A Don-1 coding sequence can be cloned individually into non-essential regions (for example the polyhedrin gene) of the virus and placed under control of an AcNPV promoter, e.g., the polyhedrin promoter. Successful insertion of a gene encoding a Don-1 polypeptide or protein will result in inactivation of the polyhedrin gene and production of non-occluded recombinant virus (i.e., virus lacking the proteinaceous coat encoded by the polyhedrin gene). These recombinant viruses are then used to infect *spodoptera frugiperda* cells in which the inserted gene is expressed (see, e.g., Smith et al., *J. Virol.* 46:584, 1983; Smith, U.S. Pat. No. 4,215,051).

In mammalian host cells, a number of viral-based expression systems can be utilized. When an adenovirus is used as an expression vector, the Don-1 nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a Don-1 gene product in infected hosts (see, e.g., Logan, Proc. Natl. Acad. Sci. USA 81:3655, 1984).

Specific initiation signals may be required for efficient translation of inserted nucleic acid sequences. These signals include the ATG initiation codon and adjacent sequences. In cases where an entire native Don-1 gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., Methods in Enzymol. 153:516, 1987).

In general, the signal sequence can be a component of the expression vector, or it may be a part of don-1 DNA that is inserted into the vector. The native don-1 DNA is thought to encode a signal sequence at the amino terminus of the polypeptide that is cleaved during post-translational processing to form the mature Don-1 polypeptide that binds to the p185 receptor. However, a conventional signal structure is not apparent. Native Don-1 is secreted from cells, but may remain lodged in the membrane because it contains a transmembrane domain and a cytoplasmic region in the carboxyl terminal region of the polypeptide. Thus, in a secreted, soluble version of Don-1, the carboxyl terminal domain of the molecule, including the transmembrane domain, is ordinarily deleted. This truncated form of the Don-1 polypeptide may be secreted from the cell, provided that the DNA encoding the truncated variant encodes a signal sequence recognized by the host.

Don-1 polypeptides can be expressed directly or as a fusion with a heterologous polypeptide, such as a signal sequence or other polypeptide having a specific cleavage site at the N-and/or C-terminus of the mature protein or polypeptide. Included within the scope of this invention are Don-1 polypeptides with the native signal sequence deleted and replaced with a heterologous signal sequence. The heterologous signal sequence selected should be one that is recognized and processed, i.e., cleaved by a signal peptidase, by the host cell. For prokaryotic host cells that do not recognize and process the native Don-1 signal sequence, the signal sequence is substituted by a prokaryotic signal sequence selected, for example, from the group of the alkaline phosphatase, penicillinase, lpp, or heat-stable enterotoxin II leaders. For yeast secretion the native Don-1 signal sequence may be substituted by the yeast invertase, alpha factor, or acid phosphatase leaders. In mammalian cell expression the native signal sequence is satisfactory, although other mammalian signal sequences may be suitable.

A host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and in particular, choroid plexus cell lines.

Alternatively, a Don-1 protein can be produced by a stably-transfected mammalian cell line. A number of vectors suitable for stable transfection of mammalian cells are available to the public, see, e.g., Pouwels et al. (supra); methods for constructing such cell lines are also publicly available, e.g., in Ausubel et al. (supra). In one example, cDNA encoding the Don-1 protein is cloned into an expression vector that includes the dihydrofolate reductase (DHFR) gene. Integration of the plasmid and, therefore, the Don-1 protein-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include PCVSEII-DHFR and pAdD26SV(A) (described in Ausubel et al., supra). Any of the host cells described above or, preferably, a DHFR-deficient CHO cell line (e.g., CHO $DHFR^-$ cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyl-transferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be readily purified by utilizing an antibody specific for the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, Don-1 or a portion thereof, can be fused to an immunoglobulin Fc domain. Such a fusion protein can be readily purified using a protein A column. Moreover, such fusion proteins permit the production of a dimeric form of a Don-1 polypeptide having increased stability in vivo.

Don-1 proteins and polypeptides can also be expressed in transgenic animals. Animals of any species, including, but not limited to, mice, rats, rabbits, guinea pigs, pigs, micropigs, goats, and non-human primates, e.g., baboons, monkeys, and chimpanzees, can be used to generate Don-1-expressing transgenic animals. Various known techniques can be used to introduce a don-1 transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA*, 82:6148, 1985); gene targeting into embryonic stem cells (Thompson et al., *Cell*, 56:313, 1989); and electroporation of embryos (Lo, *Mol. Cell. Biol.*, 3:1803, 1983).

The present invention provides for transgenic animals that carry the don-1 transgene in all their cells, as well as animals that carry the transgene in some, but not all of their cells, i.e., mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA*, 89:6232, 1992). The regulatory sequences required for such a cell-type specific activation will depend upon the particular cell type of interest, and will be apparent to those of skill in the art.

When it is desired that the don-1 transgene be integrated into the chromosomal site of the endogenous don-1 gene, gene targeting is preferred. Briefly, when such a technique is to be used, vectors containing some nucleotide sequences homologous to an endogenous don-1 gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous don-1 gene in only that cell type (Gu et al., *Science*, 265:103, 1984). The regulatory sequences required for such a cell-type specific inactivation will depend upon the particular cell type of interest, and will be apparent to those of skill in the art.

Once transgenic animals have been generated, the expression of the recombinant don-1 gene can be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of don-1 gene-expressing tissue, also can be evaluated immunocytochemically using antibodies specific for the Don-1 transgene product.

Once the recombinant Don-1 protein is expressed, it is isolated. Secreted forms can be isolated from the culture media, while non-secreted forms must be isolated from the host cells. Proteins can be isolated by affinity chromatography. In one example, an anti-Don-1 protein antibody (e.g., produced as described herein) is attached to a column and used to isolate the Don-1 protein. Lysis and fractionation of Don-1 protein-harboring cells prior to affinity chromatography can be performed by standard methods (see, e.g., Ausubel et al., supra). Alternatively, a Don-1 fusion protein, for example, a Don-1-maltose binding protein, a Don-1-β-galactosidase, or a Don-1-trpE fusion protein, can be constructed and used for Don-1 protein isolation (see, e.g., Ausubel et al., supra; New England Biolabs, Beverly, Mass.).

Once isolated, the recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides of the invention, particularly short Don-1 polypeptides, can be produced by standard chemical synthesis (e.g., by the methods described in *Solid Phase Peptide Synthesis*, 2nd ed., The Pierce Chemical Co., Rockford, Ill., 1984).

These general techniques of polypeptide expression and purification can also be used to produce and isolate useful Don-1 polypeptide analogs (described herein).

The invention also features proteins which interact with Don-1 and are involved in the function of Don-1. Also included in the invention are the genes encoding these interacting proteins. Interacting proteins can be identified using methods known to those skilled in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

Anti-Don-1 Antibodies

Human Don-1 proteins and polypeptides (or immunogenic fragments or analogs) can be used to raise antibodies useful in the invention, and such polypeptides can be produced by recombinant or peptide synthetic techniques (see, e.g., *Solid Phase Peptide Synthesis*, supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a Don-1 protein or polypeptide. Host animals include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Antibodies within the invention include monoclonal antibodies, polyclonal antibodies, humanized or chimeric antibodies, single chain antibodies, Fab fragments, $F(ab')_2$ fragments, and molecules produced using a Fab expression library.

Monoclonal antibodies, which are homogeneous populations of antibodies to a particular antigen, can be prepared using the Don-1 proteins described above and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

In particular, monoclonal antibodies can be obtained by any technique that provides for the production of antibody molecules by continuous cell lines in culture such as described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983), and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridoma producing the mAb of this invention can be cultivated in vitro or in viva. The ability to produce high titers of mAbs in vivo makes this the presently preferred method of production.

Once produced, polyclonal or monoclonal antibodies are tested for specific Don-1 recognition by Western blot or immunoprecipitation analysis by standard methods, e.g., as described in Ausubel et al., supra. Antibodies that specifically recognize and bind to Don-1 are useful in the invention. For example, such antibodies can be used in an immunoassay to monitor the level of Don-1 produced by a mammal (for example, to determine the amount or subcellular location of Don-1).

Preferably, antibodies of the invention are produced using fragments of the Don-1 protein which lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel et al., supra.

Antibodies can also be prepared to bind specifically to one or more particular domains of Don-1, such as the EGF domain (SEQ ID NO:11), by immunizing an animal with a polypeptide corresponding to only the desired domain or domains.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera is also checked for its ability to immunoprecipitate recombinant Don-1 proteins or control proteins, such as glucocorticoid receptor, CAT, or luciferase.

The antibodies can be used, for example, in the detection of the Don-1 in a biological sample as part of a diagnostic assay. Antibodies also can be used in a screening assay to measure the effect of a candidate compound on expression or localization of Don-1.

Additionally, such antibodies can be used in conjunction with the gene therapy techniques described to, for example, evaluate the normal and/or engineered Don-1-expressing cells prior to their introduction into the patient. Such antibodies additionally can be used in a method for inhibiting abnormal Don-1 activity.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against a Don-1 protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to Don-1 can, in turn, be used to generate anti-idiotype antibodies that resemble a portion of Don-1, using techniques well known to those skilled in the art (see, e.g., Greenspan et al., *FASEB J.*, 7:437, 1993; Nissinoff, *J. Immunol.*, 147:2429, 1991). For example, antibodies that bind to Don-1 and competitively inhibit the binding of a ligand of Don-1 can be used to generate anti-idiotypes that resemble a ligand binding domain of Don-1 and, therefore, bind and neutralize a ligand of Don-1. Such neutralizing anti-idiotypic antibodies or Fab fragments of such anti-idiotypic antibodies can be used in therapeutic regimens.

In addition, antibodies can be expressed within an intracellular compartment of a cell, such as the endoplasmic reticulum, to specifically bind to a target protein or polypeptide within the cell. Such specific binding can be used to alter, e.g., inhibit, the function of the target protein. Intracellular expression of antibodies is achieved by introducing into the cells nucleic acids that encode the antibodies, e.g., by using a recombinant viral vector or other vector system suitable for delivering a gene to a cell in vivo.

Preferably the antibody is a single chain Fv fragment, although whole antibodies, or antigen binding fragments thereof, e.g., Fab fragments, can be used. Targeting of an antibody to an intracellular compartment can be accomplished by incorporating an appropriate signal sequence into the antibody. For example, a nucleic acid can be designed to include a first nucleotide sequence encoding a signal sequence (e.g., to an endoplasmic reticulum), operatively linked in a 5' to 3' direction by a phosphodiester bond to a second nucleotide sequence encoding a single chain Fv fragment that binds to a Don-1 polypeptide. These techniques are described in detail in Curiel et al., PCT Publication No. WO 96/07321.

Modulating Don-1 Expression

Don-1 polypeptides can be administered to stimulate the proliferation of cells, such as epithelial cells, e.g., to promote wound healing. Other therapies, e.g., anti-tumor therapies, can be designed to reduce the level of endogenous Don-1 gene expression, e.g., using antisense or ribozyme approaches to inhibit or prevent translation of Don-1 mRNA transcripts; triple helix approaches to inhibit transcription of the Don-1 gene; or targeted homologous recombination to inactivate or "knock out" the Don-1 gene or its endogenous promoter.

Because the Don-1 gene is expressed in the brain, delivery techniques should be preferably designed to cross the blood-brain barrier (see, e.g., PCT Publication No. WO89/10134). Alternatively, the antisense, ribozyme, or DNA constructs described herein could be administered directly to the site containing the target cells; e.g., brain, kidney, lung, uterus, endothelial and epithelial cells, fibroblasts, and breast and prostate cells.

Antisense Nucleic Acids

Antisense approaches involve the design of oligonucleotides (either DNA or RNA) that are complementary to Don-1 mRNA. The antisense oligonucleotides bind to the complementary Don-1 mRNA transcripts and prevent translation. Absolute complementarity, although preferred, is not required. A sequence "complementary" to a portion of an RNA, as referred to herein, means a sequence having sufficient complementarity to be able to hybridize with the RNA and form a stable duplex; in the case of double-stranded antisense nucleic acids, a single strand of the duplex DNA can be tested, or triplex formation can be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well (Wagner, Nature, 372:333, 1984). Thus, oligonucleotides complementary to either the 5'- or 3'-non-translated, non-coding regions of the don-1 gene, e.g., the human gene, as represented by the cDNA (SEQ ID NO:5) shown in FIGS. 3A–3B, can be used in an antisense approach to inhibit translation of endogenous Don-1 mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5'-, 3'-, or coding region of Don-1 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression.

It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA, or chimeric mixtures, or derivatives or modified versions thereof, and can be single-stranded or double-stranded. The oligonucleotides can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA, 86:6553, 1989; Lemaitre et al., Proc. Natl. Acad. Sci. USA, 84:648, 1987; PCT Publication No. WO 88/09810) or the blood-brain barrier (see, e.g., PCT Publication No. WO 89/10134), or hybridization-triggered cleavage agents (see, e.g., Krol et al., BioTechniques, 6:958, 1988), or intercalating agents (see, e.g., Zon, Pharm. Res., 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide can include at least one modified base moiety selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide can also include at least one modified sugar moiety selected from the group including, but not limited to, arabinose, 2-fluoroarabinose, xylulose, and hexose.

In yet another embodiment, the antisense oligonucleotide includes at least one modified phosphate backbone, e.g., a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In addition, the antisense oligonucleotide can be an α-anomeric oligonucleotide that forms specific double-stranded hybrids with complementary RNA in which, contrary to the usual β-units, the strands run parallel to each other (Gautier et al., Nucl. Acids. Res., 15:6625, 1987). The oligonucleotide can be a 2'-O-methylribonucleotide (Inoue et al., Nucl. Acids Res., 15:6131, 1987), or a chimeric RNA-DNA analog (Inoue et al., FEBS Lett., 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al., *Nucl. Acids Res.*, 16:3209, 1988, and methylphosphonate oligonucleotides can be prepared by use of controlled pore glass polymer supports (Sarin et al., *Proc. Natl. Acad. Sci. USA*, 85:7448, 1988).

While antisense nucleotides complementary to the Don-1 coding region sequence could be used, those complementary to the transcribed untranslated region are most preferred.

One example of a 15 nucleotide antisense sequence to the human don-1 gene is directed against the EGF domain: 5'-GACTTGGCTCTCTCG-3' (SEQ ID NO:22). Another example of a 15 nucleotide antisense sequence to the human don-1 gene is: 5'-GGACTCCGAC<u>AT</u>TCT-3' (SEQ ID NO:23), where the underlined sequence represents the complement of the initiator methionine codon.

The antisense molecules should be delivered to cells that express Don-1 in vivo, e.g., brain, kidney, lung, uterus, endothelial and epithelial cells, fibroblasts, and breast and prostate cells. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecules sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous Don-1 transcripts and thereby prevent translation of the Don-1 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature*, 290:304, 1981); the promoter contained in the 3' long terminal repeat of Rous sarcoma virus (Yamamoto et al., *Cell*, 22:787–797, 1988); the herpes thymidine kinase promoter (Wagner et al., *Proc. Natl. Acad. Sci. USA*, 78:1441, 1981); or the regulatory sequences of the metallothionein gene (Brinster et al., *Nature*, 296:39, 1988).

Any type of plasmid, cosmid, YAC, or viral vector can be used to prepare the recombinant DNA construct which can be introduced directly into the tissue site; e.g., the brain, kidney, lung, uterus, endothelial and epithelial cells, fibroblasts, and breast and prostate cells. Alternatively, viral vectors can be used that selectively infect the desired tissue (e.g., for brain, herpesvirus vectors may be used), in which case administration can be accomplished by another route (e.g., systemically).

Ribozymes

Ribozyme molecules designed to catalytically cleave Don-1 mRNA transcripts also can be used to prevent translation of Don-1 mRNA and expression of Don-1 (see, e.g., PCT Publication WO 90/11364; Saraver et al., *Science*, 247:1222, 1990). While various ribozymes that cleave mRNA at site-specific recognition sequences can be used to destroy Don-1 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is known in the art (Haseloff et al., *Nature*, 334:585, 1988). There are numerous examples of potential hammerhead ribozyme cleavage sites within the nucleotide sequence of human Don-1 cDNAs (FIGS. 2A–2B and 4A–4B). Preferably, the ribozyme is engineered so that the cleavage recognition site is located near the 5' end of the Don-1 mRNA, i.e., to increase efficiency and minimize the intracellular accumulation of non-functional mRNA transcripts.

Examples of potential ribozyme sites in human Don-1 include 5'-UG-3' sites which correspond to the initiator methionine codon (nucleotides 664–666 in human SEQ ID NO:5 and 69–71 in human SEQ ID NOs:7 and 31) and the codons for each of the cysteine residues of the EGF domain (e.g., nucleotides 493–494, 517–519, 535–537, 568–570, 574–576, and 601–603 in human SEQ ID NOs:7 and 31, and nucleotides 973–975, 997–999, 1015–1017, 1048–1050, 1054–1056, and 1081–1083 in human SEQ ID NO:5).

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., *Science*, 224:574, 1984; Zaug et al., *Science*, 231:470, 1986; Zug et al., *Nature*, 324:429, 1986; PCT Application No. WO 88/04300; and Been et al., *Cell*, 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in Don-1 polypeptides.

As in the antisense approach, the ribozymes can be composed of modified oligonucleotides (e.g., for improved stability, targeting, etc.), and should be delivered to cells which express the Don-1 in vivo, e.g., brain, kidney, lung, uterus, endothelial and epithelial cells, fibroblasts, and breast and prostate cells. A preferred method of delivery involves using a DNA construct "encoding" the ribozyme under the control of a strong constitutive pol III or pol II promoter, so that transfected cells will produce sufficient quantities of the ribozyme to destroy endogenous Don-1 messages and inhibit translation. Because ribozymes, unlike antisense molecules, are catalytic, a lower intracellular concentration is required for efficiency.

Other Methods for Reducing Don-1 Expression

Endogenous don-1 gene expression can also be reduced by inactivating or "knocking out" the don-1 gene or its promoter using targeted homologous recombination (see, e.g., U.S. Pat. No. 5,464,764). For example, a mutant, non-functional don-1 (or a completely unrelated DNA sequence) flanked by DNA homologous to the endogenous don-1 gene (either the coding regions or regulatory regions of the don-1 gene) can be used, with or without a selectable marker and/or a negative selectable marker, to transfect cells that express Don-1 in vivo. Insertion of the DNA construct, via targeted homologous recombination, results in inactivation of the don-1 gene. Such approaches are particularly suited for use in the agricultural field where modifications to ES (embryonic stem) cells can be used to generate animal offspring with an inactive don-1 gene. This approach can be adapted for use in humans, provided the recombinant DNA constructs are directly administered or targeted to the required site in vivo using appropriate viral vectors, e.g., herpes virus vectors for delivery to brain tissue.

Alternatively, endogenous don-1 gene expression can be reduced by targeting deoxyribonucleotide sequences complementary to the regulatory region of the don-1 gene (i.e., don-1 promoters and/or enhancers located upstream to the start codon in the untranslated region) to form triple helical structures that prevent transcription of the don-1 gene in target cells in the body (Helene, Anticancer Drug Des., 6:569, 1981; Helene et al., *Ann. N.Y. Acad. Sci.*, 660:27, 1992; and Maher, *Bioassays*, 14:807, 1992).

Identification of Proteins That Interact With Don-1

The invention also features proteins that interact with Don-1 polypeptides. Any method suitable for detecting protein-protein interactions can be employed to identify transmembrane, intracellular, or extracellular proteins that interact with Don-1 polypeptides. Among the traditional methods which can be employed are co-immunoprecipitation, crosslinking and co-purification through gradients or chromatographic columns of cell lysates or proteins obtained from cell lysates, and the use of Don-1 polypeptides to identify proteins in the lysate that interact with the Don-1 polypeptide.

For these assays, the Don-1 polypeptide can be a full length Don-1, a soluble extracellular domain of Don-1, or some other suitable Don-1 polypeptide, e.g., a polypeptide including the EGF domain of Don-1. Once isolated, such an interacting protein can be identified and cloned and then used, in conjunction with standard techniques, to identify proteins with which it interacts. For example, at least a portion of the amino acid sequence of a protein which interacts with a Don-1 polypeptide can be ascertained using techniques well known to those of skill in the art, such as via the Edman degradation technique. The amino acid sequence obtained can be used as a guide to generate oligonucleotide mixtures that can be used to screen for gene sequences encoding the interacting protein. Screening can be accomplished, for example, by standard hybridization or PCR techniques. Techniques for generating oligonucleotide mixtures and the screening are known. See, e.g., Ausubel, supra; and PCR Protocols: A Guide to Methods and Applications, 1990, Innis et al., eds. Academic Press, Inc., New York.

Additionally, methods may be employed which result in the direct identification of genes that encode proteins that interact with Don-1 polypeptides. These methods include, for example, screening expression libraries, in a manner similar to the well known technique of antibody probing of λgt11 libraries, using a labeled Don-1 polypeptide or a Don-1 fusion protein, e.g., a Don-1 domain fused to a marker such as an enzyme, fluorescent dye, a luminescent protein, or to an IgFc domain.

There are also methods for detecting protein interactions, e.g., the in vivo two-hybrid system (Chien et al., *Proc. Natl. Acad. Sci. USA*, 88:9578, 1991). A kit for practicing this method is available from Clontech (Palo Alto, Calif.). Briefly, to use this system, plasmids are constructed that encode two hybrid proteins. One plasmid includes a nucleotide sequence encoding the DNA-binding domain of a transcription activator protein fused to a nucleotide sequence encoding a full-length Don-1 protein, a Don-1 polypeptide, or a Don-1 fusion protein. The other plasmid includes a nucleotide sequence encoding the transcription activator protein's activation domain fused to a cDNA encoding an unknown protein from which a cDNA library has been recombined into this plasmid. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site.

Either hybrid protein alone cannot activate transcription of the reporter gene. The DNA-binding domain hybrid cannot because it does not provide activation function, and the activation domain hybrid cannot because it cannot localize to the activator's binding sites. Interaction of the appropriate two hybrid proteins reconstitutes the functional activator protein and results in expression of the reporter gene, which is detected by an assay for the reporter gene product.

The two-hybrid system and related methods can be used to screen activation domain libraries for proteins that interact with a "bait" gene product. By way of example, a Don-1 polypeptide can be used as the bait gene product. Total genomic or cDNA sequences are fused to DNA encoding an activation domain. This library and a plasmid encoding a hybrid of bait Don-1 gene product fused to the DNA-binding domain are cotransformed into a yeast reporter strain, and the resulting transformants are screened for those that express the reporter gene. For example, a bait don-1 gene sequence encoding a Don-1 polypeptide, or a domain of Don-1, can be cloned into a vector such that it is translationally fused to DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait don-1 gene product are to be detected can be made using methods routinely practiced in the art. According to the particular system described herein, for example, cDNA fragments can be inserted into a vector such that they are translationally fused to the transcriptional activation domain of GAL4. This library can be co-transformed along with the bait don-1 gene-GAL4 fusion plasmid into a yeast strain which contains a lacZ gene driven by a promoter that contains a GAL4 activation sequence. A cDNA encoded protein, fused to GAL4 transcriptional activation domain, that interacts with bait don-1 gene product will reconstitute an active GAL4 protein and thereby drive expression of the HIS3 gene. Colonies that express HIS3 then can be purified from these strains, and used to produce and isolate the bait don-1 gene-interacting protein using techniques routinely practiced in the art.

Therapeutic Applications

The Don-1 proteins and polypeptides described herein stimulate proliferation of epithelial cells and are thus particularly implicated in melanomas and adenocarcinomas in which epithelial cells proliferate out of control. Accordingly, undesirable tumors, such as melanomas and adenocarcinomas of the skin, esophagus, lung, breast, liver, pancreas, gastrointestinal tract, colon, prostate, and uterus can be reduced by the administration of a compound that interferes with Don-1 expression or function (e.g., an antibody). Compounds that interfere with Don-1 function can also be used to treat other undesirable disease processes, e.g., cyst and polyp formation.

In addition, since Don-1 polypeptides promote or stimulate epithelial cell proliferation, the topical administration of Don-1 polypeptides to wounds promotes wound healing.

Because Don-1 is highly expressed in the brain, Don-1 also may play a significant role regulating tumor formation and progression in the brain. Of course, in some circumstances, including certain phases of many of the above-described conditions, it may be desirable to enhance Don-1 function, e.g., to stimulate cell proliferation or differentiation, or enhance or suppress apoptosis.

Recombinant Don-1 should facilitate the production of pharmacologic modifiers and inhibitors of Don-1 function. Compounds that interfere with Don-1 function include molecules that bind to Don-1, such as antibodies, and prevent it from binding with its receptors, e.g., p185, or small molecules or anti-idiotype antibodies, that mimic certain domains of Don-1, such as the EGF domain, and bind, preferably irreversibly, to Don-1 receptors without activating these receptors, e.g., without causing phosphorylation or dimerization of these receptors. For example, using standard techniques, a Don-1 EGF polypeptide can be mutated and tested in the p185 assay described herein. Any of these mutant polypeptides that bind to the receptor with high affinity, but do not cause phosphorylation and/or dimerization, are candidates for anti-tumor therapy.

Therapeutic Don-1 polypeptides, antibodies, or small molecules of the invention can be administered by any appropriate route, e.g., injection or infusion by intravenous, intraperitoneal, intracerebral, intramuscular, intraocular, intraarterial, or intralesional routes, or by sustained release systems as note below. Don-1 is administered continuously by infusion or by bolus injection. Don-1 antibodies are administered in the same fashion, or by administration into the blood stream or lymph. Treatment is repeated as necessary for alleviation of disease symptoms.

Suitable examples of sustained-release preparations include semipermeable matrices of solid hydrophobic polymers containing the protein, which matrices are in the form of shaped articles, e.g., films or microcapsules. Examples of sustained-release matrices include polyesters, hydrogels (e.g., poly(2-hydroxyethyl-methacrylate) as described by Langer et al., J. Biomed. Mater. Res., 15:167–277 (1981), and Langer, Chem. Tech., 12:98–105 (1982), or polyvinylalcohol), or polylactides (as described in U.S. Pat. No. 3,773,919, and EPA 58,481).

Sustained-release Don-1 polypeptide or antibody compositions also include liposomally entrapped Don-1 or Don-1 antibodies. Liposomes containing Don-1 or antibody are prepared by methods known per se. See, e.g., Epstein et al., P.N.A.S., USA, 82:3688–3692 (1985); Hwang et al., P.N.A.S., USA, 77:4030–4034 (1980); and U.S. Pat. Nos. 4,485,045 and 4,544,545. The liposomes are preferably about 200–800 Angstroms in diameter and are unilamelar. The lipid content is generally greater than about 30 mol. percent cholesterol, the selected proportion being adjusted for the optimal Don-1 therapy. Liposomes with enhanced circulation time are disclosed in U.S. Pat. No. 5,013,556.

An effective amount of Don-1 or Don-1 antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1.0 μg/kg to about 100 mg/kg or more, depending on the factors mentioned above. Typically, the clinician will administer Don-1 or Don-1 antibody until a dosage is reached that achieves the desired effect. The progress of this therapy is easily monitored by conventional assays.

Diagnostic Applications

The polypeptides of the invention and the antibodies specific for these polypeptides are also useful for identifying those compartments of mammalian cells that contain proteins important to the function of Don-1. Antibodies specific for Don-1 can be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

Antibodies specific for Don-1 also can be used to detect or monitor Don-1-related diseases. For example, levels of a Don-1 protein in a sample can be assayed by any standard technique using these antibodies. For example, Don-1 protein expression can be monitored by standard immunological or immunohistochemical procedures (e.g., those described above) using the antibodies described herein. Alternatively, Don-1 expression can be assayed by standard Northern blot analysis or can be aided by PCR (see, e.g., Ausubel et al., supra; *PCR Technology: Principles and Applications for DNA Amplification*, ed., H. A. Ehrlich, Stockton Press, NY). If desired or necessary, analysis can be carried out to detect point mutations in the Don-1 sequence (for example, using well known nucleic acid mismatch detection techniques). All of the above techniques are enabled by the Don-1 sequences described herein.

EXAMPLES

Example 1 describes the identification and sequencing of several cDNAs corresponding to different splice variants of murine and human don-1 genes. Example 2 describes the characterization of Don-1 using a p185 assay, and differential expression pattern experiments. Example 3 describes chromosomal mapping of the don-1 gene.

Example 1

Cloning of the don-1 Gene

The gene for murine Don-1 was identified in a mouse choroid plexus cDNA library. The first murine splice variant of the don-1 gene was used to identify an additional murine splice variant in a mouse lung cDNA library and two splice variants of the human don-1 gene in a human fetal lung cDNA library. The identification and sequencing of both murine and human genes is described in this first example.

cDNA Library Screening

To obtain a full length cDNA sequence, a mouse lung library (Stratagene, La Jolla, Calif.) was screened using the 1.4 kb NotI/SalI fragment originally isolated from a choroid plexus library as described below. Screening protocols were as described by Sambrook et al., Molecular Cloning: A Laboratory Manual, 2nd ed., (Cold Spring Harbor Press, 1989). A homologous human sequence was obtained from a human fetal brain library (Clontech, Palo Alto, Calif.) by hybridization with a 1.4 kb NotI/SalI fragment of the murine cDNA of SEQ ID NO:1 as described above.

Choroid-Plexus mRNA Isolation

The murine mRNA used to create the murine choroid plexus library was prepared as follows. Total RNA was isolated from mouse choroid plexus tissue using the guanidinium isothiocyanate/CsCl method of Chirgwin et al. (*Biochemistry* 18:5294, 1979) as described in Current Protocols for Molecular Biology (supra). The RNA was quantitated, diluted to 1 mg/ml in water, and then incubated for 30 minutes at 37° C. with an equal volume of DNase solution (20 mM $MgCl_2$, 2 mM DTT, 0.1 units DNase, 0.6 units RNase inhibitor in TE) to remove contaminating DNA. The RNA was then extracted with phenol/chloroform/isoamyl, and ethanol precipitated. After quantitation at 260 nm, an aliquot was electrophoresed to check the integrity of the RNA. Next, Poly $A^+$ RNA was isolated using an Oligotex-dT kit from Qiagen (Chatsworth, Calif.) as described by the manufacturer. After quantitation, the mRNA was precipitated in ethanol and resuspended at a concentration of 1 mg/ml in water.

Choroid plexus mRNA was used as a template for preparation of cDNA according to the method of Gubler et al. (*Gene* 25:263, 1983) using a Superscript Plasmid cDNA synthesis kit (Life Technologies; Gaithersburg, Md.). The cDNA obtained was ligated into the NotI/SalI sites of the mammalian expression vector pMET7, a modified version of pME18S, which utilizes the SRa promoter as described previously (Takebe, *Mol. Cell. Bio.* 8:466, 1988). Ligated cDNA was transformed into electrocompetent DH10B *E. coli* either prepared by standard procedures or obtained from Life Technologies.

DNA Preparation and Sequence Analysis

A cDNA clone from the murine choroid plexus library was sequenced to identify sequences of interest. The identified sequence was then used to clone and sequence a second murine splice variant of the don-1 gene. The identification and analysis is performed as follows.

First, 96-well plates were inoculated with individual choroid plexus library transformants in 1 ml of LB-amp. These inoculations were based on the titers of the cDNA transformants. The resulting cultures were grown for 15 to 16 hours at 37° C. with aeration. Prior to DNA preparation, 100 ml of cell suspension was removed and added to 100 ml of 50% glycerol, mixed and stored at −80° C. (glycerol freeze plate). DNA was then prepared using the Wizard miniprep system (Promega; Madison, Wis.) employing modifications for a 96-well format.

The insert cDNAs of a number of clones were sequenced by standard, automated fluorescent dideoxynucleotide sequencing using dye-primer chemistry (Applied Biosystems, Inc.; Foster City, Calif.) on Applied Biosystems 373 and 377 sequenators (Applied Biosystems). The primer used in this sequencing was proximal to the SRa promoter of the vector and therefore selective for the 5' end of the clones, although other primers with this selectivity can also be used. The short cDNA sequences obtained in this manner were screened as follows.

First, each sequence was checked to determine if it was a bacterial, ribosomal, or mitochondrial contaminant. Such sequences were excluded from the subsequent analysis. Second, sequence artifacts, such as vector and repetitive elements, were masked and/or removed from each sequence. Third, the remaining sequences were searched against a copy of the GenBank nucleotide database using the BLASTN program (BLASTN 1.3MP: Altschul et al., *J. Mol. Bio.* 215:403, 1990). Fourth, the sequences were analyzed against a non-redundant protein database with the BLASTX program (BLASTX 1.3MP: Altschul et al., supra). This protein database is a combination of the Swiss-Prot, PIR, and NCBI GenPept protein databases. The BLASTX program was run using the default BLOSUM-62 substitution matrix with the filter parameter: "xnu+seg". The score cutoff utilized was 75.

Assembly of overlapping clones into contigs was done using the program Sequencher (Gene Codes Corp.; Ann Arbor, Mich.). The assembled contigs were analyzed using the programs in the GCG package (Genetic Computer Group, University Research Park, 575 Science Drive, Madison, Wis. 53711).

The above-described analysis resulted in the identification of a secreted, murine clone having an open reading frame of 139 amino acids. The protein encoded by this clone was named "murine Don-1." The amino-terminal portion of murine Don-1 has significant homology to the known heregulin gene. This portion is 41% identical to human heregulin based on a primary sequence alignment of the Ig and EGF domains of murine Don-1 with human heregulin.

This first splice variant of murine Don-1 was used as a probe to obtain an additional murine splice variant.

Splice variants of the human don-1 gene were isolated in the same way from human fetal brain and fetal lung cDNA libraries (Clontech, Palo Alto, Calif.).

Example 2

Characterization of Don-1

The function of Don-1 polypeptide in a p185 assay and the expression pattern of Don-1 were examined as described below. Also described below is the expression of a recombinant form of soluble murine Don-1.

p185 Assay

MDA-MB453 cells (ATCC, Rockville, Md.) were grown to 80% confluence in DMEM supplemented with 10% FCS in a humidified atmosphere of 5% $CO_2$ at 37° C. The cells were then replated in serum-free media for 24 hours before being exposed to NDF (100 ng/mL), EGF (100 ng/mL), or transfected 293Ebna-conditioned media (10%) for 15 minutes at 37° C. Cell lysates were prepared by solubilizing cells in buffer (1% Triton X-100, 0.5% deoxycholate, 150 mM NaCl, 20 mM Tris pH 8.0, 1 mM EDTA, 30 mM $Na_4P_2O_7$, 50 mM NaF, 0.1 mM $Na_3VO_4$, 10 ug/mL aprotinin, and 1 mM PMSF), and 100 $\mu$g of protein was separated on a 10% SDS PAGE gel. Following transfer to nitrocellulose, immunodetection of phosphorylated proteins was performed using the monoclonal antiphosphotyrosine antibody 4G10 (Upstate Biotechnology, NY) as described by the manufacturer and utilizing Enhanced Chemiluminescence (ECL) (Amersham). NDF and EGF were purchased from R&D Systems (Minneapolis, Minn.).

Analysis of phosphorylated proteins by Western blotting revealed a robust induction of the 185 kDa protein in cells induced with NDF and in cells treated with Don-1 EGF-transfected 293Ebna cells. The level of induction seen with Don-1 EGF was comparable to saturating amounts of NDF and represented an approximate ten-fold increase in phosphorylation over uninduced cells. No induction of phosphorylation was observed in cells treated with EGF or the conditioned media of mock-transfected 293Ebna cells. This result demonstrates that Don-1 binds and activates a known member of the EGFR family, p185.

Analysis of Don-1 Expression

Northern Analysis

Northern analysis was used to examine Don-1 expression as follows. Mouse and human multiple tissue northern blots purchased from Clontech (Palo Alto, Calif.) were hybridized, according to manufacturer's directions, to a 1.4 kb Not/Sal fragment of murine Don-1 polypeptide SEQ ID NO:1, or to the 200 base-pair region encoding the EGF domain which extends from about amino acid location 104 to about amino acid location 140 of SEQ ID NO:1.

This Northern analysis revealed that Don-1 appears to be highly expressed in the mouse brain, although multiple transcripts were also observed in the spleen and lung. The message is also differentially expressed throughout embryogenesis, indicating a possible role in development. In all positive tissues, multiple transcripts exist, the major sizes being about 4 kb and about 3 kb.

Human tissue Northern blots showed that human Don-1 is highly expressed in fetal brain and fetal lung tissues. In addition, two transcripts of about 4 kb and 3 kb were detected exclusively in the cerebellum of human adult tissue. No other normal adult human tissues appeared to express human Don-1. However, Don-1 transcripts were detected in a human colon adenocarcinoma cell line SW480 and in a human melanoma cell line G361. In these tissues there were two major Don-1 transcripts of about 4.4 kb and about 3 kb each.

In Situ Analysis

In situ hybridizations were also used to examine Don-1 expression. Tissues for these hybridizations were prepared as follows. Four to six week old C57BL/6 mice were cervically dislocated, and their brains were removed and frozen on dry ice. Ten µm coronal frozen sections of brain were post-fixed with 4% formaldehyde in 1× phosphate buffered saline (PBS) (25° C.) for 10 minutes, rinsed two times in 1×PBS, rinsed once in 1 M triethanolamine-HCl (pH 8), and then incubated in 0.25% acetic anhydride/1 M triethanolamine-HCl for 10 minutes. Sections were then rinsed in 2×SSC. Tissue was dehydrated through a series of ethanol washes, 70% ethanol for 1 minute, 80% for 1 minute, 95% for 2 minutes, and 100% ethanol for 1 minute. Sections were then incubated in 100% chloroform for 5 minutes and rinsed in 95% ethanol for 1 minute and 100% ethanol for 1 minute. Sections were air dried for 20 minutes.

Hybridizations were performed with $^{35}$S-radiolabeled ($5\times10^7$ cpm/ml) cRNA probes encoding a 472 bp segment of the 5' end of the murine Don-1 gene (SEQ ID NO:1, nucleotides 68–540). Probes were incubated in the presence of 600 mM NaCl, 10 mM Tris, pH 7.5, 1 mM EDTA, 0.01% sheared herring sperm, 0.01% yeast tRNA, 0.05% total yeast sRNA Type X1, 1×Denhardt's solution, 50% formamide, 10% dextran sulfate, 100 mM DTT, 0.1% SDS, and 0.1% Na thiosulfate for 18 hours at 55° C.

After hybridization, slides were washed with 2×SSC. Sections were then incubated with 10 mM Tris-HCl (pH 7.6)/500 mM NaCl/1 mM EDTA (TNE) at 37° C. for 10 minutes, incubated in 10 µg/ml RNase A in TNE at 37° for 30 minutes, and washed in TNE at 37° C. for 30 minutes. Sections were then rinsed with 2×SSC at room temperature, then incubated with 2×SSC at 50° C. for 1 hour, rinsed and incubated with 0.2×SSC at 55° C. for 1 hour, and then incubated with 0.2×SSC at 60° C. for 1 hour. Sections were then dehydrated through a series of ethanols, 50%, 70%, 80%, and 90% with 0.3 M NH$_4$OAc, and 100% ethanol. Sections were air dried and placed on Kodak Biomax MR scientific imaging film for 7 days at room temperature.

mRNA transcripts were localized to the cerebellum and Ammon's horn. Controls for the in situ hybridization experiments included the use of a sense probe which showed no signal above background levels and RNase treated tissue which showed a significantly reduced signal.

Expression Cloning

The EGF domain and flanking amino acids (amino acids 85–154 of SEQ ID NO:1) were amplified by PCR and then subcloned into a variety of commercially available bacterial expression vectors including pGEX (Pharmacia, Uppsala, Sweden), pMAL (NEB, Beverly, Mass.) and pTRX (Invitrogen, San Diego, Calif.). Purification of recombinant material was performed as described by the manufacturer. This same domain was also subcloned into a mammalian expression vector, PN8E and then transfected into 293Ebna cells as detailed by Gibco-BRL (Gaithersburg, Md.). A leader sequence (MALPVTALLLPLALLLHAARP; SEQ ID NO:24) was fused to the N-terminal of the EGF domain by PCR and a Flag epitope tag was placed on the C-terminal, prior to subcloning into PN8E (Ho et al., *P.N.A.S. USA*, 90:11267–11271, 1993).

293Ebna cells at 80 percent confluence in 6-well dishes were transfected with 1.0 µg DNA in 10 µl lipofectamine (Gibco-BRL, Gaithersburg, Md.) for 5 hours at 37° C. in 5 percent CO$_2$ in an 800 µl final volume. Following incubation, DMEM and 10 percent Fetal Calf Serum were added, and the media was replaced 24 hours after the start of transfection. Culture supernatant was collected 48 hours later.

Preparation of Soluble Don-1

Soluble forms of recombinant murine or human Don-1, or domains thereof, can be produced in bacteria using the pGEX expression system as described above for the EGF domain of SEQ ID NO:1. The pGEX-Don-1 is purified on glutathione agarose and the Don-1 moiety released by thrombin digestion. Following endotoxin removal on an Endotoxin BX column (Cape Cod Associates: Falmouth, Mass.) the Don-1 preparation is determined to contain low levels of endotoxin (<0.01 EU/ml) by the Limulus amebocyte lysate (LAL) assay (Cape Cod Associates).

Recombinant, soluble Don-1 is produced as follows. First, the murine Don-1 cDNA is amplified with a primer corresponding to a sequence at the 5' end of the sequence encoding, for example, the EGF domain (5' primer). The 5' primer, 5'-AAAAAAGAATTCCTCCATGTCAACAGCGTG-3' (SEQ ID NO:25), has an EcoRI restriction enzyme cleavage site followed by 18 nucleotides encoding the 5' flanking region of the EGF domain of murine Don-1. The 3' primer used was 5'-TCCTCTCTCGAGTCACTTAGGATCTGGCATGTA-3' (SEQ ID NO:26). This primer has complementary sequences encoding amino acids 187 to 192 preceded by a termination codon and XhoI site.

These primer pairs were used for PCR amplification using the following conditions: 94° C. for 30 seconds; 55° C. for 30 seconds and 72° C. for 90 seconds with 30 cycles. The resulting PCR product was cloned into the GST fusion protein vector pGEX (Pharmacia, Uppsala, Sweden). The fusion protein was produced in *E. coli* and purified according to the protocol supplied by the manufacturer. The Don-1 construct produced a protein of approximately 7.0 kD after the cleavage of GST by thrombin.

Example 3

Mapping of the don-1 Gene

These examples describe chromosome mapping of the mouse and human don-1.

Mouse Chromosome Mapping

The don-1 gene was mapped to the proximal end of chromosome 18 in the mouse, utilizing a *Mus spretus*/C57BL/6J backcross panel. Don-1 appears to be located close to cdc25, 17 cM from the top of chromosome 18, between the markers D18Mit20 and D18Mit24.

PCR primers were used to amplify mouse genomic DNA using standard techniques. Primers were designed from noncoding sequences of murine don-1 and were as follows:

Forward primer: 5'-AGAGGAAGGCCAAAGTAGTG-3' (SEQ ID NO:33), and

Reverse primer: 5'-GTGGACCACAAGGTAAACAG-3' (SEQ ID NO:34).

Other potential primers include:

Forward primer: 5'-CACAGTCCACCCCTCAG-3' (SEQ ID NO:27), and

Reverse primer: 5'-GCTCTGGTAAGCAAACATGG-3' (SEQ ID NO:28).

Amplification conditions were 30 cycles at 95° C. for 1 minute, 60° C. for 1 minute, and 72° C. for 45 seconds. Samples were run on nondenaturing 10% acrylamide SSCP gel at 20 W and 4° C. for 2.5 hours.

Human Chromosome Mapping

Human don-1 can be mapped to a particular chromosome by using a panel of radiation hybrids in a manner similar to that described for the mouse chromosome mapping.

The following primers are used to amplify human genomic DNA from a panel of radiation hybrids (Genebridge 4, Research Genetics, Huntsville, Ala.):

Forward primer: 5'-TGTGAACTCCTCTGGCCTGT-3' (SEQ ID NO:29), and

Reverse primer: 5'-GAAGGGGCTGGGCATTTAAT-3' (SEQ ID NO:30).

The amplification profile is as follows: 94° C. for 30 seconds; 55° C. for 30 seconds, and 72° C. for 45 seconds with 30 cycles. Samples are resolved on 1% agarose TAE gel.

Deposit of Microorganisms

The following microorganisms were deposited with the American Type Culture Collection (ATCC), 10801 University Boulevard, Manassas, Va. 20110-2209, on Jul. 3, 1996 and assigned the indicated accession number:

| Microorganism | ATCC Accession No. |
| --- | --- |
| E. coli CpmDon-1a (SEQ ID NO: 1) (membrane-bound murine Don-1) | 98096 |
| E. coli CphDon-1b (SEQ ID NO: 5) (membrane-bound human Don-1) | 98097 |
| E. coli CpmDon-2 (SEQ ID NO: 3) (secreted murine Don-1) | 98098 |

Deposit Statement

The subject cultures have been deposited under conditions that assure that access to the cultures will be available during the pendency of the patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Other Embodiments

The invention also features fragments, variants, analogs and derivatives of the Don-1 polypeptides described above that retain one or more of the biological activities of Don-1 such as activation of receptor-type tyrosine kinases as described herein.

The invention includes naturally-occurring and non-naturally-occurring allelic variants. Compared to the most common naturally-occurring nucleotide sequence encoding Don-1, the nucleic acid sequence encoding allelic variants may have a substitution, deletion, or addition of one or more nucleotides. The preferred allelic variants are functionally equivalent to naturally-occurring Don-1.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated polypeptide comprising an amino acid sequence selected from the group consisting of SEQ ID NO:2, SEQ ID NO:4, the amino acid sequence encoded by the cDNA insert of the plasmid deposited with the ATCC as Accession Number 98096, and the amino acid sequence encoded by the cDNA insert of the plasmid deposited with the ATCC as Accession Number 98098.

2. An isolated polypeptide comprising the amino acid sequence of SEQ ID NO:2.

3. An isolated polypeptide comprising the amino acid sequence of SEQ ID NO:4.

4. An isolated polypeptide comprising an amino acid sequence selected from the group consisting of SEQ ID NO:6, SEQ ID NO:8, SEQ ID NO:32, and the amino acid sequence encoded by the cDNA insert of the plasmid deposited with the ATCC as Accession Number 98097.

5. An isolated polypeptide comprising the amino acid sequence of SEQ ID NO:6.

6. An isolated polypeptide comprising the amino acid sequence of SEQ ID NO:8.

7. An isolated polypeptide comprising the amino acid sequence of SEQ ID NO:32.

8. An isolated polypeptide comprising the extracellular domain of a polypeptide comprising the amino acid sequence of SEQ ID NO:2.

9. An isolated polypeptide comprising the extracellular domain of a polypeptide comprising the amino acid sequence of SEQ ID NO:6.

10. An isolated polypeptide comprising the extracellular domain of a polypeptide comprising the amino acid sequence of SEQ ID NO:8.

11. An isolated polypeptide comprising the extracellular domain of a polypeptide comprising the amino acid sequence of SEQ ID NO:32.

12. An isolated polypeptide comprising a first polypeptide portion and a second polypeptide portion, the first portion comprising the polypeptide as in any of claims 1–3, 4–7, 8, 9, 10 or 11, and the second portion comprising a polypeptide that is unrelated to the first portion.

13. The polypeptide of claim 12, wherein the second portion comprises an immunoglobulin (Fc) domain.

* * * * *